United States Patent
Hurt et al.

(10) Patent No.: US 11,192,948 B2
(45) Date of Patent: Dec. 7, 2021

(54) COMPOSITIONS AND METHODS FOR INHIBITING CANCER STEM CELLS

(71) Applicant: MedImmune Limited, Cambridge (GB)

(72) Inventors: Elaine M. Hurt, Gaithersburg, MD (US); Ralph Minter, Cambridge (GB); Steven Rust, Cambridge (GB); Alan Sandercock, Cambridge (GB); Sotirios Karathanasis, Gaithersburg, MD (US)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 15/764,629

(22) PCT Filed: Sep. 29, 2016

(86) PCT No.: PCT/EP2016/073362
§ 371 (c)(1),
(2) Date: Mar. 29, 2018

(87) PCT Pub. No.: WO2017/055511
PCT Pub. Date: Apr. 6, 2017

(65) Prior Publication Data
US 2018/0273616 A1    Sep. 27, 2018

Related U.S. Application Data

(60) Provisional application No. 62/235,144, filed on Sep. 30, 2015.

(51) Int. Cl.
| | |
|---|---|
| *C07K 16/28* | (2006.01) |
| *C07K 16/30* | (2006.01) |
| *C12N 5/095* | (2010.01) |
| *G01N 33/574* | (2006.01) |
| *C12Q 1/25* | (2006.01) |
| *A61K 31/713* | (2006.01) |
| *A61K 31/704* | (2006.01) |
| *A61K 39/00* | (2006.01) |

(52) U.S. Cl.
CPC ............ *C07K 16/28* (2013.01); *A61K 31/704* (2013.01); *A61K 31/713* (2013.01); *C07K 16/2851* (2013.01); *C07K 16/30* (2013.01); *C12N 5/0695* (2013.01); *C12Q 1/25* (2013.01); *G01N 33/574* (2013.01); *A61K 2039/505* (2013.01); *C07K 2317/76* (2013.01); *C07K 2318/00* (2013.01)

(58) Field of Classification Search
CPC ................................. C07K 16/28; C07K 16/30
USPC ...................................................... 424/172.1
See application file for complete search history.

(56) References Cited

U.S. PATENT DOCUMENTS

| | | | |
|---|---|---|---|
| 2009/0311271 A1 | 12/2009 | Wyeth | |
| 2015/0030636 A1* | 1/2015 | Dylla ................... | C12N 5/0693 424/277.1 |

FOREIGN PATENT DOCUMENTS

| | | |
|---|---|---|
| CN | 101668772 A | 3/2010 |
| CN | 103582815 A | 2/2014 |
| JP | 2006022063 A | 1/2006 |
| WO | 2008103953 A2 | 8/2008 |
| WO | 2010138171 A2 | 12/2010 |
| WO | 2012115820 A2 | 8/2012 |
| WO | 2013119964 A2 | 8/2013 |
| WO | 2014028274 A1 | 2/2014 |
| WO | 2014205302 A2 | 12/2014 |
| WO | 2016/050889 A1 | 4/2016 |

OTHER PUBLICATIONS

Yokoyama, et al., "Abstract 11713: Knockout Mice Preserve Against Doxorubicin-Induced Cardiomyopathy," *Circulation*, 2011, vol. 124, Issue suppl. 21, p. 1.

Meng, et al., "Tumor stem cells: A new approach for tumor therapy (Review)", Oncology Letters, 2012, pp. 187-193, 4(2).

Lu, et al., "Oxidative Stress and Lectin-Like OX-LDL-Receptor LOX-1 in Atherogenesis and Tumorigenesis", Antioxidants & Redox Signaling, 2011, pp. 2301-2333, vol. 15, No. 8.

Wang, "Lectin-like oxidized low density lipoprotein receptor-1," 2009, International Journal of Cardiovascular Disease, vol. 36, Issue No. 4, pp. 225-231.

Chen, "The New Techniques and Methods in Pharmacological Research," 2014, Peking Union Medical College Press, pp. 314-315.

Gong, "Radiation Cytobiology," 2014, China Atomic Energy Press, p. 461.

Spallarossa et al., "Doxorubicin-induced expression of LOX-1 in H9c2 cardiac muscle cells and its role in apoptosis", Biochemical and Biophysical Research Communications 335 (2005) pp. 188-196.

Kiselev et al. "3.3'-Diindolylmethane—Selective Inhibitor Activities of Tumor Stem Cells", Molecular Medicine, No. 4, 2012, pp. 1-9.

* cited by examiner

*Primary Examiner* — Yan Xiao

(57) ABSTRACT

The disclosure generally provides compositions and methods that are useful in the treatment of cancer. More specifically, the methods and compositions may be used to detect, quantify, inhibit, kill, differentiate, or eliminate cancer stem cells (CSCs) and may be used in the treatment of cancers associated with CSCs, and particularly cancers and CSCs that express LOX1.

13 Claims, 12 Drawing Sheets
Specification includes a Sequence Listing.

Figure 1A-C

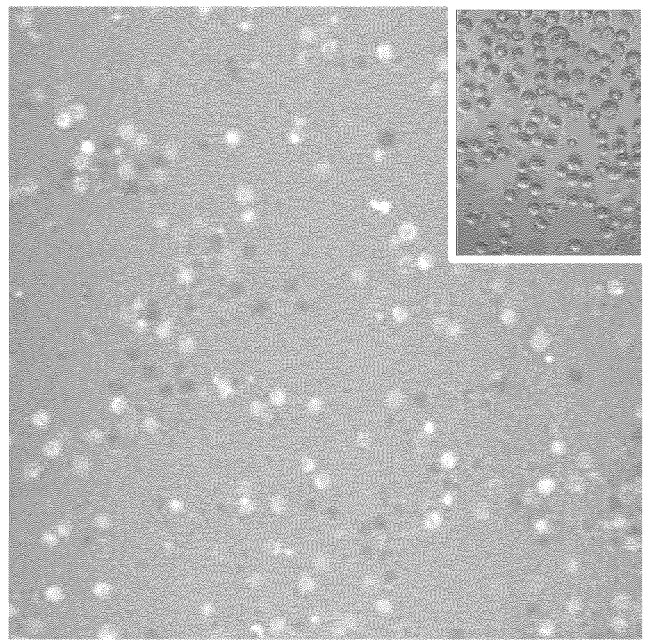
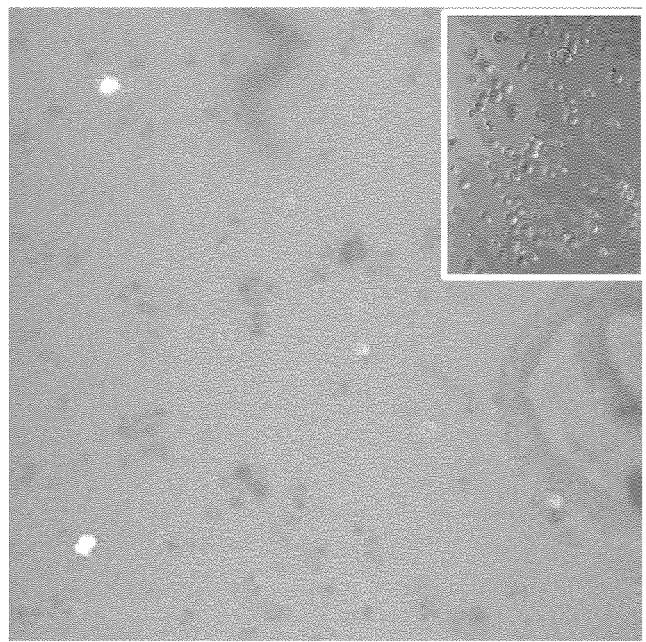
Figure 3A

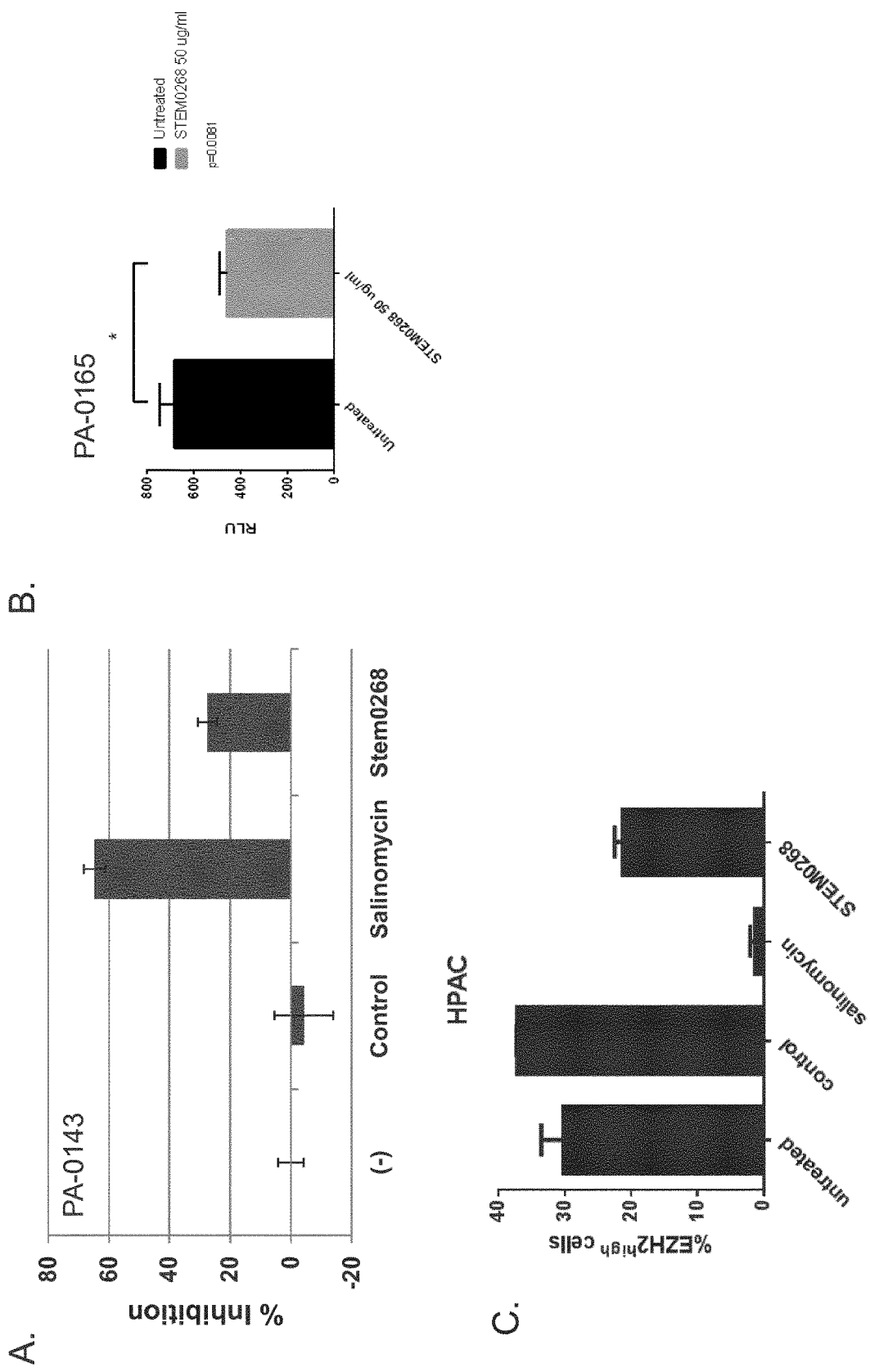
Figure 5 A-C

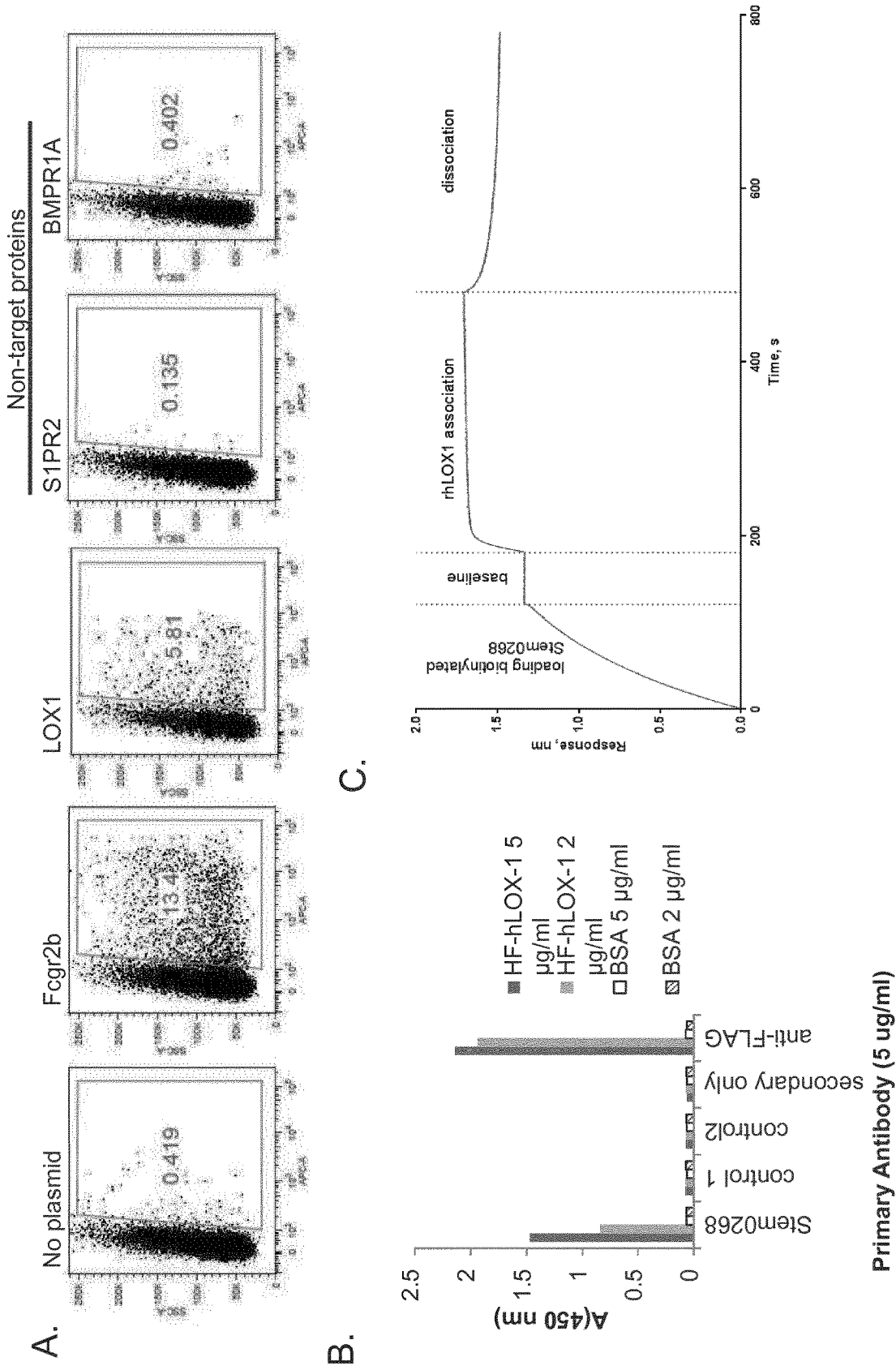
Figure 6 A-C

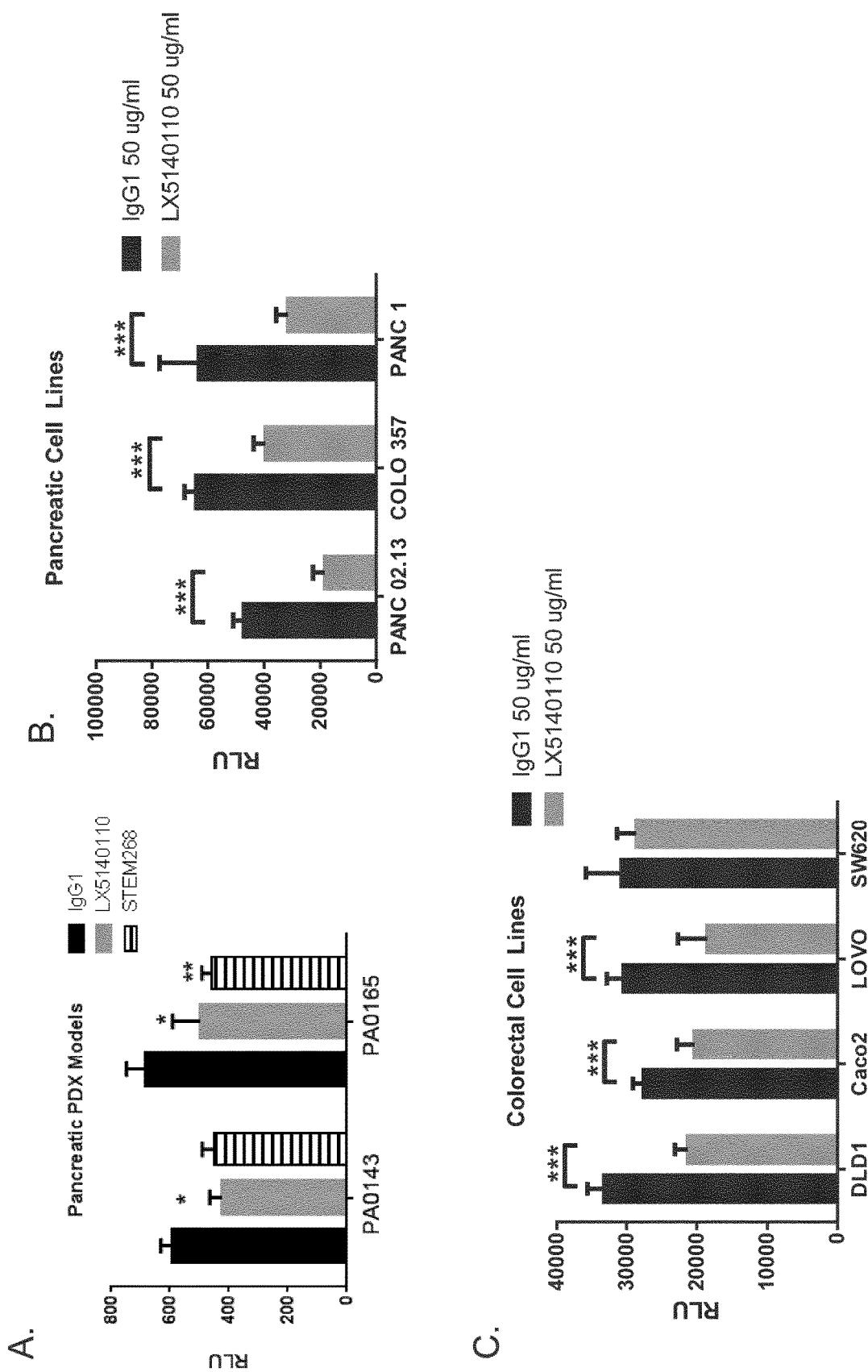
Figure 7 A-C

Figure 8 A-B
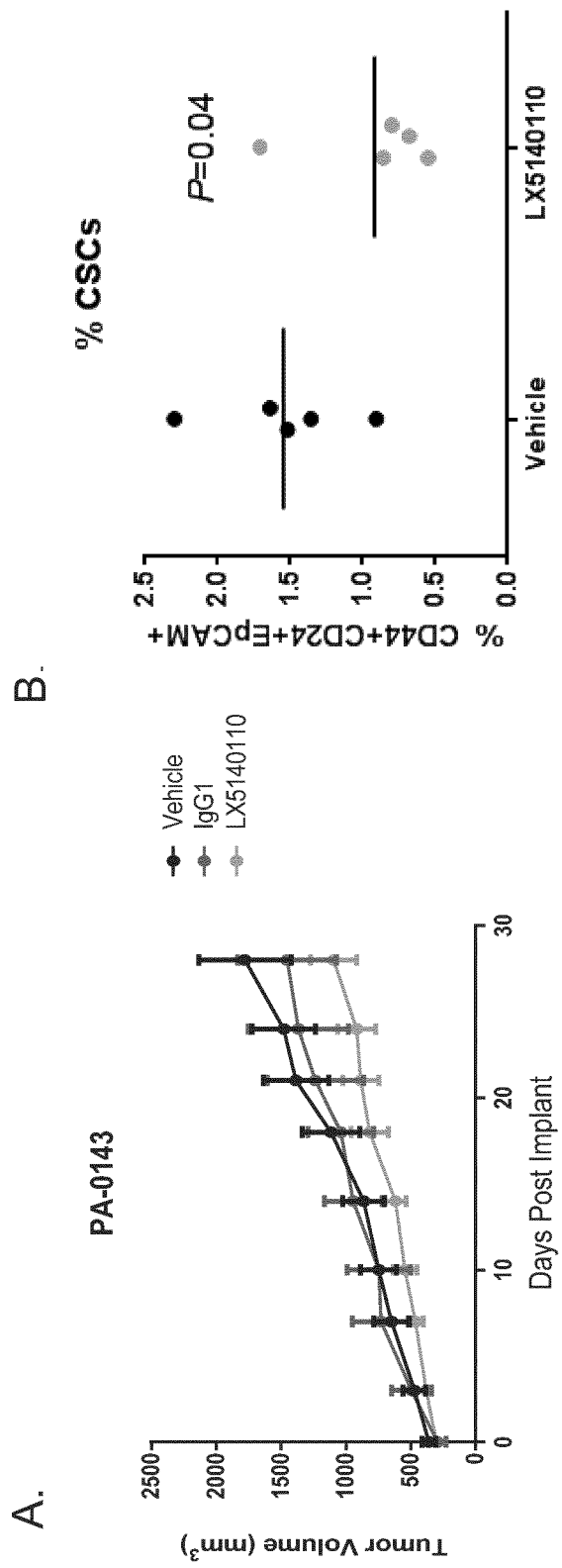

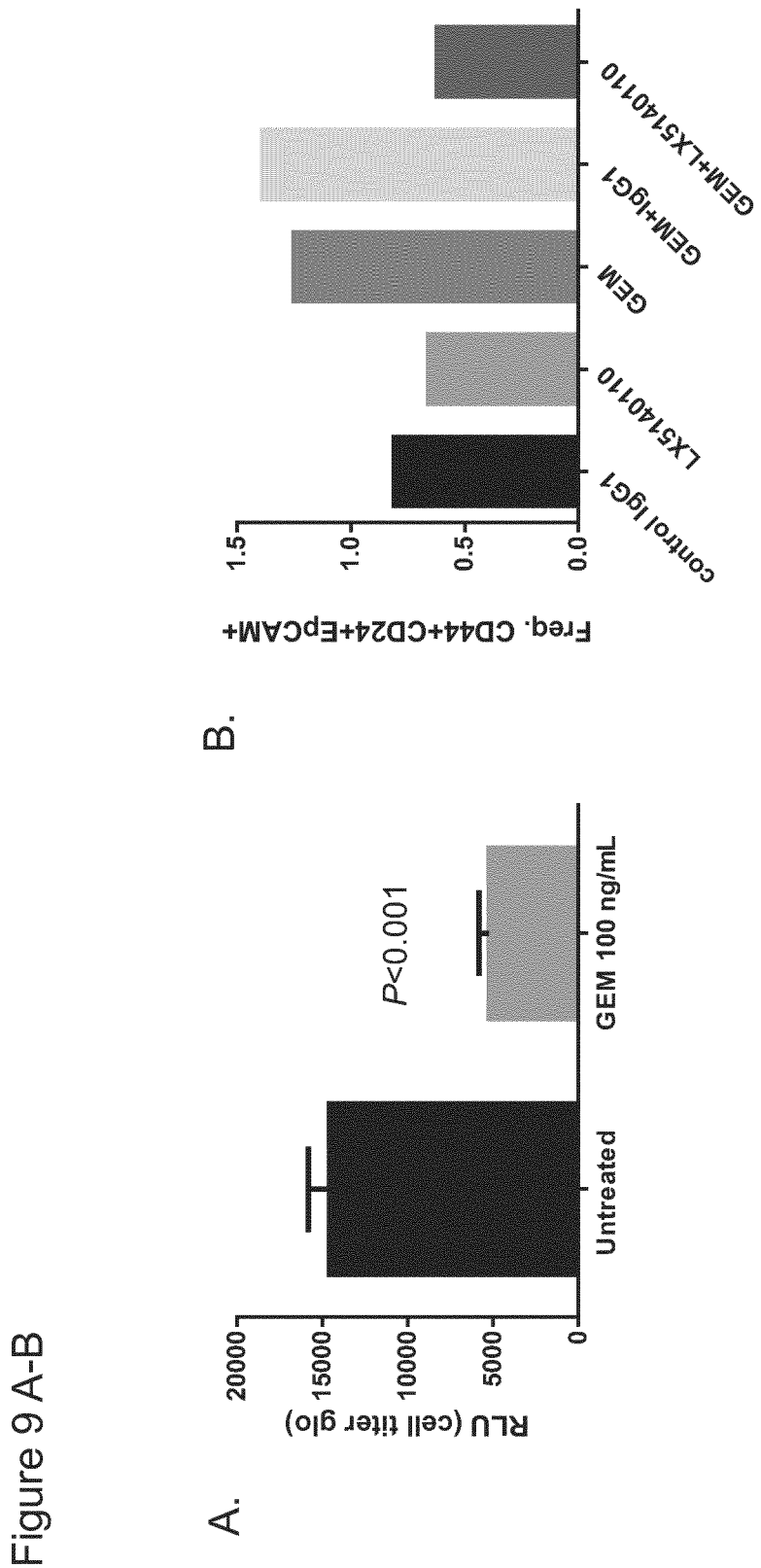
Figure 9 A-B

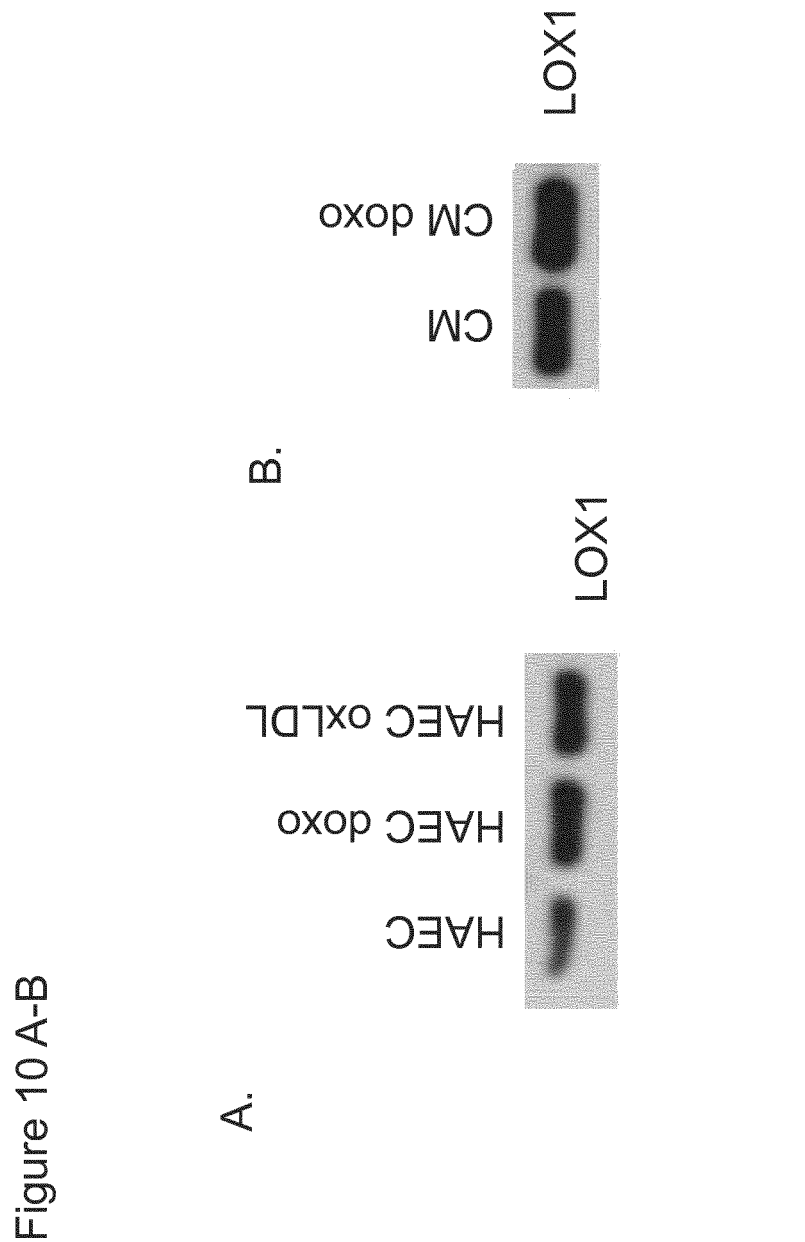
Figure 10 A-B

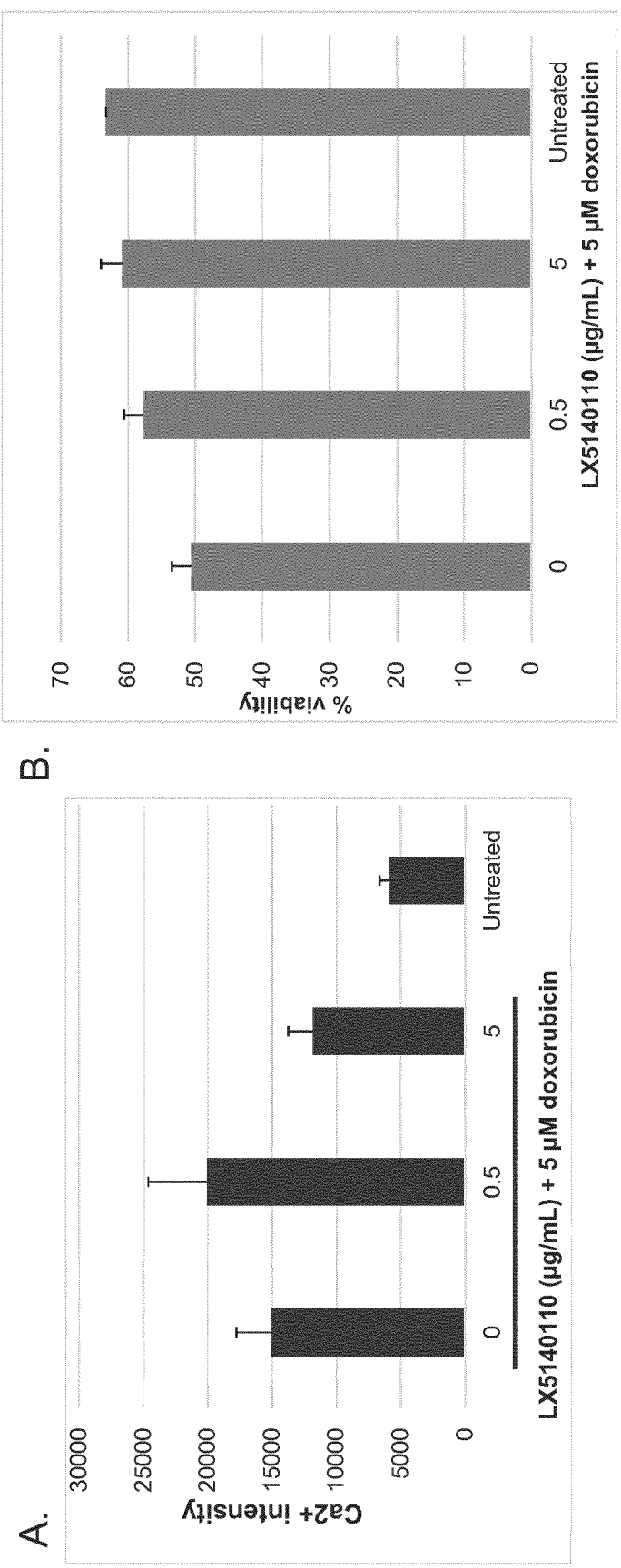
Figure 11 A-B

COMPOSITIONS AND METHODS FOR INHIBITING CANCER STEM CELLS

CROSS-REFERENCE TO RELATED APPLICATIONS

This patent application is a U.S. National Stage application of International Patent Application No. PCT/EP2016/073362, filed on Sep. 29, 2016, said International Patent Application No. PCT/EP2016/073362 claims the benefit of U.S. Provisional Patent Application No. 62/235,144, filed Sep. 30, 2015, which is incorporated by reference herein in its entirety.

REFERENCE TO SEQUENCE LISTING SUBMITTED ELECTRONICALLY

This application incorporates by reference a Sequence Listing submitted with this application in computer readable form (CRF) as a text file entitled "LOX1-200-US-PCT-SequenceListing" created on Mar. 29, 2018 and having a size of 50,116 bytes.

BACKGROUND

While a number of effective treatments are being realized in the fight against some cancers (e.g., childhood leukemia, Hodgkin's disease and testicular cancer) and the death rate for some common cancers (e.g., breast, prostate) has decreased in light of progress made in patient education regarding early detection and prevention, the survival rate for patients with many advanced forms of cancer has not changed significantly for decades. As such, cancer still represents the second-most common cause of death in the United States.

Cancer stem cells (CSCs), as their name implies, are a subset of cancer cells with stem cell like characteristics of pluripotency and unlimited self-renewal. As such, it is believed that this subpopulation of cells is responsible for tumor formation and adaptation to its environment. Several lines of evidence now indicate that CSCs are likely responsible for drug resistance, metastasis, and relapse of cancer, particularly in instances with minimal residual disease. In fact, recent clinical evidence showed that the fraction of breast cancer cells that survived following standard-of-care therapy was enriched in cells bearing a CSC signature (Creighton et al., 2009). In a similar study, patients with 5 q deletion MDS were also found to have residual populations of malignant stem cells in their bone marrow, despite having entered clinical and cytogenetic remission (Tehranchi et al., 2010). In many clinical indications, it is now believed that despite initial therapeutic response, the retention of a distinct subset of resistant cancer cells can lead to relapse and potentially metastasis.

Since their initial identification, cancer stem cells have been discovered and validated in many tumor types. Following the original identification of a CSC in a model of AML (Lapidot et al., 1994), CSCs were discovered and validated in a number of hematological and solid tumor malignancies. The first evidence of CSCs in solid tumors came from breast cancer, where CSCs were found to bear a $CD44^+/CD24^-$ surface marker phenotype (Al-Hajj et al., 2003). CSCs in pancreatic cancer have also been well characterized. While various reports identify pancreatic CSCs as either $Epcam^+/CD44^+/CD24^+$ (Li et al., 2007) or $CD133^+$ (Hermann et al., 2007), others have reported that the triple positive $Epcam^+/CD44^+/CD24^+$ signature tracks best with the tumorigenic phenotype of a CSC (van Vlerken et al., 2013). Reports have identified CSCs in colorectal cancer, and research has identified a stem cell origin in the mouse for intestinal and colorectal tumors (Barker et al., 2009). Nevertheless, the state of the art in this field has not reached a consensus regarding the surface marker phenotype for human CSCs. While many surface markers have been reported, such as CD66 (Gemei et al., 2013), LGR5 (Hirsch et al., 2014), and CD44 and CD133 (Wang et al., 2012), the field lacks any robust confirmation that any of these surface marker phenotypes may represent a consensus for human CSCs, which allows for other techniques such as non-adherent sphere growth (e.g., tumorspheres) to find common use in identifying the presence of CSCs.

While traditional and newly developing anti-cancer therapies (e.g., chemotherapy, radiation, surgery) are evaluated based on their ability to shrink tumors, these therapies may not be effective in inhibiting or killing cancer stem cells, which may lead to cancer recurrence and resistance. Furthermore, because cancer stem cells are linked to metastases, therapies that do not inhibit or kill cancer stem cells may not be effective in prolonged disease treatment or patient survival. Therefore it is of paramount importance that new drugs capable of targeting and eliminating CSC populations be identified and developed, as such drugs are emerging as a critical component of any successful therapy against cancer. Current research is showing that CSCs are responsible for chemoresistance, metastasis, and ultimately relapse of the cancer, even after an initial successful therapeutic intervention. While CSCs are driven by the same major self-renewal pathways that drive pluripotency of embryonic stem cells, knowledge of other cellular pathways that drive CSC activity is still limited.

Accordingly, the availability of additional compositions and methods for treatment of cancers, including methods for reducing tumorigenicity of cancer and inhibiting or killing cancer cells, particularly cancer stem cells (e.g., inducing apoptosis or differentiation), would allow for more therapeutic options and hold the potential for better clinical outcomes such as disease remission and/or improvement of patient quality of life.

SUMMARY OF THE DISCLOSURE

In one aspect, the disclosure relates to a method for inhibiting proliferation of a cancer stem cell (CSC) comprising contacting the CSC with an inhibitor of LOX1 in an amount effective to inhibit proliferation and/or reduce survival of the CSC.

In an aspect, the disclosure relates to a method for treating a therapeutically-resistant cancer in a subject who has previously received a therapy and who is in need of treatment, comprising administering to the subject an inhibitor of LOX1 in an amount effective to inhibit or kill cancer stem cells (CSCs) present in the therapeutically-resistant cancer. In some embodiments, the method may comprise administering to a subject an inhibitor of LOX1 in an amount effective to induce differentiation of cancer stem cells (CSCs) present in the therapeutically-resistant cancer.

In an aspect, the disclosure relates to a method for treating a therapeutically-resistant cancer in a subject who has previously received a therapy and who is in need of treatment, comprising administering to the subject an inhibitor of LOX1 in an amount effective to treat the therapeutically-resistant cancer.

In an aspect, the disclosure relates to a method for treating a cancer that comprises cancer stem cells (CSCs), the method comprising administering to a subject in need of treatment an inhibitor of LOX1 in an amount effective to target and inhibit or kill the CSCs in the cancer. In some embodiments, the method may comprise administering to a subject an inhibitor of LOX1 in an amount effective to induce differentiation of cancer stem cells (CSCs) present in the cancer.

In an aspect, the disclosure relates to a method for treating a cancer that comprises cancer stem cells (CSCs), the method comprising administering to a subject in need of treatment an inhibitor of LOX1 in an amount effective to treat the cancer.

In an aspect, the disclosure relates to a method for treating cancer in a subject who has recurring or relapsed cancer comprising administering to a subject an inhibitor of LOX1 in an amount effective to inhibit or kill CSCs in the cancer. In some embodiments, the method may comprise administering to the subject an inhibitor of LOX1 in an amount effective to induce differentiation of cancer stem cells (CSCs) present in the recurring or relapsed cancer.

In an aspect, the disclosure relates to a method for treating cancer in a subject who has recurring or relapsed cancer comprising administering to a subject an inhibitor of LOX1 in an amount effective to treat the cancer.

In one aspect, the disclosure relates to a method for preventing a recurrence or a relapse of cancer, comprising administering to a subject in need of prevention of recurrence or relapse of cancer an inhibitor of LOX1 in an amount effective to prevent recurrence or relapse of cancer.

In a further aspect, the disclosure relates to a method for reducing the risk of cancer relapse in a subject who has cancer comprising administering to the subject an inhibitor of LOX1 in an amount effective to inhibit or kill CSCs in the cancer, thereby reducing the risk of cancer relapse in the subject. In some embodiments, the method may comprise administering to the subject an inhibitor of LOX1 in an amount effective to induce differentiation of cancer stem cells (CSCs) present in the cancer and reduce the risk of relapse or recurrence of the cancer.

In another aspect, the disclosure relates to a method of eliminating a cancer stem cell (CSC) comprising contacting the CSC with an inhibitor of LOX1 in an amount effective to eliminate the CSC.

In an aspect, the disclosure relates to a method of selectively reducing the number of cancer stem cells (CSCs) in a population of cancer cells comprising contacting the population of cancer cells with an inhibitor of LOX1 in an amount effective to inhibit or kill CSCs in the population of cancer cells. In some embodiments, the method may comprise administering to the subject an inhibitor of LOX1 in an amount effective to induce differentiation of cancer stem cells (CSCs) in the population of cancer cells and reduce the number of CSCs.

In a further aspect, the disclosure provides a method for reducing or inhibiting tumor growth comprising contacting the tumor with an inhibitor of LOX1 in an amount effective to reduce or inhibit tumor growth. In a related aspect, the disclosure provides a method for reducing or inhibiting tumor growth in a patient comprising administering to the patient an inhibitor of LOX1 in an amount effective to reduce or inhibit tumor growth.

In another aspect, the disclosure provides a method for reducing the size of a tumor comprising contacting the tumor with an inhibitor of LOX1 in an amount effective to reduce tumor size. In a related aspect, the disclosure relates to a method for reducing the size of a tumor in a patient comprising administering to the patient an inhibitor of LOX1 in an amount effective to reduce tumor size.

In another aspect, the disclosure provides a method for inhibiting, reducing, or preventing tumor invasiveness or metastasis comprising contacting the tumor with an inhibitor of LOX1 in an amount effective to inhibit, reduce, or prevent tumor invasiveness or metastasis. In a related aspect, the disclosure relates to a method for inhibiting, reducing, or preventing tumor invasiveness or metastasis in a patient comprising administering to the patient an inhibitor of LOX1 in an amount effective to inhibit, reduce, or prevent tumor invasiveness or metastasis.

In another aspect, the disclosure provides a method for inhibiting, reducing, or preventing chemotherapy-associated cardiotoxicity in a patient in need of chemotherapy comprising administering to the patient an inhibitor of LOX1 in an amount effective to inhibit, reduce, or prevent chemotherapy-associated cardiotoxicity. In one embodiment, the chemotherapy is an anthracycline, such as doxorubicin. In one embodiment, the LOX1 inhibitor is a LOX1 antibody.

The disclosure also relates to one or more uses of an inhibitor of LOX1, or a combination thereof in a composition, including therapeutic and pharmaceutical compositions. In embodiments, the uses and compositions comprise the inhibitor(s) in amounts effective to provide for the various methods disclosed herein. In embodiments, the one or more uses relate to uses for the manufacture of a medicament for treating (e.g., killing, eliminating, inhibiting, reducing the progression and/or rate of progression of cell proliferation, reducing the progression and/or rate of progression of a disease state, reducing the ability for self-renewal and expansion (e.g., inducing differentiation)) one or more of the tumors, cancer stem cells, and/or cancers described herein.

In another aspect, the disclosure provides methods for diagnosis, prognosis, quantification, identification, and/or detection of the presence of a cancer stem cell (CSC) in a sample comprising cancer cells, wherein the method comprises:

contacting the sample with an agent that binds to a LOX1 nucleic acid sequence or a LOX1 amino acid sequence;

detecting the presence or absence of binding between the agent and the LOX1 nucleic acid sequence or the LOX1 amino acid sequence; and identifying the presence of the CSC in the sample upon detection of binding between the agent and the LOX1 nucleic acid sequence or the LOX1 amino acid sequence.

In embodiments of this aspect, the method can further comprise one or more of:

quantifying the amount of the LOX1 nucleic acid sequence or the LOX1 amino acid sequence in the sample;

comparing the amount of the LOX1 nucleic acid sequence or the LOX1 amino acid sequence to a reference level of LOX1 nucleic acid or LOX1 amino acid; and/or identifying the presence of the CSC in the sample when the detected amount is greater than the reference level.

In yet further embodiments, the method may comprise an agent comprising a detectable moiety. In some embodiments, the agent may comprise a nucleic acid sequence that hybridizes to at least a portion of a LOX1 nucleic acid sequence (e.g., mRNA, cDNA, etc.) under stringent hybridization conditions. In some embodiments, the agent may comprise an antibody that specifically binds to at least a portion of the LOX1 amino acid sequence.

In various embodiments of the above aspects, the methods relate to a tumor and/or a CSC, or a population of CSCs that express LOX1. In further embodiments, the tumor and/or a CSC, or a population of CSCs may comprise sphere-forming CSCs.

In various embodiments of the above aspects, the methods relate to a tumor and/or a cancer selected from colorectal cancer, pancreatic cancer, lung cancer, head and neck cancer, gastric cancer, hepatocellular carcinoma, adrenal cancer, leukemia, melanoma, myeloma, prostate cancer, thyroid cancer, and breast cancer.

The aspects and embodiment described herein relate to methods that comprise an inhibitor of LOX1, a combination of inhibitors of LOX1, and/or other cancer therapeutics. In some embodiments the inhibitor comprises an antibody that binds LOX1, a small molecule inhibitor of LOX1, a siRNA that hybridizes to a nucleic acid encoding LOX1, or any combinations thereof.

The above aspects and embodiment also relate to methods, uses, and compositions that further comprise an additional therapy for treatment or management of diseases relating to angiogenesis, tumorigenesis, and cancers and can include a therapeutic regimen such as, for example, a chemotherapy, a radiotherapy, an immunotherapy, or any other active agent or therapy that is known in the art.

Other aspects will be apparent to one of skill in the art upon review of the description and exemplary depictions that follow.

BRIEF DESCRIPTION OF THE DRAWINGS

For the purpose of illustrating the disclosure, there are depicted in the drawings certain aspects of the disclosure. However, the disclosure is not limited to the precise arrangements and instrumentalities of the aspects depicted in the drawings.

FIG. 3A-3B shows binding of a DARPin (STEM0268) to pancreatic CSCs but not normal cells. (A) STEM0268 binds to FACS isolated (sorted by CD24$^+$, CD44+, EpCAM+) pancreatic CSCs (right panel) but not to normal pancreatic epithelial cells (left panel). Insets show a brighter field image of the cells analyzed by FMAT for binding. (B) Lane 1 is anti-EpCAM; Lane 2 is anti-MHC1-AF488; Lane 3 is cells+viability dye; Lane 4 is E-3-5; Lane 5 is DARPin STEM 0268; Lane 6 is unstained cells. STEM0268 does not bind to normal bronchial epithelial or colon epithelial cells and shows minimal binding to renal epithelial cells.

FIG. 5A-5C shows that STEM0268, inhibits pancreatic CSCs. STEM0268 shows inhibition of sphere formation in both PA-0143 (A) and in PA-0165 (B). STEM0268 also inhibits CSCs in the HPAC cell line as measured by the number of EZH2$^{high}$ cells (Control=irrelevant DARPin control). Experiments shown in 5A and 5C also used Salinomycin (1 µM) as a positive control.

FIG. 6A-6C depict experiments identifying LOX1 as the target of STEM0268. (A) FACS analysis of HEK293 overexpressing different proteins. The middle panel shows binding of STEM0268 to LOX1-expressing cells. Controls included no plasmid and cells overexpressing FcγR2b ("Fcgr2b"). Examples of STEM0268 binding to HEK293 cells expressing non-target proteins (S1PR2 and BMPR1A) are shown. (B) An ELISA with flag-tagged recombinant human LOX1 shows binding of STEM0268. Controls include two DARPin-Fc that do not bind to human proteins (control 1 and 2) as well as an anti-FLAG antibody and secondary antibody alone. (C) Octet binding of STEM0268 to recombinant human LOX1.

FIG. 7A-7C demonstrates inhibition of CSCs by a LOX1 inhibitor in multiple models. (A) A similar level of inhibition of CSCs by a LOX1 monoclonal antibody, LX5140110, as compared to the DARPin STEM0268 in the pancreatic PDX models utilized in FIG. 5A and FIG. 5B. LX5140110 inhibits CSCs in additional pancreatic cell lines (B), as well as in colorectal cell lines (C).

FIG. 8A-8B depicts the inhibition of CSCs in vivo by LX5140110 in pancreatic cancer. (A) LX5140110 leads to a modest decrease in growth of PA0143, as anticipated, when specifically targeting a small percentage of CSCs within a tumor model. P<0.0001 Tukey's multiple comparison test, LX5140110 as compared with either vehicle and IgG1 treated arms. (B) CSCs are reduced in PA0143 following treatment with LX5140110.

FIG. 9A-9B demonstrates that the combination of LX5140110 and gemcitabine is capable of inhibiting CSCs. (A) The Pan02.13 pancreatic cell line growth is inhibited by gemcitabine (GEM). (B) Treatment with Pan02.13 with gemcitabine leads to an increase of CSCs in Pan02.13, which can be reversed by LX5140110 but not a non-specific control IgG1.

FIG. 10A-10B shows that doxorubicin can increase LOX1 expression. (A) Human aortic endothelial cells treated with doxorubicin show increased expression of LOX1. Oxidized LDL (oxLDL) was used as a control. (B) Cardiomyocytes treated with doxorubicin also show an increase in LOX1 expression.

FIG. 11A-11B depicts the cardiomyocyte damage induced by doxorubicin and the ability of LX5140110 to reverse the damage. (A) Cardiomyocytes treated with doxorubicin (DOX) have increased calcium levels showing cardiomyocyte dysfunction. These levels are reversed by LX5140110. (B) Cardiomyocytes treated with DOX show decreased viability, while those pretreated with LX5140110 show increased cell viability.

DETAILED DESCRIPTION

Figure 1:
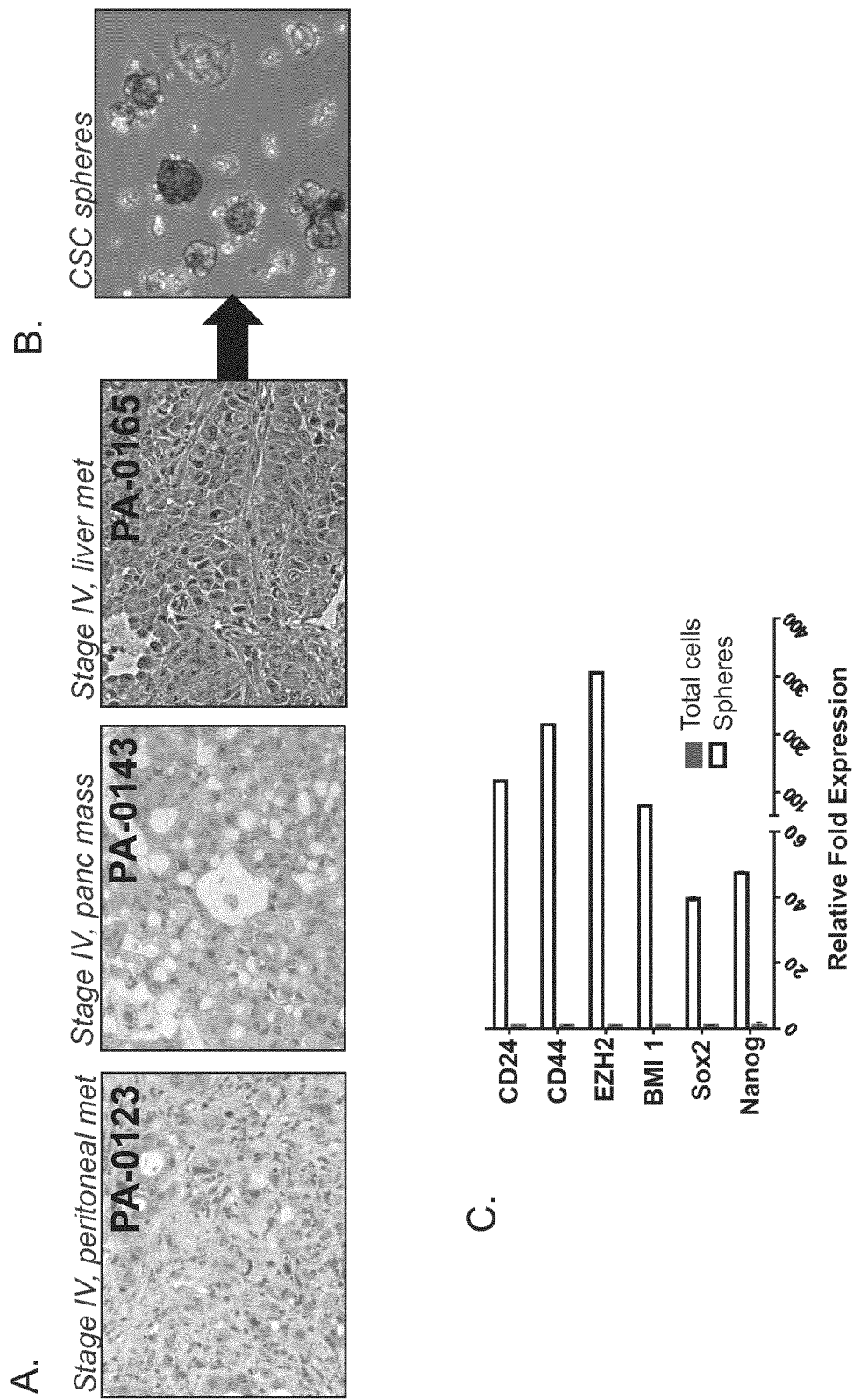
FIG. 1A-1C shows enrichment of CSCs from pancreatic PDX models. (A) H&E stains of three pancreatic PDX models derived from late stage and metastatic pancreatic cancer. (B) Tumorspheres generated from the PDX models shown in A. (C) Tumorspheres were analyzed at day 4 for the expression of both the surface markers indicative of pancreatic CSCs (CD24 and CD44) as well as genes identified as maintaining a CSC state (EZH2, BMI1, Sox2 and Nanog).

The invention described herein demonstrates, for the first time, that Lectin-like oxidized low density lipoprotein receptor-1 (LOX1) is overexpressed by and is a functionally relevant therapeutic target in CSCs. While reports have referred to potential LOX1 expression in some cancers, no reports have identified LOX1 expression and function to any CSC phenotype, which provides for new and unexpected methods for treating cancer, cancer metastasis, and particularly inhibiting CSCs. As illustrated in certain aspects and non-limiting embodiments disclosed herein, the novel methods that target and inhibit LOX1 activity are useful and effective against cancers that comprise and exhibit cells having a CSC phenotype. In some illustrative embodiments, the methods and agents disclosed herein may be used to target cancers comprising CSC cells that express LOX1 including, for example, pancreatic cancer, colorectal cancer, hepatocellular carcinoma, gastric cancer, lung cancer, head and neck cancer, and breast cancer. Thus, the disclosure provides for novel targeting strategies that include methods and agents that inhibit CSCs and can be used to inhibit and/or treat various cancers in patients suffering from cancer and improve quality of life.

LOX1 is a disulphide linked type II transmembrane protein. It was first identified as a major receptor of oxidized low density lipoprotein (oxLDL) (Kume et al., 1997). The receptor consists of a short N terminal cytoplasmic domain, transmembrane domain, neck domain and a C-type lectin domain (CTLD), with the structure of the CTLD has been solved (Ohki et al., (2005)). In addition, LOX1 can be proteolytically cleaved in the neck domain releasing soluble LOX1 (sLOX1). LOX1 is a class E scavenger receptor and binds multiple ligands including oxLDL, C-reactive protein (CRP), phosphatidylserine, advanced glycation end products (AGEs), small dense lipoproteins (sdLDL), oxidized HDL, N4-oxononanoyl lysine (ONL), heat shock proteins (hsp), *Chlamydia pneumoniae*, platelets, leukocytes and apoptotic cells. Many of these ligands, particularly oxLDL, are associated with atherosclerosis. Multiple signal transduction pathways are associated with LOX1 activation including RhoA/Rac1, nitrogen monoxide, p38MAPK, protein kinase B and C, ERK1/2, and NFκB. See, e.g., Taye et. al., *Eur J Clin Invest.* 43(7):740-5 (2013).

Preclinical evidence implicates LOX1 in the promotion of vascular dysfunction, plaque progression, rupture and thrombosis, atherosclerosis and inflammatory conditions. See, e.g., Ulrich-Merzenich et al., (2013). For example, whereas LOX1 knockout mice have reduced aortic atherosclerosis and decreased vessel wall collagen deposition (Mehta et al., (2007)), LOX1 overexpression increased atherosclerotic plaque formation (Inoue et al., (2005); and White et al., (2011)) with LOX1 expression observed on the vulnerable plaque shoulders and associated with macrophage accumulation, apoptosis, and MMP-9 expression (Li et al., (2010)). Neutralizing LOX1 antibodies restored acetylcholine induced coronary arteriolar dilation (Xu et al., (2007)) and reduced intimal thickening after balloon injury in rats (Hinagata et al., (2006)). LOX1 expression in humans is not constitutive but dynamically inducible by proinflammatory stimuli. In the atherosclerotic plaque LOX1 is expressed on endothelial cells, smooth muscle cells and macrophages. Interestingly serum sLOX1 has been proposed to be diagnostic of plaque instability and rupture in acute coronary syndrome (ACS) patients (Nakamura et al., (2010)); to be predictive of ACS recurrence or death (Kume et al., (1997)); and is associated with increasing number of complex lesions (Zhao et al., (2011)).

In addition to the above, LOX1 has been shown to have increased expression in several cancer types, such as prostate cancer (Fangning Wan et al. (2015)). It has also been reported that high protein expression levels, in combination with high body weight index, could predict a poor prognosis in squamous non-small cell lung cancer (Long et al., (2015)). LOX1 has also been reported to be involved in transforming a normal breast epithelial cell line (MCF10A) into a tumorigenic cell line through the activation of NF-kB and speculate regarding any involvement in cell proliferation and migration (Khaidakov M et al., (2011) and Hirsh H A et al. (2010)). While these reports discuss potential roles LOX1 may play in several cancers, the disclosure provided herein is believed to be the first evidence that LOX1 plays a role in CSC biology.

This disclosure includes a description and overview of the identification of LOX1 as a novel target for CSCs. As referred to herein, the determination of LOX1 as a relevant CSC target is discussed by way of illustrative examples that incorporate a phenotypic selection and analysis of patient-derived xenograft (PDX) models obtained from pancreatic cancers. The PDX models were enriched for CSCs by generating tumorspheres and, through the screening process discussed in the Examples, inhibitors of LOX1 can be utilized to inhibit CSCs (e.g., inhibit proliferation, induce differentiation, induce CSC apoptosis, or otherwise kill or slow progression of CSC proliferation).

Thus, LOX1 plays a role in CSC growth and activity, which is entirely novel to CSC biology. The disclosure provides illustrative embodiments demonstrating that CSCs such as, for example CSCs derived from pancreatic cancer models, express LOX1, and that in turn LOX1 can influence CSC self-renewal and proliferation. Strategies that include neutralizing LOX1 activity with a LOX1 inhibitor such as, for example, a monoclonal antibody may provide a significant effect on CSC inhibition, supporting the great potential for therapies targeting LOX1 to reduce CSCs in the tumor.

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise. Further, these terms as well as the terms "one or more," and "at least one" can be used interchangeably herein.

Furthermore, "and/or" is to be taken as specific disclosure of each of the two specified features or components with or without the other. Thus, the term "and/or" as used in a phrase such as "A and/or B" is intended to include "A and B," "A or B," "A" (alone), and "B" (alone) Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

Wherever aspects are described with the language "comprising," otherwise analogous aspects described in terms of "consisting of" and/or "consisting essentially of" are also provided.

The terms "about" and "approximately" in the context of the present invention denote an interval of accuracy that a person skilled in the art will understand to still ensure the technical effect of the feature in question. The term typically encompasses a deviation from the indicated numerical value of about +/−10%, or about +/−5%.

The determination of percent identity between two sequences is preferably accomplished using the mathematical algorithm of Karlin and Altschul (1993) Proc. Natl. Acad. Sci USA 90: 5873-5877. Such an algorithm is e.g. incorporated into the BLASTn and BLASTp programs of Altschul et al. (1990) J. Mol. Biol. 215: 403-410 available at the NCBI website. The determination of percent identity is preferably performed with the standard parameters of the BLASTn and BLASTp programs.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "LOX1" and "Lectin-like oxidized low density lipoprotein receptor-1" are used interchangeably herein and refer to LOX1 and/or biologically active fragments of LOX1. The cDNA and amino acid sequences of three hLOX1 isoforms are provided at GenBank Acc. Nos.: NP_002534.1, NP_001166103.1, and NP_001166104.1, each of which is incorporated herein by reference in its entirety.

The terms "inhibit," "block," "reduce," and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in LOX1 biological activity. Accordingly, when the terms "inhibition" or "suppression" are applied to describe for example, an effect on a LOX1-mediated signal transduction pathway in a cell expressing cell surface LOX1 (e.g., a CSC) and in the presence of a LOX1 ligand (e.g., oxLDL, CRP and AGEs), the terms refer to the ability of a LOX1-binding protein, e.g., an anti-LOX1 antibody, to decrease a LOX1-mediated induced signal transduction in the cell at a statistically significant level (e.g., with a p value less than or equal to 0.05). In additional aspects, the inhibited or blocked LOX1-mediated biological activity provides programmed cell death (i.e., apoptosis). In further embodiments, the inhibited or blocked LOX1-mediated biological activity provides differentiation of cells (e.g., CSCs).

The terms "antibody" or "immunoglobulin," as used interchangeably herein, include whole antibodies and any antigen-binding fragment or single chains thereof. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, Cl. The VH and VL regions can be further subdivided into regions of hypervariablity, termed Complementarity Determining Regions (CDRs), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include typical antibodies, scFvs, and combinations thereof where, for example, an scFv is covalently linked (for example, via peptidic bonds or via a chemical linker) to the N-terminus of either the heavy chain and/or the light chain of a typical antibody, or intercalated in the heavy chain and/or the light chain of a typical antibody.

The term "antibody" can refer to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. The term "antibody" includes monoclonal antibodies, recombinant antibodies, human antibodies, humanized antibodies, chimeric antibodies, bi-specific antibodies, multi-specific antibodies, or antibody fragments thereof.

The term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules such as toxins, radioisotopes, etc.

The term "germlining" means that amino acids at specific positions in an antibody are mutated back to those amino acids occurring at the same position as found in the germ line.

The term "antigen-binding antibody fragment" or "LOX1-binding antibody fragment" refers to a portion of an intact antibody and refers to the complementarity determining variable regions of an intact antibody. Examples of antibody fragments include, but are not limited to Fab, Fab', F(ab')2, and Fv fragments, linear antibodies, single chain antibodies (e.g., ScFvs), and multispecific antibodies formed from antibody fragments. The disclosure further provides LOX1-binding antibody fragments wherein the antibody fragment is a Fab fragment, a Fab' fragment, a $F(ab')_2$ fragment, a Fv fragment, a diabody, or a single chain antibody molecule.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., Nature, 321:522-525 (1986); Riechmann et al., Nature, 332:323-327 (1988); Verhoeyen et al., Science, 239:1534-1536 (1988)). In some instances, the Fv framework region (FW) residues of a human immunoglobulin are replaced with the corresponding residues in an antibody from a non-human species that has the desired specificity, affinity, and capability.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FW) connected by three complementarity-determining regions (CDRs) also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., J. Molec. Biol. 273:927-948 (1997)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991) herein incorporated by reference). The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See, e.g., Lefranc, M. P. et al., Dev. Comp. Immunol. 27: 55-77 (2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, etc.) with the desired specificity, affinity, and capability while the constant regions are homologous to the sequences in antibodies derived from another (usually human) to avoid eliciting an immune response in that species.

The terms "TM" or "TM mutant" refer to a mutation in the IgG1 constant region that results in a decreased effector function (e.g., ADCC) of an antibody having the mutation. A TM mutant comprises a combination of three mutations L234F/L235E/P331S resulting in an effector null human IgG1 (EU numbering Kabat et al. (1991) Sequences of Proteins of Immunological Interest, U.S. Public Health Service, National Institutes of Health, Washington, D.C.), introduced into the heavy chain of an IgG1.

The terms "YTE" or "YTE mutant" refer to a mutation in IgG1 Fc that results in an increase in the binding to human FcRn and improves the serum half-life of the antibody having the mutation. A YTE mutant comprises a combination of three mutations, M252Y/S254T/T256E (EU numbering Kabat et al. (1991) Sequences of Proteins of Immunological Interest, U.S. Public Health Service, National Institutes of Health, Washington, D.C.), introduced into the heavy chain of an IgG1. See U.S. Pat. No. 7,658,921, which is incorporated by reference herein. The YTE mutant has been shown to increase the serum half-life of antibodies approximately four-times as compared to wild-type versions of the same antibody (Dall'Acqua et al., *J. Biol. Chem.* 281:23514-24 (2006)). See also U.S. Pat. No. 7,083,784, which is incorporated by reference herein in its entirety.

The terms "LOX1-binding protein", "anti-LOX1 antibody," or "an antibody that specifically binds LOX1" refer to a LOX1-binding protein such as an anti-LOX1 antibody that is capable of binding LOX1 with sufficient affinity such that the antibody is useful as a therapeutic agent or diagnostic reagent in targeting LOX1. The extent of binding of an anti-LOX1 antibody to an unrelated, non-LOX1 protein is less than about 10% of the binding of the antibody to LOX1 as measured, e.g., by a radioimmunoassay (RIA), BIACORE® (using recombinant LOX1 as the analyte and antibody as the ligand, or vice versa), Kinetic Exclusion Assay (KINEXA®), or other binding assays known in the art. In certain aspects, the LOX1-binding protein is a full-length antibody or a LOX1-binding antibody fragment that has a dissociation constant (KD) of ≤1 nM, ≤0.5 nM, ≤0.1 nM, ≤10 pM, or ≤1 pM, or in some instances, a KD of about 150 pM to about 600 pM or about 400 pM to about 600 pM. In certain aspects, the LOX1-binding protein is a full-length antibody or a LOX1-binding antibody fragment that has a dissociation constant (KD) of ≤1 µM, ≤100 nM, ≤10 nM, ≤1 nM, ≤0.1 nM, ≤10 pM, ≤1 pM, or ≤0.1 pM, or in some instances, a KD of about 150 pM to about 600 pM.

An "antagonist" or "blocking" LOX1-binding protein is one that inhibits or reduces the biological activity of LOX1. In some aspects, the antagonist LOX1-binding protein inhibits the ability of LOX1 to bind oxLDL, AGEs, and/or CRP. In some aspects, the LOX1-binding protein inhibits the ability of LOX1 to bind oxHDL, HSP60, leukocytes and/or activated platelets. In certain aspects a LOX1-binding protein substantially or completely inhibits the biological activity of LOX1. Desirably, the LOX1 biological activity is reduced by 10%, 20%, 30%, 50%, 70%, 80%, 90%, 95%, or even 100%. In particular aspects, the LOX1-binding protein is an anti-LOX1 antibody, such as a full length antibody or a LOX1-binding antibody fragment. In further aspects, the anti-LOX1 antibody inhibits or reduces the biological activity of LOX1 by 10%, 20%, 30%, 50%, 70%, 80%, 90%, 95%, or even 100%.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

"Potency" is normally expressed as an $IC_{50}$ value, in nM or pM unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by means known in the art.

The fold improvement in potency for the LOX1-binding protein disclosed herein (e.g., an antibody such as, a full length LOX1-antibody and a LOX1-binding antibody fragment, and variants and derivatives thereof) as compared to a reference antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A LOX1-binding protein (e.g., a LOX1 antibody, including an antigen-binding fragment, variant, and derivative thereof), polynucleotide, vector, cell, or composition that is "isolated" is a polypeptide, antibody, polynucleotide, vector, cell, or composition that is in a form not found in nature. Isolated polypeptides (e.g., anti-LOX1 antibodies including full-length antibodies and LOX1-binding antibody fragments), polynucleotide, vector, polynucleotides, vectors, cells or compositions include those which have been purified to a degree that they are no longer in a form in which they are found in nature. In some aspects, an antibody, polynucleotide, vector, cell, or composition that is isolated is substantially pure.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

A. Methods

The disclosure provides a number of aspects and embodiments relating to methods that incorporate an inhibitor of LOX1. As discussed herein, these aspects and embodiments encompass various methods relating to disease, including methods of treatment, methods of prevention, methods of inhibition and/or slowing progression, methods of reducing risk of relapse and/or recurrence of disease; methods of targeting and/or killing particular cell populations; methods of inducing differentiation and/or reducing the self-renewal and expansion capacity of CSCs; methods of detecting, diagnosing, and/or quantifying particular cell populations and/or diseases, including determining disease stage, and methods of disease monitoring and/or prognosis.

In embodiments, the disclosure provides a method for inhibiting proliferation of a cancer stem cell (CSC) comprising contacting the CSC with an inhibitor of LOX1 in an amount effective to inhibit proliferation and/or reduce survival of the CSC. In embodiments, the method comprises administering an effective amount of a LOX1 inhibitor that is selective for LOX1. In some embodiments the inhibitor selectively inhibits a LOX1 biochemical cascade. The term "selective" when used in connection with the terms "inhibitor" or "inhibits" relates to a compound (e.g., a small molecule or biological molecule as described herein) that has increased inhibitory activity for a target (e.g., LOX1), relative to the inhibitory activity for other biomolecules. In one embodiment, the method includes administration of a therapeutically effective amount of an inhibitor of LOX1 in combination with an additional anti-cancer agent.

In embodiments, the disclosure relates to a method for treating a therapeutically-resistant cancer in a subject who has previously received a therapy and who is in need of treatment, comprising administering to the subject an inhibitor of LOX1 in an amount effective to inhibit or kill cancer stem cells (CSCs) and/or induce differentiation in CSCs present in the therapeutically-resistant cancer. In one embodiment, the previous therapy is radiation, surgery, immunotherapy, chemotherapy, and/or a tyrosine kinase inhibitor.

In further embodiments, the disclosure relates to a method for treating a therapeutically-resistant cancer in a subject who has previously received a therapy and who is in need of treatment, comprising administering to the subject an inhibitor of LOX1 in an amount effective to treat the therapeutically-resistant cancer. In one embodiment, the previous therapy is radiation, surgery, immunotherapy, chemotherapy, and/or a tyrosine kinase inhibitor.

In other embodiments, the disclosure relates to a method for treating a cancer that comprises cancer stem cells (CSCs), the method comprising administering to a subject in need of treatment an inhibitor of LOX1 in an amount effective to target and inhibit or kill the CSCs and/or induce differentiation in CSCs in the cancer. In one embodiment, the method includes administration of a therapeutically effective amount of an inhibitor of LOX1 in combination with an additional anti-cancer agent.

In other embodiments, the disclosure relates to a method for treating a cancer that comprises cancer stem cells (CSCs), the method comprising administering to a subject in need of treatment an inhibitor of LOX1 in an amount effective to treat the cancer. In one embodiment, the method includes administration of a therapeutically effective amount of an inhibitor of LOX1 in combination with an additional anti-cancer agent.

In further embodiments, the disclosure relates to a method for treating cancer in a subject who has recurring or relapsed cancer comprising administering to a subject an inhibitor of LOX1 in an amount effective to inhibit or kill CSCs and/or induce differentiation in CSCs in the cancer. In one embodiment, the method includes administration of a therapeutically effective amount of an inhibitor of LOX1 in combination with an additional anti-cancer agent.

In further embodiments, the disclosure relates to a method for treating cancer in a subject who has recurring or relapsed cancer comprising administering to a subject an inhibitor of LOX1 in an amount effective to treat the cancer. In one embodiment, the method includes administration of a therapeutically effective amount of an inhibitor of LOX1 in combination with an additional anti-cancer agent.

Other embodiments of the disclosure relate to a method for preventing a recurrence or a relapse of cancer, comprising administering to a subject in need of prevention of recurrence or relapse of cancer an inhibitor of LOX1 in an amount effective to prevent recurrence or relapse of cancer. In one embodiment, the method includes administration of a therapeutically effective amount of an inhibitor of LOX1 in combination with an additional anti-cancer agent.

In further embodiments, the disclosure relates to a method for reducing the risk of cancer relapse in a subject who has cancer comprising administering to the subject an inhibitor of LOX1 in an amount effective to inhibit or kill CSCs and/or induce differentiation in CSCs in the cancer, thereby reducing the risk of cancer relapse in the subject. In one embodiment, the method includes administration of a therapeutically effective amount of an inhibitor of LOX1 in combination with an additional anti-cancer agent.

In other embodiments, the disclosure relates to a method of eliminating a cancer stem cell (CSC) comprising contacting the CSC with an inhibitor of LOX1 in an amount effective to eliminate the CSC. In one embodiment, the method includes administration of a therapeutically effective amount of an inhibitor of LOX1 in combination with an additional anti-cancer agent.

In some embodiments, the disclosure relates to a method of selectively reducing the number of cancer stem cells (CSCs) in a population of cancer cells comprising contacting the population of cancer cells with an inhibitor of LOX1 in an amount effective to inhibit or kill CSCs and/or induce differentiation in CSCs in the population of cancer cells. Thus, the inhibitors may be administered to a subject in need of treatment and/or contacted with a number of CSCs in an amount sufficient to prohibit further proliferation of the CSCs. In some embodiments, the inhibitors may be administered in an amount effective to reduce the number of CSCs by inducing cell death (apoptosis) in the population of CSCs. In yet other embodiments, the inhibitors may be administered in an amount effective to reduce the number of CSCs by inducing cellular differentiation in the population of CSCs. Accordingly, in some embodiments the inhibitor(s) is provided in amounts that may not necessarily induce apoptosis in the CSCs, but in amounts that are effective to reduce or deregulate the ability of CSCs to self-renew and expand the CSC cell population in a subject or a tumorigenic tissue by inducing differentiation of the CSCs. The inhibitors may also be provided in an amount that is effective to perturb a CSC "niche" such that the CSC niche is no longer able to maintain CSC and/or tumor tissue regeneration. In one embodiment, the method includes administration of a therapeutically effective amount of an inhibitor of LOX1 in combination with an additional anti-cancer agent.

In some embodiments, the disclosure provides a method for reducing or inhibiting tumor growth comprising contacting the tumor with an inhibitor of LOX1 in an amount effective to reduce or inhibit tumor growth. In a related aspect, the disclosure provides a method for reducing or inhibiting tumor growth in a patient comprising administering to the patient an inhibitor of LOX1 in an amount effective to reduce or inhibit tumor growth. In one embodiment, the method includes administration of a therapeutically effective amount of an inhibitor of LOX1 in combination with an additional anti-cancer agent.

In further embodiments, the disclosure provides a method for reducing the size of a tumor comprising contacting the tumor with an inhibitor of LOX1 in an amount effective to reduce tumor size. In a related aspect, the disclosure relates to a method for reducing the size of a tumor in a patient comprising administering to the patient an inhibitor of LOX1 in an amount effective to reduce tumor size. In one embodiment, the method includes administration of a therapeutically effective amount of an inhibitor of LOX1 in combination with an additional anti-cancer agent.

In some embodiments, the disclosure provides a method for inhibiting, reducing, or preventing tumor invasiveness or metastasis comprising contacting the tumor with an inhibitor of LOX1 in an amount effective to prevent, reduce, or inhibit tumor invasiveness or metastasis. In a related aspect, the disclosure provides a method for inhibiting, reducing, or preventing tumor invasiveness or metastasis in a patient comprising administering to the patient an inhibitor of LOX1 in an amount effective to prevent, reduce, or inhibit tumor invasiveness or metastasis. In one embodiment, the method includes administration of a therapeutically effective amount of an inhibitor of LOX1 in combination with an additional anti-cancer agent.

In embodiments provided by the disclosure, the methods relate to a tumor and/or a CSC, or a population of CSCs expressing LOX1. In further embodiments, the tumor and/or a CSC, or a population of CSCs may comprise sphere-forming CSCs.

In various embodiments of the above aspects, the methods relate to treating a subject for a tumor disease and/or a cancer disease. In some embodiments the cancer is selected from digestive or gastro-intestinal cancers (e.g., anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric cancer; hepatocellular cancer (e.g., hepatocellular carcinoma) including adult (primary) hepatocellular cancer and childhood hepatocellular cancer; pancreatic cancer including childhood pancreatic cancer; sarcoma, rhabdomyosarcoma; islet cell pancreatic cancer; rectal cancer; and small intestine cancer); lung cancer (e.g., non-small cell lung cancer (NSCLC) and small cell lung cancer (SCLC)); head and neck cancer (e.g., lip and oral cavity cancer; oral cancer including childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer); and breast cancer.

As discussed above, generally the "subject" includes human and non-human animals, particularly mammals. In certain embodiments of the aspects relating to methods of treating a subject, non-limiting examples of subjects include human subjects for example a human patient having a disorder, e.g., a disorder described herein, such as cancer, or a normal subject. In some embodiments, a "non-human" animal or subject includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.). In certain embodiments of the methods disclosed herein, the subject is a human patient.

"Treatment" or "treat" refers to both therapeutic treatment and prophylactic or preventative measures. Those subjects in need of treatment include those already with the disorder as well as those prone to have the disorder or those in which the disorder is to be prevented. Those subjects in need of treatment include those already with the disorder as well as those prone to have the disorder or those in which the disorder is to be prevented. When used with reference to a disease or a subject in need of treatment the terms accordingly include, but are not limited to, halting or slowing of disease progression, remission of disease, prophylaxis of symptoms, reduction in disease and/or symptom severity, or reduction in disease length as compared to an untreated subject. In embodiments, the methods of treatment can abate one or more clinical indications of the particular disease being treated. Certain embodiments relating to methods of treating a disease or condition associated with CSCs that express LOX1, as well as CSCs having an activated LOX1 cascade, comprise administration of therapeutically effective amounts of a compound that inhibits LOX1, as well as pharmaceutical compositions thereof. In embodiments, the method of treating can relate to any method that prevents further progression of the disease and/or symptoms, eliminates the disease, slows or reduces the further progression of the disease and/or symptoms, or reverses the disease and/or clinical symptoms associated with CSCs and cancers associated with CSCs that express LOX1.

In some embodiments the methods may comprise a therapeutically effective amount of an agent that is sufficient to stop or slow the progression of cancer. In further embodiments, a therapeutically effective amount is an amount sufficient to reduce the number of cancer cells, including CSCs, in the subject (i.e., killing of cancer cells, and/or inhibiting proliferation of cancer cells, and/or inducing differentiation of CSCs). Methods for monitoring the proliferation of cancer cells and progress of cancer in a subject (e.g., tumor size, cell counts, biochemical markers, secondary indications, etc.) are discussed herein and may also include techniques generally known in the art.

As discussed herein, some embodiments provide a method of treatment that comprises administering a LOX1 inhibitor in conjunction with radiation, surgery, immunotherapy, or other chemotherapeutics. In some embodiments, the method includes administration of a therapeutically effective amount of an inhibitor of LOX1 in combination with an additional anti-cancer agent. A wide variety of anti-cancer (i.e., anti-neoplastic) agents are known in the art and include, for example alkylating agents, antimetabolites, natural antineoplastic agents, hormonal antineoplastic agents, angiogenesis inhibitors, differentiating reagents, chemotherapeutics, tyrosine kinase inhibitors, RNA inhibitors, antibodies or immunotherapeutic agents, gene therapy agents, small molecule enzymatic inhibitors, biological response modifiers, and anti-metastatic agents. Some non-limiting examples of such active compounds including chemotherapeutic agents generally known in the art include, for example, gemcitabine (Gemzar®), capecitabine (Xeloda®), Doxil®, cytarabine, dexamethasone, ifinotecan (Camptosar®), oxaliplatin (Eloxatin®), albumin-bound paclitaxel (Abraxane®), temozolomide, adriamycin, doxorubicin, epirubicin, 5-fluorouracil, cytosine arabinoside ("Ara-C"), cyclophosphamide, thiotepa, busulfan, cytoxin, taxoids, (e.g., paclitaxel), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, melphalan and other related nitrogen mustards and hormonal agents that act to regulate or inhibit hormone action on tumors such as tamoxifen and onapristone.

Chemotherapeutics have many side effects, one of which is cardiac toxicity (also referred to as cardiotoxicity). In particular, chemotherapeutics have been shown to cause cardiac damage that can lead to cardiomyocyte death and heart failure. In one embodiment, the disclosure provides a method for inhibiting, reducing, or preventing chemotherapy-associated cardiotoxicity in a patient in need of chemotherapy comprising administering to the patient an inhibitor of LOX1 in an amount effective to inhibit, reduce, or prevent chemotherapy-associated cardiotoxicity. In another embodiment, the disclosure provides a method of reversing cardiotoxicity in a patient in need of chemotherapy comprising administering to the patient an inhibitor of LOX1 in an amount effective to reverse chemotherapy-associated cardiotoxicity. In one embodiment, the chemotherapy is an anthracycline, such as doxorubicin.

"Administration" or "administering," as used herein, refers to providing, contacting, and/or delivering a compound or compounds by any appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional or intracranial injection), transdermal, topical, buccal, rectal, vaginal, nasal, ophthalmic, via inhalation, and implants.

"Co-administered," as used herein, refers to simultaneous or sequential administration of multiple compounds or agents. A first compound or agent may be administered before, concurrently with, or after administration of a second compound or agent.

"Contacting," as used herein as in "contacting a cell," refers to contacting a cell directly or indirectly in vitro, ex vivo, or in vivo (i.e. within a subject, such as a mammal, including humans, mice, rats, rabbits, cats, and dogs). Contacting a cell, which may also include "reacting" a cell with or "exposing" a cell to an inhibitor compound, can occur as a result of general administration of a compound or agent to a subject or addition or application of the inhibitor to a vessel containing a cell or tissue or a fluid containing a cell or tissue. Thus, contacting the cell with an inhibitor may refer to administration of an inhibitor to a subject, tissue, or region of a subject or tissue that comprises a cell (e.g., a CSC cell in a localized region or a system in a subject (e.g., lymphatic, circulatory, etc.)) and may not physically contact a target cell. Contacting encompasses the administration to a cell, tissue, mammal, subject, patient, or human. Further, contacting a cell includes adding an agent to a cell culture. Other suitable methods may include introducing or administering an agent to a cell, tissue, mammal, subject, or patient using appropriate procedures and routes of administration as discussed herein or otherwise known in the art.

The disclosure also relates to one or more uses of an inhibitor of LOX1, or a combination of more than one inhibitor of LOX1, in a composition, including therapeutic and pharmaceutical compositions. In embodiments, the uses and compositions comprise the inhibitor(s) in amounts effective to provide for the various methods disclosed herein. In embodiments, the one or more uses relate to uses for the manufacture of a medicament for treating (e.g., killing, eliminating, inhibiting, reducing the progression and/or rate of progression of cell proliferation, reducing the self-renewal and/or expansion capacity of cells (CSCs), reducing the progression and/or rate of progression of a disease state) one of more of the tumor types, cancer stem cells, and/or cancers described herein.

Detection Methods

In some aspects and embodiments the methods disclosed herein provide for and/or comprise one or more methods useful in the detection, identification, and/or quantification of a cancer stem cell (CSC). In some embodiments the method comprises detecting, identifying, and/or quantifying the amount of LOX1 in a biological sample comprising CSCs. In some embodiments, the methods provide for diagnosis, prognosis, quantification, identification, and/or detection of the presence of a cancer stem cell (CSC) in a sample comprising cancer cells, the method can comprise one or more of:

contacting the sample with an agent that binds to a LOX1 nucleic acid sequence or a LOX1 amino acid sequence;
detecting the presence or absence of binding between the agent and the LOX1 nucleic acid sequence or the LOX1 amino acid sequence; and/or
identifying the presence of the CSC in the sample upon detection of binding between the agent and the LOX1 nucleic acid sequence or the LOX1 amino acid sequence.

In these methods the steps may be used alone or in any series of combinations with each other or other techniques generally known in the art. In some embodiments of this aspect, the method can further comprise one or more of:

quantifying the amount of the LOX1 nucleic acid sequence or the LOX1 amino acid sequence in the sample;
comparing the amount of the LOX1 nucleic acid sequence or the LOX1 amino acid sequence to a reference level of LOX1 nucleic acid or LOX1 amino acid; and/or
identifying the presence of the CSC in the sample when the detected amount is greater than the reference level.

In some aspects and embodiments the methods disclosed herein provide for and/or comprise one or more methods useful in the detection, identification, and/or quantification of a LOX1 positive cancer stem cell (CSC). In some embodiments the method comprises detecting, identifying, and/or quantifying the amount of LOX1 positive CSCs in a biological sample comprising CSCs. In some embodiments, the methods provide for diagnosis, prognosis, quantification, identification, and/or detection of the presence of a LOX1 positive cancer stem cell (CSC) in a sample comprising cancer cells, the method can comprise one or more of:

contacting the sample with an agent that binds to a LOX1 nucleic acid sequence or a LOX1 amino acid sequence;

detecting the presence or absence of binding between the agent and the LOX1 nucleic acid sequence or the LOX1 amino acid sequence; and/or identifying the presence of the LOX1 positive CSC in the sample upon detection of binding between the agent and the LOX1 nucleic acid sequence or the LOX1 amino acid sequence.

In yet further embodiments, the method may comprise an agent comprising a detectable moiety. In some embodiments, the agent may comprise a nucleic acid sequence that hybridizes to at least a portion of the LOX1 nucleic acid sequence under stringent hybridization conditions. In some embodiments, the agent may comprise an antibody that specifically binds to at least a portion of the LOX1 amino acid sequence.

In various embodiments of the above aspects, the methods relate to a tumor and/or a CSC, or a population of CSCs expressing LOX1. In further embodiments, the tumor and/or a CSC, or a population of CSCs may comprise sphere-forming CSCs.

In addition to the methods described herein that are useful for detecting, identifying, and/or quantifying a CSC in a sample, these aspects and embodiments can also include any method and technique that is available to one of ordinary skill in the art. As non-limiting examples, CSCs may be identified, detected, and isolated using techniques including flow cytometry based on cell surface markers that are expressed in, or specific for particular CSCs; detection of side-population (SP) phenotypes by dye exclusion (e.g., Hoechst 33342, as disclosed in Moserle, L., et al., Cancer Res. (2008) 68; 5658-5668); ability to grow/proliferate as floating spheres in serum-free medium (e.g., disclosed herein as well as in Ryback, A. P., et al., Biochim. Biophys. Acta (2011) 1813; 683-694); and determination of particular enzymatic activity such as, for example, aldehyde dehydrogenase activity, and levels of polycomb markers including polycomb heterochromatin marker, H3K27me$^3$ levels, and polycomb group protein enhancer of zeste 2 (EZH2).

In some embodiments, for example, elevated aldehyde dehydrogenase (ALDH) expression and activity has been reported in cancer precursor cells of various lineages, (e.g., hematopoietic, mammary, endothelial, mesenchymal, neural) and techniques and commercially available kits (e.g., ALDEFLUOR™, Stemcell Technologies) may be used in connection with the various aspects and embodiments herein. Similarly, while there are currently no universally expressed cell surface markers for identifying CSCs, a number of surface markers have been associated with CSCs and associated tumor types, including, for example, ALDH, CD13, CD15, CD24, CD44, CD90, CD117, CD133, CD166, CD326, (see, e.g., Xia, P., Curr Stem Cell Res Ther. (2014) March; 9(2): 102-11; Shimamura, M., et al., Endocr. J., (2014) 61(5):481-90; Tirino, V., et al., FASEB J., (2013) January; 27(1):13-24).

In some embodiments, because of the lack of one or more universal surface markers for the detection or identification of a CSC in a sample, methods of detecting, identifying, and/or quantifying comprise cell culture techniques comprising sphere cultures and growth assays such as disclosed herein or otherwise known in the art.

B. Inhibitors

The methods, uses, and compositions described herein include embodiments relating to agents capable of inhibiting, downregulating, or abolishing the activity and/or the expression of LOX1, or any combination of one or more such inhibitor agents. As long as the agent possesses the inhibitory function (e.g., inhibits LOX1 expression and/or activity), the inhibitor agent may be selected from any class of compound. For example, the inhibitors may be selected from the group consisting of a polypeptide that inhibits LOX1, a small molecule that inhibits LOX1, a polynucleotide that inhibits LOX1, an aptamer that inhibits LOX1, an antibody that inhibits LOX1, or an antisense molecule or siRNA molecule that inhibits LOX1. Thus, the inhibitors as used herein refer to any compound that reduces, inhibits, downregulates, or abolishes the expression and/or function of LOX1, or an agent suitable for neutralizing, reducing, or inhibiting the expression or function of LOX1. The inhibitors described herein may exert action by any mechanism including, for example, binding to LOX1. Upon binding, an inhibitor may, for example, inhibit the interaction of LOX1 with a receptor or a ligand, such that LOX1 cannot activate the receptor, or cannot be activated by a ligand. In other embodiments, the agent(s) capable of inhibiting the activity of LOX1 may inhibit the chemotactic activity, may sequester the proteins and reduce bioavailability, or any combinations thereof.

In some embodiments, the inhibitor may be a polypeptide or a small molecule capable of binding to LOX1, and may be identified by any technique routine in the art (e.g., screening small compound or polypeptide libraries). A "small molecule" as used herein generally refers to small organic compounds having low molecular weight. A small molecule may be a synthetic compound not known to occur in nature or a naturally-occurring compound isolated from or known to occur in natural sources, such as e.g. cells, plants, fungi, animals and the like. In some embodiments, a small molecule may have a molecular weight of less than 5000 Daltons, less than 4000 Daltons, less than 3000 Daltons, less than 2000 Daltons, less than 1000 Daltons, or less than about 800 Daltons. In such embodiments a small molecule typically has a molecular weight of greater than about 100 Daltons.

Whether a small molecule or polypeptide is capable of binding to LOX1 may be determined by any routine technique or assay, as well as the techniques and assays that are described herein. For example, techniques may include a yeast two-hybrid assay or a biochemical assay such as e.g. a pull-down assay, a co-immunoprecipitation assay, an enzyme-linked immunosorbent assay (ELISA), a quantitative radioligand binding assay, a Plasmon resonance assay or any other method routinely used in the art. Typically, when using pull-down or Plasmon resonance assays, it is useful to fuse or otherwise link at least one of the proteins to an affinity tag such as HIS-tag, GST-tag or other detectable moiety generally used in the art. Whether a polypeptide or any other compound to be tested is capable of inhibiting the activity of LOX1 may be determined by measuring the activity of membrane-bound polypeptide. Suitably, a polypeptide is capable of inhibiting the activity of LOX1.

In embodiments, the inhibitor may be an "aptamer" which refers to a DNA, RNA or peptide aptamer having specificity for LOX1. A polynucleotide aptamer comprises anywhere from about 10 to about 300 nucleotides in length. Typically, an aptamer ranges from about 30 to about 100 nucleotides in length, and in some embodiments may range from about 10 to 60 nucleotides in length. Aptamers may be prepared by any known method, including synthetic, recombinant, and purification methods, and may be used alone or in combination with other aptamers specific for LOX1.

In some particular embodiments of the methods referred to herein, the inhibitor may be an antibody that specifically binds LOX1. In some embodiments the antibody may be a monoclonal or polyclonal antibody, or a polyspecific antisera. In such embodiments, the antibody may also include antibody variants or fragments as discussed above and including, for example, single chain antibodies, diabodies, minibodies, single chain Fv fragments (sc(Fv)), sc(Fv)$_2$ antibodies, Fab fragments, or F(ab')$_2$ fragments, as long as the variant or fragment retains specific binding properties to LOX1.

Exemplary LOX1 binding proteins are provided in Table 1 below and are described in International Patent Application No. PCT/EP2015/072644, which is incorporated by reference herein in its entirety.

TABLE 1

| Exemplary LOX1 binding proteins | |
|---|---|
| Binding protein ID | Amino acid Sequence (SEQ ID NO) |
| Lox514 | |
| VH CDR1 | ELSMH (SEQ ID NO: 1) |
| VH CDR2 | GFDPEDGETIYAQKFQG (SEQ ID NO: 5) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEW MGGFDPEDGETIYAQKFQGRVTMTEDTSTDTAYMELSSLRSEDTAVYYC ATPNGQQGKGVRGWDYYYGMDVWGRGTTVTVSS (SEQ ID NO: 29) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSGW VFGGGTKLTVL (SEQ ID NO: 33) |
| LX5140011 | |
| VH CDR1 | ELSMH (SEQ ID NO: 1) |
| VH CDR2 | GFDPEDWEYAYDQKFQG (SEQ ID NO: 6) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEW MGGFDPEDWEYAYDQKFQGRVTMTEDTSTDTAYMELSSLRSEDTAVYY CATPNGQQGKGVRGWDYYYGMDVWGQGTTVTVSS (SEQ ID NO: 19) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSGW VFGGGTKLTVL (SEQ ID NO: 33) |
| LX5140014 | |
| VH CDR1 | ELSMH (SEQ ID NO: 1) |
| VH CDR2 | GFDPEDYTIRVGQKFQG (SEQ ID NO: 7) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEW MGGFDPEDYTIRVGQKFQGRVTMTEDTSTDTAYMELSSLRSEDTAVYYC ATPNGQQGKGVRGWDYYYGMDVWGQGTTVTVSS (SEQ ID NO: 20) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSGW VFGGGTKLTVL (SEQ ID NO: 33) |

TABLE 1-continued

Exemplary LOX1 binding proteins

| Binding protein ID | Amino acid Sequence (SEQ ID NO) |
|---|---|
| LX5140016 | |
| VH CDR1 | ELSMH (SEQ ID NO: 1) |
| VH CDR2 | GFDPEDWQTHTAQKFQG (SEQ ID NO: 8) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEWMGGFDPEDWQTHTAQKFQGRVTMTEDTSTDTAYMELSSLRSEDTAVYYCATPNGQQGKGVRGWDYYYGMDVWGQGTTVTVSS (SEQ ID NO: 21) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGWVFGGGTKLTVL (SEQ ID NO: 33) |
| LX5140038 | |
| VH CDR1 | ELSMH (SEQ ID NO: 1) |
| VH CDR2 | GFDPEDWTIHVDQKFQG (SEQ ID NO: 9) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEWMGGFDPEDWTIHVDQKFQGRVTMTEDTSTDTAYMELSSLRSEDTAVYYCATPNGQQGKGVRGWDYYYGMDVWGQGTTVTVSS (SEQ ID NO: 22) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGWVFGGGTKLTVL (SEQ ID NO: 33) |
| LX5140094 | |
| VH CDR1 | ELSMH (SEQ ID NO: 1) |
| VH CDR2 | GFDPEDWQYHVSQKFQG (SEQ ID NO: 10) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEWMGGFDPEDWQYHVSQKFQGRVTMTEDTSTDTAYMELSSLRSEDTAVYYCATPNGQQGKGVRGWDYYYGMDVWGQGTTVTVSS (SEQ ID NO: 23) |
| VL CDR1 | TGSSSNIGAGYDVH (SEQ ID NO: 30) |
| VL CDR2 | GNSNRPS (SEQ ID NO: 31) |
| VL CDR3 | QSYDSMYRFG (SEQ ID NO: 34) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSMYRFGFGGGTKLTVL (SEQ ID NO: 36) |
| LX5140108 | |
| VH CDR1 | ELSMH (SEQ ID NO: 1) |
| VH CDR2 | GFDPEDWSNHVSQKFQG (SEQ ID NO: 11) |
| VH CDR3 | STGRQGKGVRGWDYYYGMDV (SEQ ID NO: 15) |

TABLE 1-continued

Exemplary LOX1 binding proteins

| Binding protein ID | Amino acid Sequence (SEQ ID NO) |
|---|---|
| VH | QVQLVQSGAEVKKPGASVKVSCKVSGYTLTELSMHWVRQAPGKGLEW MGGFDPEDWSNHVSQKFQGRVTMTEDTSTDTAYMELSSLRSEDTAVYY CLTSTGRQGKGVRGWDYYYGMDVWGQGTTVTVSS (SEQ ID NO: 24) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSGW VFGGGTKLTVL (SEQ ID NO: 33) |
| LX5140110 | |
| VH CDR1 | ELSMH (SEQ ID NO: 1) |
| VH CDR2 | GFDPEDFKYHTHQKFQG (SEQ ID NO: 2) |
| VH CDR3 | VWGTQGKGVRGWDYYYGMDV (SEQ ID NO: 3) |
| VH | QVQLVQSGAEVKKPGASVKVSCKVSGYTLTELSMHWVRQAPGKGLEW MGGFDPEDFKYHTHQKFQGRVTMTEDTSTDTAYMELSSLRSEDTAVYY CALVWGTQGKGVRGWDYYYGMDVWGQGTTVTVSS (SEQ ID NO: 4) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSGW VFGGGTKLTVL (SEQ ID NO: 33) |
| LX5140092 | |
| VH CDR1 | ELSMH (SEQ ID NO: 1) |
| VH CDR2 | GFDPEDWKYHLSQKFQG (SEQ ID NO: 12) |
| VH CDR3 | PNGTHQGGVRGWDYYYGMDV (SEQ ID NO: 17) |
| VH | QVQLVQSGAEVKKPGASVKVSCKVSGYTLTELSMHWVRQAPGKGLEW MGGFDPEDWKYHLSQKFQGRVTMTEDTSTDTAYMELSSLRSEDTAVYY CATPNGTHQGGVRGWDYYYGMDVWGQGTTVTVSS (SEQ ID NO: 26) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSGW VFGGGTKLTVL (SEQ ID NO: 33) |
| LX5140092_D | |
| VH CDR1 | ELSMH (SEQ ID NO: 1) |
| VH CDR2 | GFDPEDWKYHLSQKFQG (SEQ ID NO: 12) |
| VH CDR3 | PDGTHQGGVRGWDYYYGMDV (SEQ ID NO: 16) |
| VH | QVQLVQSGAEVKKPGASVKVSCKVSGYTLTELSMHWVRQAPGKGLEW MGGFDPEDWKYHLSQKFQGRVTMTEDTSTDTAYMELSSLRSEDTAVYY CATPDGTHQGGVRGWDYYYGMDVWGQGTTVTVSS (SEQ ID NO: 25) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |

TABLE 1-continued

Exemplary LOX1 binding proteins

| Binding protein ID | Amino acid Sequence (SEQ ID NO) |
|---|---|
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSGW VFGGGTKLTVL (SEQ ID NO: 33 |
| LX5140093 | |
| VH CDR1 | ELSMH (SEQ ID NO: 1) |
| VH CDR2 | GFDPEDWAYHQAQKFQG (SEQ ID NO: 13) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEW MGGFDPEDWAYHQAQKFQGRVTMTEDTSTDTAYMELSSLRSEDTAVY YCATPNGQQGKGVRGWDYYYGMDVWGQGTTVTVSS (SEQ ID NO: 27) |
| VL CDR1 | TGSSSNIGAGYDVH (SEQ ID NO: 30) |
| VL CDR2 | GNSNRPS (SEQ ID NO: 31) |
| VL CDR3 | QSYDSSHRAWA (SEQ ID NO: 35) |
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSHRA WAFGGGTKLTVL (SEQ ID NO: 37 |
| LX5140093_D | |
| VH CDR1 | ELSMH (SEQ ID NO: 1) |
| VH CDR2 | GFDPEDWAYHQAQKFQG (SEQ ID NO: 13) |
| VH CDR3 | PDGQQGKGVRGWDYYYGMDV (SEQ ID NO: 18) |
| VH | QVQLVQSGAEVKKPGASVKVSCKVSGYTLTELSMHWVRQAPGKGLEW MGGFDPEDWAYHQAQKFQGRVTMTEDTSTDTAYMELSSLRSEDTAVY YCATPDGQQGKGVRGWDYYYGMDVWGQGTTVTVSS (SEQ ID NO: 28) |
| VL CDR1 | TGSSSNIGAGYDVH (SEQ ID NO: 30) |
| VL CDR2 | GNSNRPS (SEQ ID NO: 31) |
| VL CDR3 | QSYDSSHRAWA (SEQ ID NO: 35) |
| VL | QSVVTQPPSVSGAPGQRVTISCTGSSSNIGAGYDVHWYQQLPGTAPKLLI YGNSNRPSGVPDRFSGSKSGTSASLAITGLQAEDEADYYCQSYDSSHRA WAFGGGTKLTVL (SEQ ID NO: 37 |
| Lox696 | |
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQAPGKGLEW VSGISWNSGSIGYADSVKGRFTISRDNAKNSLYLQMNSLRAEDTAVYYC AREGNWNYDAFDIWGRGTTVTVSS (SEQ ID NO: 54) |
| VL CDR1 | TGTSSDVGGYNYVS (SEQ ID NO: 55) |
| VL CDR2 | DVSNRPS (SEQ ID NO: 60) |
| VL CDR3 | SSYTSSSTNWV (SEQ ID NO: 61) |
| VL | QSALTQPASVSGSPGQSITISCTGTSSDVGGYNYVSWYQQHPGKAPKLMI YDVSNRPSGVSNRFSGSKSGNTASLTISGLQAEDEADYYCSSYTSSSTNW VFGGGTKLTVL (SEQ ID NO: 70) |
| LX6960067_ng11 | |
| VH CDR1 | DYAMH (SEQ ID NO: 38) |
| VH CDR2 | GVSLQELYTGYADSVKG (SEQ ID NO: 42) |

TABLE 1-continued

Exemplary LOX1 binding proteins

| Binding protein ID | Amino acid Sequence (SEQ ID NO) |
|---|---|
| VH CDR3 | EGSWNYDAFDI (SEQ ID NO: 45) |
| VH | QVQLVQSGGGLVQPGRSLRLSCAASGFTFDDYAMHWVRQAPGKGLEWVSGVSLQELYTGYADSVKGRFTVSGDNAKNSLYLQMNSLRAEDTAVYYCAREGSWNYDAFDIWGRGTTVTVSS (SEQ ID NO: 48) |
| VL CDR1 | TGTSSDVGGYNYVS (SEQ ID NO: 55) |
| VL CDR2 | DVSNRPS (SEQ ID NO: 60) |
| VL CDR3 | LGRTWSSTNWV (SEQ ID NO: 62) |
| VL | QSALTQPASVSGSPGQSITISCTGTSSDVGGYNYVSWYQQHPGKAPKLMIYDVSNRPSGVSNRFSGSKSGNTASLTISGLQAEDEADYYCLGRTWSSTNWVFGGGTKLTVL (SEQ ID NO: 65) |
| LX6960071_ngl1 | |
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQAPGKGLEWVSGISWNSGSIGYADSVKGRFTISRDNAKNSLYLQMDSLRAEDTAVYYCAREGNWNYDAFDIWGRGTTVTVSS (SEQ ID NO: 49) |
| VL CDR1 | TGTSSDVGGYNYVS (SEQ ID NO: 55) |
| VL CDR2 | DVSNRPS (SEQ ID NO: 60) |
| VL CDR3 | MGGMGRSTNWV (SEQ ID NO: 57) |
| VL | QSALTQPASVSGSPGQPITISCTGTSSDVGGYNYVSWYQQHPGKAPKLMIYDVSNRPSGVSNRFSGSKSGNTASLTISGLQAEDEADYYCMGSMGRSTNWVFGGGTKLTVL (SEQ ID NO: 66) |
| LX6960073_ngl1 | |
| VH CDR1 | DYAMH (SEQ ID NO: 38) |
| VH CDR2 | GISWNSGSIGYADSVKG (SEQ ID NO: 39) |
| VH CDR3 | EGSWNYDALDI (SEQ ID NO: 46) |
| VH | QVQLVQSGGGLVQPGRSLRLSCAASGFTSDDYAMHWVRQAPGKGLEWVSGISWNSGSIGYADSVKGRFTISRDNAKNSLYLQMNGLRAEDTAVYYCAREGSWNYDALDIWGRGTTVTVSS (SEQ ID NO: 50) |
| VL CDR1 | TGTSSDVGGYNYVS (SEQ ID NO: 55) |
| VL CDR2 | DVSKRPS (SEQ ID NO: 56) |
| VL CDR3 | MGGMGRSTNWV (SEQ ID NO: 57) |
| VL | QSALTQPASVSGSPGQPITISCTGTSSDVGGYNYVSWYQQHPGKAPKLMIYDVSKRPSGVSNRFSGSKSGNTASLTISGLQAEDEADYYCMGGMGRSTNWVFGGGTKLTVL (SEQ ID NO: 67) |
| LX6960086_ngl1 | |
| VH CDR1 | DYAMH (SEQ ID NO: 38) |
| VH CDR2 | GISWNSPDRYMDDSVKG (SEQ ID NO: 43) |
| VH CDR3 | EGNWNYDAFDI (SEQ ID NO: 44) |
| VH | QVQLVQSGGGLVQPGRSLRLSCAASGFTFDDYAMHWVRQAPGKGLEWVSGISWNSPDRYMDDSVKGRFTISRDNAQNSLYLQMDSLRAEDTAVYYCAREGNWNYDAFDIWGRGTTVTVSS (SEQ ID NO: 51) |
| VL CDR1 | TGTSSDVGGYNYVS (SEQ ID NO: 55) |
| VL CDR2 | DVSNRPS (SEQ ID NO: 60) |

TABLE 1-continued

Exemplary LOX1 binding proteins

| Binding protein ID | Amino acid Sequence (SEQ ID NO) |
|---|---|
| VL CDR3 | LGRTWSSTNWV (SEQ ID NO: 62) |
| VL | QSALTQPASVSGSPGQSITISCTGTSSDVGGYNYVSWYQQHPGKAPKLMI YDVSNRPSGVSNRFSGSKSGNTASLTISGLQAEDEADYYCLGRTWSSTN WVFGGGTKLTVL (SEQ ID NO: 65) |

LX6960094_ngl1

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VL | QVQLVQSGGGLVQPGRSLRLSCAASGFTFDDYAMHWVRQAPGKGLEW VSGISWNSGSIGYADSVKGRFTISRDNAKNSLYLQMNSLRAEDTAVYYC AREGNWNYDAFDIWGRGTTVTVSS (SEQ ID NO: 54) |
| VL CDR1 | TGTSSDVGGYNYVS (SEQ ID NO: 55) |
| VL CDR2 | DVSNRPS (SEQ ID NO: 60) |
| VL CDR3 | AQRTVSSTNWV (SEQ ID NO: 64) |
| VL | QSALTQPASVSGSPGQSITISCTGTSSDVGGYNYVSWYQQHPGKAPKLMI YDVSNRPSGVSNRFSGSKSGNTASLTISGLQAEDEADYYCAQRTVSSTN WVFGGGTKLTVL (SEQ ID NO: 68) |

LX6960101_ngl1

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDV (SEQ ID NO: 47) |
| VH | QVQLVQSGGGLVQPGRSLRLSCAASGFTFDDYAMHWVRQAPGKGLEW VSGISWNSGSIGYADSVKGRFTISRDNAKNSLYLQMNGLRAEDTAVYYC AREGNWNYDAFDVWGRGTTVTVSS (SEQ ID NO: 52) |
| VL CDR1 | TGTSSDVGGYNYVS (SEQ ID NO: 55) |
| VL CDR2 | DVSNRPS (SEQ ID NO: 60) |
| VL CDR3 | MGGMGRSTNWV (SEQ ID NO: 57) |
| VL | QSALTQPASVSGSPGQPITISCTGTSSDVGGYNYVSWYQQHPGKAPKLMI YDVSKRPSGVSNRFSGSKSGNTASLTISGLQAEDEADYYCMGGMGRSTN WVFGGGTKLTVL (SEQ ID NO: 67) |

LX6960102_ngl1

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQAPGKGLEW VSGISWNSGSIGYADSVKGRFTISRDNAKNSLYLQMNSLRAEDTAVYYC AREGNWNYDAFDIWGRGTTVTVSS (SEQ ID NO: 54) |
| VL CDR1 | TGTSSDVGGYNYVS (SEQ ID NO: 55) |
| VL CDR2 | DVSNRPS (SEQ ID NO: 60) |
| VL CDR3 | MGGMGRSTNWV (SEQ ID NO: 57) |
| VL | QSALTQPASVSGSPGQSITISCTGTSSDVGGYNYVSWYQQHPGKAPKLMI YDVSNRPSGVSNRFSGSKSGNTASLTISGLQAEDEADYYCSSYTSSSTNW VFGGGTKLTVL (SEQ ID NO: 70) |

LX6960116_ngl1

| | |
|---|---|
| VH CDR1 | DYAMH (SEQ ID NO: 38) |

TABLE 1-continued

Exemplary LOX1 binding proteins

| Binding protein ID | Amino acid Sequence (SEQ ID NO) |
|---|---|
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQAPGKGLEW VSGISWNSGSIGYADSVKGRFTISRDNAKNSLYLQMNSLRAEDTAVYYC AREGNWNYDAFDIWGRGTTVTVSS (SEQ ID NO: 54) |
| VL CDR1 | TGTSNDVGGYNYVS (SEQ ID NO: 59) |
| VL CDR2 | DVSNRPS (SEQ ID NO: 60) |
| VL CDR3 | SSYTSSSTNWV (SEQ ID NO: 61) |
| VL | QSALTQPASVSGSPGQSITISCTGTSNDVGGYNYVSWYQQHPGKAPKLMI YDVSNRPSGVSNRFSGSKSGNTASLTISGLQAEDEADYYCMGSMGRSTN WVFGGGTKLTVL (SEQ ID NO: 69) |
| LX6960073_gl | |
| VH CDR1 | DYAMH (SEQ ID NO: 38) |
| VH CDR2 | GISWNSGSIGYADSVKG (SEQ ID NO: 39) |
| VH CDR3 | EGSWNYDALDI (SEQ ID NO: 40) |
| VH | EVQLVESGGGLVQPGRSLRLSCAASGFTSDDYAMHWVRQAPGKGLEW VSGISWNSGSIGYADSVKGRFTISRDNAKNSLYLQMNGLRAEDTAVYYC AREGSWNYDALDIWGQGTMVTVSS (SEQ ID NO: 53) |
| VL CDR1 | TGTSSDVGGYNYVS (SEQ ID NO: 55) |
| VL CDR2 | DVSKRPS (SEQ ID NO: 56) |
| VL CDR3 | MGGMGRSTNWV (SEQ ID NO: 57) |
| VL | QSALTQPASVSGSPGQPITISCTGTSSDVGGYNYVSWYQQHPGKAPKLMI YDVSKRPSGVSNRFSGSKSGNTASLTISGLQAEDEADYYCMGGMGRSTN WVFGGGTKLTVL (SEQ ID NO: 58) |
| LX6960073_G82bS_gl | |
| VH CDR1 | DYAMH (SEQ ID NO: 38) |
| VH CDR2 | GISWNSGSIGYADSVKG (SEQ ID NO: 39) |
| VH CDR3 | EGSWNYDALDI (SEQ ID NO: 40) |
| VH | EVQLVESGGGLVQPGRSLRLSCAASGFTSDDYAMHWVRQAPGKGLEW VSGISWNSGSIGYADSVKGRFTISRDNAKNSLYLQMNSLRAEDTAVYYC AREGSWNYDALDIWGQGTMVTVSS (SEQ ID NO: 41) |
| VL CDR1 | TGTSSDVGGYNYVS (SEQ ID NO: 55) |
| VL CDR2 | DVSKRPS (SEQ ID NO: 56) |
| VL CDR3 | MGGMGRSTNWV (SEQ ID NO: 57) |
| VL | QSALTQPASVSGSPGQPITISCTGTSSDVGGYNYVSWYQQHPGKAPKLMI YDVSKRPSGVSNRFSGSKSGNTASLTISGLQAEDEADYYCMGGMGRSTN WVFGGGTKLTVL (SEQ ID NO: 58 |

In some aspects the isolated LOX1-binding protein comprises a VH sequence that has a total of one, two, three, four, five, six, seven, eight or fewer amino acid substitutions, deletions and/or insertions from a reference VH sequence of SEQ ID NO:4. The disclosure also provides nucleic acids encoding the LOX1-binding protein, vectors containing these nucleic acids and host cells transformed with these nucleic acids and vectors, and methods of making and using the LOX1-binding protein.

In further aspects, the isolated LOX1-binding protein comprises a VH of SEQ ID NO:4. The disclosure also provides nucleic acids encoding the LOX1-binding protein, vectors containing these nucleic acids and host cells transformed with these nucleic acids and vectors, and methods of making and using the LOX1-binding protein.

In some aspects the isolated LOX1-binding protein comprises a VL sequence that has a total of one, two, three, four, five, six, seven, eight or fewer amino acid substitutions, deletions and/or insertions from a reference VL sequence of SEQ ID NO:33. The disclosure also provides nucleic acids encoding the LOX1-binding protein, vectors containing these nucleic acids and host cells transformed with these nucleic acids and vectors, and methods of making and using the LOX1-binding protein.

In further aspects, the isolated LOX1-binding protein comprises a VL of SEQ ID NO:33. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a VH selected from a VH containing a VH-CDR1 having the amino acid sequence of SEQ ID NO:1, a VH-CDR2 having the amino acid sequence of SEQ ID NO:2, 5-12 or 13, and a VH-CDR3 having the amino acid sequence of SEQ ID NO:3, 14-17 or 18; and a light chain VL selected from a VL containing a VL-CDR1 having the amino acid sequence of SEQ ID NO:30, a VL-CDR2 having the amino acid sequence of SEQ ID NO:31, and a VL-CDR3 having the amino acid sequence of SEQ ID NO:32, 34, or 35. The disclosure also provides nucleic acids encoding the LOX1-binding protein, vectors containing these nucleic acids and host cells transformed with these nucleic acids and vectors, and methods of making and using the LOX1-binding protein.

The methods also relate to an isolated LOX1-binding protein comprising a VH and a VL sequence that each have a total of one, two, three, four, five, six, seven, eight or fewer amino acid substitutions, deletions, and/or insertions from a reference VH and VL LOX1-binding proteins disclosed herein. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein has a VH comprising SEQ ID NO:4, 19-28, or 29, and a VL comprising SEQ ID NO:33, 36, or 37. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein comprises a set of complementary determining regions (CDRs): heavy chain variable region (VH)-CDR1, VH-CDR2, VH-CDR3, and light chain variable region (VL)-CDR1, VL-CDR2 and VL-CDR3 wherein the set of CDRs is identical to, or has a total of 18 or fewer (e.g. 1, 2, 3, 4, 5, 6, 7, 8, 9, 10, 11, 12, 13, 14, 15, 16, 17 or 18) amino acid substitutions, deletions, and/or insertions from a reference set of CDRs in which: (a) VH-CDR1 has the amino acid sequence of SEQ ID NO:1; (b) VH-CDR2 has the amino acid sequence of SEQ ID NO:5; (c) VH-CDR3 has the amino acid sequence of SEQ ID NO:14; (d) VL-CDR1 has the amino acid sequence of SEQ ID NO:30; (e) VL-CDR2 has the amino acid sequence of SEQ ID NO:31; and (f) VL-CDR3 has the amino acid sequence of SEQ ID NO:32 The disclosure also provides nucleic acids encoding the LOX1-binding protein, vectors containing these nucleic acids and host cells transformed with these nucleic acids and vectors, and methods of making and using the LOX1-binding protein.

In further aspects, the LOX1-binding protein comprises a set of CDRs: VH-CDR1, VH-CDR2, VH-CDR3, VL-CDR1, VL-CDR2 and VL-CDR3 wherein: (a) VH-CDR1 has the amino acid sequence of SEQ ID NO:1; (b) VH-CDR2 has the amino acid sequence of SEQ ID NO:2; (c) VH-CDR3 has the amino acid sequence of SEQ ID NO:3; (d) VL-CDR1 has the amino acid sequence of SEQ ID NO:30; (e) VL-CDR2 has the amino acid sequence of SEQ ID NO:31; and (f) VL-CDR3 has the amino acid sequence of SEQ ID NO:32. The disclosure also provides nucleic acids encoding the LOX1-binding protein, vectors containing these nucleic acids and host cells transformed with these nucleic acids and vectors, and methods of making and using the LOX1-binding protein.

The methods also relate to an isolated LOX1-binding protein comprising a heavy chain variable region (VH) having at least 90, 95, 97, 98 or 99% sequence identity to a reference VH sequence disclosed herein and/or a light chain variable region (VL) having at least 90, 95, 97, 98 or 99% sequence identity to a reference VL sequence disclosed herein (e.g., the VH and VL sequences disclosed in Table 1). In further aspects, the isolated LOX1-binding protein comprises a VH having at least 90, 95, 97, 98 or 99% sequence identity to SEQ ID NO:4 and/or a VL having at least 90, 95, 97, 98 or 99% sequence identity to SEQ ID NO:33. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a heavy chain variable region (VH) having at least 90, 95, 97, 98 or 99% sequence identity and a light chain variable region (VL) having at least 90, 95, 97, 98 or 99% sequence identity to a VH and a VL selected from the group consisting of: (a) a VH having the amino acid sequence of SEQ ID NO:4 and a VL having the amino acid sequence of SEQ ID NO:33; (b) a VH having the amino acid sequence of SEQ ID NO:29 and a VL having the amino acid sequence of SEQ ID NO:33; (c) a VH having the amino acid sequence of SEQ ID NO:41 and a VL having the amino acid sequence of SEQ ID NO:58; and (d) a VH having the amino acid sequence of SEQ ID NO:54 and a VL having the amino acid sequence of SEQ ID NO:70. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a VH having at least 90, 95, 97, 98 or 99% sequence identity and a VL having at least 90, 95, 97, 98 or 99% sequence identity to a VH and a VL selected from the group consisting of: (a) a VH having the amino acid sequence of SEQ ID NO:19 and a VL having the amino acid sequence of SEQ ID NO:33; (b) a VH having the amino acid sequence of SEQ ID NO:20 and a VL having the amino acid sequence of SEQ ID NO:33; (c) a VH having the amino acid sequence of SEQ ID NO:21 and a VL having the amino acid sequence of SEQ ID NO:33; (d) a VH having the amino acid sequence of SEQ ID NO:22 and a VL having the amino acid sequence of SEQ ID NO:33; (e) a VH having the amino acid sequence of SEQ ID NO:23 and a VL having the amino acid sequence of SEQ ID NO:33; (f) a VH having the amino acid sequence of SEQ ID NO:24 and a VL having the amino acid sequence of SEQ ID NO:33; (g) a VH having the amino acid sequence of SEQ ID NO:25 and a VL having the amino acid sequence of SEQ ID NO:33; (h) a VH having the amino acid sequence of SEQ ID NO:26 and a VL having the amino acid sequence of SEQ ID NO:33; (i) a VH having the amino acid sequence of SEQ ID NO:27 and a VL having the amino acid sequence of SEQ ID NO:37; (j) a VH having the amino acid sequence of SEQ ID NO:28 and a VL having the amino acid sequence of SEQ ID NO:37; (k) a VH having the amino acid sequence of SEQ ID NO:48 and a VL having the amino acid sequence of SEQ ID NO:65; (1) a VH having the amino acid sequence of SEQ ID NO:49 and a VL having the amino acid sequence of SEQ ID NO:66; (m) a VH having the amino acid sequence of SEQ ID NO:50 and a VL having the amino acid sequence of SEQ ID NO:67; (n) a VH having the amino acid sequence of SEQ ID NO:51 and a VL having the amino acid sequence of SEQ ID NO:65; (o) a VH having the amino acid sequence of SEQ ID NO:54 and a VL having the amino acid sequence of SEQ ID NO:68; (p) a VH having the amino acid sequence of SEQ ID NO:52 and a VL having the amino acid sequence of SEQ ID NO:67; (q) a VH having the amino acid sequence of SEQ ID NO:54 and a VL having the amino acid sequence of SEQ ID NO:69; (r) a VH having the amino acid sequence of SEQ ID NO:53 and a VL having the amino acid sequence of SEQ ID NO:58; and (s) a VH having the amino acid sequence of SEQ ID NO:41 and a VL having the amino acid sequence of SEQ ID NO:58. The disclosure also provides nucleic acids encoding the LOX1-binding protein, vectors containing these nucleic acids and host cells transformed with these nucleic acids and vectors, and methods of making and using the LOX1-binding protein.

In further aspects, the methods herein may comprise an isolated LOX1-binding protein comprising a VH-CDR3 having the amino acid sequence of SEQ ID NO:3. In further aspects, the LOX1-binding protein comprises a VH-CDR3 having the amino acid sequence of SEQ ID NO:3 and a VH-CDR2 having the amino acid sequence of SEQ ID NO:2. In other aspects, the LOX1-binding protein comprises a VH-CDR3 having the amino acid sequence of SEQ ID NO:3 and a VH-CDR2 having the amino acid sequence of SEQ ID NO:5-12 or 13. In additional aspects, the LOX1-binding protein comprises a VH-CDR3 having the amino acid sequence of SEQ ID NO:3, 14-17 or 18 and a VH-CDR2 having the amino acid sequence of SEQ ID NO:2. In further aspects, the LOX1-binding protein comprises a VH-CDR3 having the amino acid sequence of SEQ ID NO: 3, 14-17 or 18 and a VH-CDR2 having the amino acid sequence of SEQ ID NO:2, 5-12 or 13. In further aspects, the LOX1-binding protein comprises a VH-CDR3 having the amino acid sequence of SEQ ID NO: 3, 14-17 or 18 and a VH-CDR2 having the amino acid sequence of SEQ ID NO:2, 5-12 or 13 and a VH-CDR1 having the amino acid sequence of SEQ ID NO:1. The disclosure also provides nucleic acids encoding the LOX1-binding protein, vectors containing these nucleic acids and host cells transformed with these nucleic acids and vectors, and methods of making and using the LOX1-binding protein.

In further aspects, the isolated LOX1-binding protein comprises a VLH-CDR3 having the amino acid sequence of SEQ ID NO:32. In further aspects, the LOX1-binding protein comprises a VL-CDR3 having the amino acid sequence of SEQ ID NO:32 and a VL-CDR2 having the amino acid sequence of SEQ ID NO:31. In other aspects, the LOX1-binding protein comprises a VL-CDR3 having the amino acid sequence of SEQ ID NO:32, a VL-CDR2 having the amino acid sequence SEQ ID NO:31 and a VL-CDR1 having the amino acid sequence of SEQ ID NO:30. In other aspects, the LOX1-binding protein comprises a VL-CDR3 having the amino acid sequence of SEQ ID NO:32, 34, or 35, a VL-CDR2 having the amino acid sequence SEQ ID NO:31. In further aspects, the LOX1-binding protein comprises a VL-CDR3 having the amino acid sequence of SEQ ID NO:32, 34, or 35, a VL-CDR2 having the amino acid sequence SEQ ID NO:31 and a VL-CDR1 having the amino acid sequence of SEQ ID NO:30. The disclosure also provides nucleic acids encoding the LOX1-binding protein, vectors containing these nucleic acids and host cells transformed with these nucleic acids and vectors, and methods of making and using the LOX1-binding protein.

In additional aspects, the LOX1-binding protein comprises one, two, or three VH-CDRs such as a VH-CDR1 identical to, or that has a total of one, two or fewer amino acid substitutions, deletions, or insertions to SEQ ID NO:1, a VH-CDR2 identical to, or that has a total of one, two or fewer amino acid substitutions, deletions, or insertions to SEQ ID NO:2, 5-12 or 13, or a VH-CDR3 identical to, or that has a total of one, two, three, four, or fewer amino acid substitutions, deletions, or insertions to SEQ ID NO:3, 14-17 or 18.

In additional aspects, the LOX1-binding protein comprises one, two, or three VL-CDRs such as a VL-CDR1 identical to, or that has a total of one, two or fewer amino acid substitutions, deletions, or insertions to SEQ ID NO:30, a VL-CDR2 identical to, or that has a total of one, two or fewer amino acid substitutions, deletions, or insertions to SEQ ID NO:31, or a VH-CDR3 identical to, or that has a total of one, two, three, four, or fewer amino acid substitutions, deletions, or insertions to SEQ ID NO:32, 34, or 35.

In some aspects the isolated LOX1-binding protein comprises a VH sequence that has a total of one, two, three, four, five, six, seven, eight or fewer amino acid substitutions, deletions and/or insertions from a reference VH sequence of SEQ ID NO:41. The disclosure also provides nucleic acids encoding the LOX1-binding protein, vectors containing these nucleic acids and host cells transformed with these nucleic acids and vectors, and methods of making and using the LOX1-binding protein.

In further aspects, the isolated LOX1-binding protein comprises a VH of SEQ ID NO:41. The disclosure also provides nucleic acids encoding the LOX1-binding proteins, vectors containing these nucleic acids and host cells transformed with these nucleic acids and vectors, and methods of making an using the LOX1-binding proteins.

In some aspects the isolated LOX1-binding protein comprises a VL sequence that has a total of one, two, three, four, five, six, seven, eight or fewer amino acid substitutions, deletions and/or insertions from a reference VL sequence of SEQ ID NO:58. The disclosure also provides nucleic acids encoding the LOX1-binding protein, vectors containing these nucleic acids and host cells transformed with these nucleic acids and vectors, and methods of making and using the LOX1-binding protein.

In further aspects, the isolated LOX1-binding protein comprises a VL of SEQ ID NO:58. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a VH selected from a VH containing a VH-CDR1 having the amino acid sequence of SEQ ID NO:38, a VH-CDR2 having the amino acid sequence of SEQ ID NO:39, 42 or 43, and a VH-CDR3 having the amino acid sequence of SEQ ID NO:40, 44-46 or 47; and a light chain VL selected from a VL containing a VL-CDR1 having the amino acid sequence of SEQ ID NO:55 or 59, a VL-CDR2 having the amino acid sequence of SEQ ID NO:56 or 60, and a VL-CDR3 having the amino acid sequence of SEQ ID NO:57, 61-63, or 64.

In some aspects, the isolated LOX1-binding protein has a VH comprising a sequence of SEQ ID NO:41, 48-53, or 54, and a VL comprising a sequence of SEQ ID NO:58, 65-69, or 70. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein comprises a set of complementary determining regions (CDRs): heavy chain variable region (VH)-CDR1, VH-CDR2, VH-CDR3, light chain variable region (VL)-CDR1, VL-CDR2 and VL-CDR3 wherein the set of CDRs is identical to, or has a total of one, two, three, four, five, six, seven, eight or fewer amino acid substitutions, deletions, and/or insertions from a reference set of CDRs in which: (a) VH-CDR1 has the amino acid sequence of SEQ ID NO:38; (b) VH-CDR2 has the amino acid sequence of SEQ ID NO:39; (c) VH-CDR3 has the amino acid sequence of SEQ ID NO:44; (d) VL-CDR1 has the amino acid sequence of SEQ ID NO:55; (e) VL-CDR2 has the amino acid sequence of SEQ ID NO:60; and (f) VL-CDR3 has the amino acid sequence of SEQ ID NO:61. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein comprises a set of complementary determining regions (CDRs): heavy chain variable region (VH)-CDR1, VH-CDR2, VH-CDR3, light chain variable region (VL)-CDR1, VL-CDR2 and VL-CDR3 wherein the set of CDRs is identical to, or has a total of one, two, three, four, five, six, seven, eight or fewer amino acid substitutions, deletions, and/or insertions from a reference set of CDRs in which: (a) VH-CDR1 has the amino acid sequence of SEQ ID NO:38, (b) VH-CDR2 has the amino acid sequence of SEQ ID NO:39; (c) VH-CDR3 has the amino acid sequence of SEQ ID NO:40; (d) VL-CDR1 has the amino acid sequence of SEQ ID NO:55; (e) VL-CDR2 has the amino acid sequence of SEQ ID NO:56; and (f) VL-CDR3 has the amino acid sequence of SEQ ID NO:57. The disclosure also provides nucleic acids encoding the LOX1-binding protein, vectors containing these nucleic acids and host cells transformed with these nucleic acids and vectors, and methods of making and using the LOX1-binding protein.

In further aspects, the LOX1-binding protein comprises a set of CDRs: VH-CDR1, VH-CDR2, VH-CDR3, VL-CDR1, VL-CDR2 and VL-CDR3 wherein: (a) VH-CDR1 has the amino acid sequence of SEQ ID NO:38; (b) VH-CDR2 has the amino acid sequence of SEQ ID NO:39; (c) VH-CDR3 has the amino acid sequence of SEQ ID NO:40; (d) VL-CDR1 has the amino acid sequence of SEQ ID NO:55; (e) VL-CDR2 has the amino acid sequence of SEQ ID NO:56; and (f) VL-CDR3 has the amino acid sequence of SEQ ID NO:57. The disclosure also provides nucleic acids encoding the LOX1-binding protein, vectors containing these nucleic acids and host cells transformed with these nucleic acids and vectors, and methods of making and using the LOX1-binding protein.

In further aspects, the isolated LOX1-binding protein comprising a VH-CDR3 having the amino acid sequence of SEQ ID NO:40. In further aspects, the LOX1-binding protein comprises a VH-CDR3 having the amino acid sequence of SEQ ID NO:40 and a VH-CDR2 having the amino acid sequence of SEQ ID NO:39. In other aspects, the LOX1-binding protein comprises a VH-CDR3 having the amino acid sequence of SEQ ID NO:40 and a VH-CDR2 having the amino acid sequence of SEQ ID NO:42 or 43. In additional aspects, the LOX1-binding protein comprises a VH-CDR3 having the amino acid sequence of SEQ ID NO:40, 44-46, or 47 and a VH-CDR2 having the amino acid sequence of SEQ ID NO:39. In further aspects, the LOX1-binding protein comprises a VH-CDR3 having the amino acid sequence of SEQ ID NO: 40, 44-46, or 47 and a VH-CDR2 having the amino acid sequence of SEQ ID NO:39, 42, or 43. In further aspects, the LOX1-binding protein comprises a VH-CDR3 having the amino acid sequence of SEQ ID NO: 40, 44-46, or 47 and a VH-CDR2 having the amino acid sequence of SEQ ID NO: 39, 42, or 43, and a VH-CDR1 having the amino acid sequence of SEQ ID NO:38. The disclosure also provides nucleic acids encoding the LOX1-binding protein, vectors containing these nucleic acids and host cells transformed with these nucleic acids and vectors, and methods of making and using the LOX1-binding protein.

In further aspects, the isolated LOX1-binding protein comprises a VLH-CDR3 having the amino acid sequence of SEQ ID NO:57. In further aspects, the LOX1-binding protein comprises a VL-CDR3 having the amino acid sequence of SEQ ID NO:57 and a VL-CDR2 having the amino acid sequence of SEQ ID NO:56. In other aspects, the LOX1-binding protein comprises a VL-CDR3 having the amino acid sequence of SEQ ID NO:57, a VL-CDR2 having the amino acid sequence SEQ ID NO:56 and a VL-CDR3 having the amino acid sequence of SEQ ID NO:55. In other aspects, the LOX1-binding protein comprises a VL-CDR3 having the amino acid sequence of SEQ ID NO:57, a VL-CDR2 having the amino acid sequence SEQ ID NO:56 or 60, and a VL-CDR1 having the amino acid sequence of SEQ ID NO:55 or 59. The disclosure also provides nucleic acids encoding the LOX1-binding protein, vectors containing these nucleic acids and host cells transformed with these nucleic acids and vectors, and methods of making and using the LOX1-binding protein.

In additional aspects, the LOX1-binding protein comprises one, two, or three VH-CDRs such as a VH-CDR1 identical to, or that has a total of one, two or fewer amino acid substitutions, deletions, or insertions to SEQ ID NO:38, a VH-CDR2 identical to, or that has a total of one, two or fewer amino acid substitutions, deletions, or insertions to SEQ ID NO:39, 42 or 43, or a VH-CDR3 identical to, or that has a total of one, two, three, four, or fewer amino acid substitutions, deletions, or insertions to SEQ ID NO:40, 44-46 or 47. The disclosure also provides nucleic acids encoding the LOX1-binding protein, vectors containing these nucleic acids and host cells transformed with these nucleic acids and vectors, and methods of making and using the LOX1-binding protein.

In additional aspects, the LOX1-binding protein comprises one, two, or three VL-CDRs such as a VL-CDR1 identical to, or that has a total of one, two or fewer amino acid substitutions, deletions, or insertions to SEQ ID NO: 55 or 59, a VL-CDR2 identical to, or that has a total of one, two or fewer amino acid substitutions, deletions, or insertions to SEQ ID NO:56 or 60, or a VH-CDR3 identical to, or that has a total of one, two, three, four, or fewer amino acid substitutions, deletions, or insertions to SEQ ID NO: 57, 61-63 or 64. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a set of CDRs: VH-CDR1, VH-CDR2, VH-CDR3, VL-CDR1, VL-CDR3 and VL-CDR3 as described in Table 1. The disclosure also provides nucleic acids encoding the LOX1-binding protein, vectors containing these nucleic acids and host cells transformed with these nucleic acids and vectors, and methods of making and using the LOX1-binding protein.

In some additional aspects, the LOX1-binding protein comprises a heavy chain variable region (VH) and light chain variable region (VL) as described in Table 1. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein comprises a VH-CDR2 having the amino acid sequence of G F D P E D $HX_1$ $HX_2$ $HX_3$ $HX_4$ $HX5$ $HX_6$ Q K F Q G (Gly Phe Asp Pro Glu Asp $HX_1$ $HX_2$ $HX_3$ $HX_4$ $HX_5$ $HX_6$ Gln Lys Phe Gln Gly), wherein $HX_1$ is Gly, Trp, Tyr, or Phe; $HX_2$ is Glu, Thr, Gln, Ser, Lys, or Ala; $HX_3$ is Thr, Tyr, Ile, or Asn; $HX_4$ is Ile, Ala, Arg, or His; $HX_5$ is Tyr, Val, Thr, Leu, or Gln, and $HX_6$ is Ala, Asp, Gly, Ser, or His (SEQ ID NO:71).

In additional aspects, the isolated LOX1-binding protein comprises a VH-CDR3 having the amino acid sequence of $HX_7$ $HX_8$ G $HX_9$ $HX_{10}$ $HX_{11}$ $HX_{12}$ G V R G W D Y Y Y G M D V ($HX_7$ $HX_8$ Gly $HX_9$ $HX_{10}$ $HX_{11}$ $HX_{12}$ Gly Val Arg Gly Trp Asp Tyr Tyr Tyr Gly Met Asp Val Trp) wherein $HX_7$ is Pro, Ser, or Val; $HX_8$ is Asn, Thr, Trp, or Asp; $HX_9$ is Gln, Arg, or Thr; $HX_{10}$ is Gln or His; $HX_{11}$ is Gly or Gln; $HX_{12}$ is Lys or Gly (SEQ ID NO:72).

In other aspects, the isolated LOX1-binding protein comprises a VL-CDR3 having the amino acid sequence of Q S Y D S $LX_1$ $LX_2$ $LX_3$ $LX_4$ $LX_5$ $LX_6$ (Gln Ser Tyr Asp Ser $LX_1$ $LX_2$ $LX_3$ $LX_4$ $LX_5$ $LX_6$), wherein $LX_1$ is Ser or Met; $LX_2$ is Leu, Tyr, or His; $LX_3$ is Ser or Arg; $LX_4$ is Gly, Ala, or no amino acid; $LX_5$ is Trp or Phe; and $LX_6$ is Val, Gly, or Ala (SEQ ID NO:73).

In some aspects, the isolated LOX1-binding protein comprises a set of complementary determining regions (CDRs): heavy chain variable region (VH)-CDR1, VH-CDR2, VH-CDR3, and light chain variable region (VL)-CDR1, VL-CDR2 and VL-CDR3 wherein: (a) VH-CDR1 comprises the amino acid sequence: E L S M H (SEQ ID NO: 1); (b) VH-CDR2 comprises the amino acid sequence: G F D P E D $HX_1$ $HX_2$ $HX_3$ $HX_4$ $HX_5$ $HX_6$ Q K F Q G, wherein HX1 is selected from the group consisting of G, W, Y and F, HX2 is selected from the group consisting of E, T, Q, K, A, and S, HX3 is selected from the group consisting of T, Y, I, and N, HX4 is selected from the group consisting of I, A, R and H, HX5 is selected from the group consisting of Y, V, T, L and Q, and HX6 is selected from the group consisting of A, D, G, S and H (SEQ ID NO: 71); (c) VH-CDR3 comprises the amino acid sequence: $HX_7$ $HX_8$ G $HX_9$ $HX_{10}$ $HX_{11}$ $HX_{12}$ GVRGWDYYYGMD V, wherein $HX_7$ is selected from the group consisting of P, S and V, $HX_8$ is selected from the group consisting of N, W, D, and T, HX9 is selected from the group consisting of Q, R and T, HX10 is selected from the group consisting of Q and H, HX11 is selected from the group consisting of G and Q, and HX12 is selected from the group consisting of K and G (SEQ ID NO: 72); (d) VL-CDR1 comprises the amino acid sequence: T G S S S N I G A G Y D V H (SEQ ID NO: 30); (e) VL-CDR2 comprises the amino acid sequence: G N S N R P S (SEQ ID NO: 31); and (f) VL-CDR3 comprises the amino acid sequence: QS YDS $LX_1$ $LX_2$ $LX_3$ $LX_4$ $LX5$ $LX6$, wherein LX1 is selected from the group consisting of M and S, LX2 is selected from the group consisting of L, Y and H, LX3 is selected from the group consisting of S and R, LX4 is selected from the group consisting of A and G or is omitted (no amino acid), LX5 is selected from the group consisting of W and F, and LX6 is selected from the group consisting of V, G and A (SEQ ID NO: 73).

In additional aspects, the isolated LOX1-binding protein comprises a VH-CDR2 having the amino acid sequence of G $HX_1$ S $HX_2$ $HX_3$ $HX_4$ $HX_{c5}$ HX6 $HX_7$ $HX_8$ $HX_9$ $HX_{10}$ D S V K G (Gly $HX_1$ Ser $HX_2$ $HX_3$ $HX_4$ $HX_5$ $HX_6$ $HX_7$ $HX_8$ $HX_9$ $HX_{10}$ Asp Ser Val Lys Gly), wherein $HX_1$ is Be or Val; $HX_2$ is Trp or Leu; $HX_3$ is Asn or Gln; $HX_4$ is Ser or Glu; $HX_5$ is Gly, Leu, or Pro; $HX_6$ is Ser, Tyr, or Asp; $HX_7$ is Ile, Thr, or Arg; $HX_8$ is Gly or Tyr; $HX_9$ is Tyr or Met; and $HX_{10}$ is Ala or Asp (SEQ ID NO:74).

In additional aspects, the isolated LOX1-binding protein comprises a VH-CDR3 having the amino acid sequence of E G $HX_{11}$ W N Y D A $HX_{12}$ D $HX_{13}$ (Glu Gly $HX_{11}$ Trp Asn Tyr Asp Ala $HX_{12}$ Asp $HX_{13}$), wherein $HX_{11}$ is Asn or Ser; $HX_{12}$ is Phe or Leu; and $HX_{13}$ is Be or Val (SEQ ID NO:75).

In additional aspects, the isolated LOX1-binding protein comprises a VL-CDR1 having the amino acid sequence of T G T S $LX_1$ D V G G Y NY V S (Thr Gly Thr Ser $LX_1$ Asp Val Gly Gly Tyr Asn Tyr Val Ser), wherein $LX_1$ is Ser or Asn (SEQ ID NO:76).

In additional aspects, the isolated LOX1-binding protein comprises a VL-CDR2 having the amino acid sequence of D V S $LX_2$ R P S (Asp Val Ser X4 Arg Pro Ser), wherein $LX_2$ is Asn or Lys (SEQ ID NO:77).

In additional aspects, the isolated LOX1-binding protein comprises a VL-CDR3 having the amino acid sequence of $LX_3$ $LX_4$ $LX_5$ $LX_6$ $LX_7$ $LX_8$ S T N W V ($LX_3$ $LX_4$ $LX_5$ $LX_6$ $LX_7$ $LX_8$ Ser Thr Asn Trp Val), wherein $LX_3$ is Ser, Leu, Met, or Ala; $LX_4$ is Ser, Gly, or Gln; $LX_5$ is Tyr, Arg, Ser, or Gly; $LX_6$ is Thr or Met; $LX_7$ is Ser, Trp, Gly, or Val; and $LX_8$ is Ser or Arg (SEQ ID NO:78).

In some aspects, the isolated LOX1-binding protein comprises a set of complementary determining regions (CDRs): heavy chain variable region (VH)-CDR1, VH-CDR2, VH-CDR3, and light chain variable region (VL)-CDR1, VL-CDR2 and VL-CDR3 wherein: (a) VH-CDR1 comprises the amino acid sequence: D Y A MH (SEQ ID NO: 38); (b) VH-CDR2 comprises the amino acid sequence: G $HX_1$ S $HX_2$ $HX_3$ $HX_4$ $HX_5$ $HX_6$ $HX_7$ $HX_8$ $HX_9$ $HX_{10}$ DS V K G, wherein HX1 is selected from the group consisting of I and V, HX2 is selected from the group consisting of W and L, HX3 is selected from the group consisting of N and Q, HX4 is selected from the group consisting of S and E, HX5 is selected from the group consisting of G, L and P, HX6 is selected from the group consisting of S, Y and D, HX7 is selected from the group consisting of I, T and R, HX8 is selected from the group consisting of G and Y, HX9 is selected from the group consisting of M and Y, and HX10 is selected from the group consisting of A and D (SEQ ID NO:74); (c) VH-CDR3 comprises the amino acid sequence: E G $HX_{11}$ W N Y D A $HX_{12}$ D $HX_{13}$, wherein HX11 is selected from the group consisting of N and S, HX12 is selected from the group consisting of F and L, and HX13 is selected from the group consisting of I and V (SEQ ID NO:75); (d) VL-CDR1 comprises the amino acid sequence: T G T S $LX_1$ D V G G Y N Y V 5, wherein LX1 is selected from the group consisting of N and S (SEQ ID NO:76); (e) VL-CDR2 comprises the amino acid sequence: D V S $LX_2$ R P S, wherein LX2 is selected from the group consisting of N and K (SEQ ID NO:77); and (f) VL-CDR3 comprises the amino acid sequence: $LX_3$ $LX_4$ $LX_5$ $LX_6$ $LX_7$ $LX_8$ S T N W V, wherein LX3 is selected from the group consisting of L, M, A and S, LX4 is selected from the group consisting of S, Q and G, LX5 is selected from the group consisting of Y, S, G and R, LX6 is selected from the group consisting of T and M, LX7 is selected from the group consisting of S, W, G and V, and LX8 is selected from the group consisting of S and R (SEQ ID NO:78).

In some aspects, the set of CDRs of a LOX1-binding protein disclosed herein is provided within antibody framework regions or other protein scaffolds known in the art. Exemplary antibody framework regions include: germline framework regions, such as VH1-24 (DP-5), JH6, VH3-09 (DP-31), and JH3 for the antibody framework region of the heavy chain and Vλ1e (DPL-8), Vλ2a2 (DPL-11), and JL3 for the antibody framework region of the light chain and/or any suitable framework regions well known to one of skilled in the art.

In some aspects, the LOX1-binding protein contains one or more framework regions from a heavy chain variable region (VH) and/or a light chain variable region (VL) that is a germline framework. Frameworks regions of the heavy chain domain may be selected from VH1-24 (DP-5), JH6, VH3-09 (DP-31), JH3 frameworks and/or any suitable framework regions or protein scaffolds well known in the art. Framework regions of the light chain may be selected from Vλ1e (DPL-8), VX2a2 (DPL-11), and JL3 frameworks, and/or any suitable framework regions or protein scaffolds well known in the art. One or more CDRs may be taken from the LOX1-binding proteins disclosed herein (e.g. a LOX1-binding protein described in Table 1) and incorporated into a suitable framework and/or protein scaffold.

In additional aspects, the disclosure provides an isolated LOX1-binding protein that binds to the same LOX1 epitope as an antibody comprising a VH and VL of SEQ ID NO:4 and SEQ ID NO:33, respectively.

In other aspects, the methods disclosed herein include LOX1-binding proteins (e.g., antibodies such as, full length LOX1-antibodies, LOX1-binding antibody fragments, and variants and derivatives thereof) that compete or cross-competes for binding to LOX1 with an antibody comprising a VH sequence of SEQ ID NO:4 and a VL sequence of SEQ ID NO:33. In a particular aspect, the LOX1-binding protein is able to competitively inhibit an antibody comprising a VH of SEQ ID NO:4 and a VL of SEQ ID NO:33, to bind to LOX1.

Also provided are methods including a LOX1-binding protein such as, a LOX1 antibody (e.g., a full length anti-LOX1 antibody, a LOX1-binding antibody fragment, and variants, and derivatives thereof) which can bind to LOX1 with a greater affinity than a LOX1-binding protein (e.g. a LOX1 antibody or fragment thereof) comprising the VH of SEQ ID NO:29 and the VL of SEQ ID NO:33. The disclosure also provides nucleic acids encoding the LOX1-binding protein, vectors containing these nucleic acids and host cells transformed with these nucleic acids and vectors, and methods of making and using the LOX1-binding protein.

In additional aspects, the methods include an isolated LOX1-binding protein that binds to the same LOX1 epitope as an antibody comprising a VH and VL of SEQ ID NO:41 and SEQ ID NO:58, respectively.

In other aspects, the methods include LOX1-binding proteins (e.g., antibodies such as, full length LOX1-antibodies and LOX1-binding antibody fragments, and variants and derivatives thereof) that compete or cross-competes for binding to LOX1 with an antibody comprising a VH sequence of SEQ ID NO:41 and a VL sequence of SEQ ID NO:58. In a particular aspect, the LOX1-binding protein is able to competitively inhibit an antibody comprising a VH of SEQ ID NO:41 and a VL of SEQ ID NO:58 to bind to LOX1.

Also provided are methods including a LOX1-binding protein such as, a LOX1 antibody (e.g., a full length anti-LOX1 antibody and a LOX1-binding antibody fragment, and variants, and derivatives thereof), which can bind to LOX1 with a greater affinity than a full-length antibody comprising the VH of SEQ ID NO:54 and the VL of SEQ ID NO:70. The disclosure also provides nucleic acids encoding the LOX1-binding protein, vectors containing these nucleic acids and host cells transformed with these nucleic acids and vectors, and methods of making and using the LOX1-binding protein.

In some aspects, the anti-LOX1 antibody incorporated into the methods discussed herein is a murine antibody, a human antibody, a humanized antibody, a chimeric antibody, a monoclonal antibody, a polyclonal antibody, a recombinant antibody, a bi-specific antibody, a multispecific antibody, or any combination thereof. In some aspects the anti-LOX1 antibody is an Fv fragment, an Fab fragment, an F(ab')2 fragment, an Fab' fragment, a dsFv fragment, an scFv fragment, or an sc(Fv)2 fragment.

The disclosure includes methods comprising a LOX1-binding protein (e.g., an isolated anti-LOX1 antibody such as, a full length LOX1-antibody, a LOX1-binding antibody fragment, and a variant and derivative thereof) that can bind to LOX1 molecules across species. In some aspects, the LOX1-binding protein binds to human LOX1 (hLOX1) and cynomolgus LOX1 (cynoLOX1). In additional aspects, the LOX1-binding protein binds to human LOX1 (hLOX1) and rabbit LOX1. In further aspects, the LOX1-binding protein binds to hLOX1, cynoLOX1 and rabbit LOX1. In certain aspects provided herein, a LOX1-binding protein (e.g., an anti-LOX1 antibody) specifically binds to LOX1 (e.g., hLOX1, cynoLOX1 and/or rabbit LOX1) and does not bind to one or more of: CLEC-7A, CLEC-1A, CLEC-4L, CLEC-1B, SR-A1 and/or SR-B3. See, e.g., International Patent Application No. PCT/EP2015/072644.

In some aspects, the LOX1-binding protein (e.g., an isolated anti-LOX1 antibody or thereof) further comprises a human IgG1 TM mutant heavy chain, wherein the heavy chain variable region (VH) comprises an amino acid sequence having at least 70%, 75%, 80%, 85%, 90%, 95%, 96%, 97%, 98% 99%, or 100% sequence identity to the reference amino acid sequence SEQ ID NO:4, 19-28 or 29.

In some aspects, the LOX1-binding protein (e.g., an isolated anti-LOX1 antibody or thereof) further comprises a human IgG1 TM mutant heavy chain, wherein the heavy chain variable region (VH) comprises an amino acid sequence having at least 70%, 75%, 80%, 85%, 90%, 95%, 96%, 97%, 98% 99%, or 100% sequence identity to the reference amino acid sequence SEQ ID NO:41, 48-53 or 54.

In some aspects, the LOX1-binding protein (e.g., a full length LOX1-antibody, a LOX1-binding antibody fragment, and a variant and derivative thereof) includes in addition to a heavy chain variable region (VH) and a light chain variable region (VL), and optionally a heavy chain constant region or fragment thereof, a light chain constant region or fragment thereof. In certain aspects the light chain constant region is a kappa lambda light chain constant region, e.g., a human kappa constant region or a human lambda constant region. In a specific aspect, the light chain constant region is a human kappa constant region.

In additional aspects, the LOX1-binding protein (e.g., a full length LOX1-antibody, a LOX1-binding antibody fragment, and a variant and derivative thereof) has a light chain variable region (VL) that contains a human kappa constant region, e.g., the VL comprises a VL amino acid sequence having at least 70%, 75%, 80%, 85%, 90%, 95%, or 100% sequence identity to the reference amino acid sequence SEQ ID NO:33, 36, or 37. In certain aspects, the disclosure provides a LOX1-binding protein (e.g., an anti-LOX1 antibody or fragment thereof) further comprising a human IgG1 TM mutant heavy chain and a human kappa light chain, wherein the heavy chain variable region (VH) and the light chain variable region (VL) comprise: SEQ ID NO:4 and SEQ ID NO:33; SEQ ID NO:29 and SEQ ID NO:33; SEQ ID NO:41 and SEQ ID NO:58; or SEQ ID NO:54 and SEQ ID NO:70, respectively.

In additional aspects, the LOX1-binding protein (e.g., a full length LOX1-antibody, a LOX1-binding antibody fragment, and a variant and derivative thereof) has a light chain variable region (VL) that further comprises a human kappa constant region, e.g., the light chain can comprise a light chain amino acid sequence having at least 70%, 75%, 80%, 85%, 90%, 95%, or 100% sequence identity to the reference amino acid sequence SEQ ID NO:58, 65-69 or 70. In certain aspects, the disclosure provides a LOX1-binding protein (e.g., an anti-LOX1 antibody or fragment thereof) further comprising a human IgG1 TM mutant heavy chain and a human kappa light chain, wherein the heavy chain variable region (VH) and the light chain variable region (VL) comprise: SEQ ID NO:41 and SEQ ID NO:58, SEQ ID NO:48 and SEQ ID NO:65, SEQ ID NO:49 and SEQ ID NO:66, SEQ ID NO:50 and SEQ ID NO:67, or SEQ ID NO:53 and SEQ ID NO:58, respectively.

In some aspects, the disclosure relates to methods comprising an isolated LOX1-binding protein such as an anti-LOX1 antibody (e.g., a full length LOX1-antibody, a LOX1-binding antibody fragment, and a variant and derivative thereof), wherein the LOX1-binding protein has at least one property selected from the group consisting of: (a) reduces or inhibits binding of oxLDL, C-reactive protein (CRP) and/or advanced glycation end products (AGEs) to LOX1 as determined by any suitable assay; (b) decreases or inhibits RhoA/Rac1, nitrogen monoxide (NO), p38MAPK, protein kinase B and C, ERK1/2, and/or NFκB signaling in an endothelial cell expressing cell surface LOX1 as determined by any suitable assay; (c) decreases or inhibits caspase-8, caspase-9, and/or BAX activity in an endothelial cell expressing cell surface LOX1 as determined by any suitable assay including an assay disclosed herein; (d) binds to LOX1 having the single nucleotide polymorphism K167N as determined by any suitable assay; (e) reduces or inhibits oxLDL internalization as determined by any suitable assay; (f) reduces or inhibits oxLDL-induced LOX1 signaling as determined by any suitable assay; (g) binds to LOX1 with a dissociation constant (KD) of about 150 pM to about 600 pM (e.g. about 400 pM) as determined by BIACORE or KinExA; (h) binds to LOX1 with a $K_{on}$ rate of about $1 \times 10^5$ $M^{-1}$ $s^{-1}$ to about $6 \times 10^6$ $M^{-1}$ $s^{-1}$ (e.g. about $5 \times 10^5$ $M^{-1}$ $s^{-1}$) as determined by BIACORE; and (i) binds to LOX1 with a $K_{off}$ rate of about $1 \times 10^{-4}$ $s^{-1}$ to about $3 \times 10^{-4}$ $s^{-1}$ (e.g. about $2.3 \times 10^{-4}$ $s^{-1}$) as determined by BIACORE.

In certain embodiments, in addition to, or as an alternative to, the above identified properties the LOX1-binding protein has at least one property selected from the group consisting of: (a) killing a CSC; (b) eliminating a CSC; (c) inhibiting a CSC; (d) reducing the progression and/or rate of progression of CSC proliferation; (e) reducing the progression and/or rate of progression of a disease state associated with a CSC; (f) reducing the ability for self-renewal and expansion of a CSC; and/or (g) inducing CSC differentiation.

In certain aspects, a LOX1-binding protein such as, an anti-LOX1 antibody, a full length LOX1-antibody, a LOX1-binding antibody fragment, and a variant and derivative thereof) can specifically bind to LOX1, e.g., human LOX1 (hLOX1) and/or cynomolgus LOX1 (cynoLOX1), and antigenic fragments thereof with a dissociation constant or $K_D$ of less than $10^{-6}$ M, or of less than $10^{-7}$ M, or of less than $10^{-8}$ M, or of less than $10^{-9}$ M, or of less than $10^{-10}$ M, or of less than $10^{-11}$ M, of less than $10^{-12}$ M, of less than $10^{-13}$ M, of less than $10^{-14}$ M, or of less than $10^{-15}$ M as measured, e.g., by KINEXA® or BIACORE®. In one aspect, the anti-LOX1 antibody can bind to hLOX1 and cynoLOX1 with a $K_D$ of less than about $1 \times 10^{-8}$ M to about $1 \times 10^{-10}$ M as measured by BIACORE®.

In another aspect, a LOX1-binding protein such as, an anti-LOX1 antibody (e.g., a full length LOX1-antibody, a LOX1-binding antibody fragment, and a variant and derivative thereof) can bind to LOX1 with a $K_{off}$ of less than $1 \times 10^{-3}$ $s^{-1}$, or less than $2 \times 10^{-3}$ $s^{-1}$. In other aspects, the LOX1-binding protein binds to LOX1 with a $K_{off}$ of less than $10^{-3}$ $s^{-1}$, less than $5 \times 10^{-3}$ $s^{-1}$, less than $10^{-4}$ $s^{-1}$, less than $5 \times 10^{-4}$ $s^{-1}$, less than $10^{-5}$ $s^{-1}$, less than $5 \times 10^{-5}$ $s^{-1}$, less than $10^{-6}$ $s^{-1}$, less than $5 \times 10^{-6}$ $s^{-1}$, less than less than $5 \times 10^{-7}$ $s^{-1}$, less than $10^{-8}$ $s^{-1}$, less than $5 \times 10^{-8}$ $s^{-1}$, less than $10^{-9}$ $s^{-1}$, less than $5 \times 10^{-9}$ $s^{-1}$, or less than $10^{-10}$ $s^{-1}$ as measured, e.g., by KINEXA® or BIACORE®. In one aspect, the anti-LOX1 antibody can bind to hLOX1 and cynLOX1 with a $K_{off}$ of 1 to $10 \times 10^{-4}$ $s^{-1}$ as measured by BIACORE®.

In another aspect, a LOX1-binding protein such as, an anti-LOX1 antibody (e.g., a full length LOX1-antibody, a LOX1-binding antibody fragment, and a variant and derivative thereof) can bind to LOX1, e.g., human LOX1 (h LOX1) and/or cynomolgus LOX1, with an association rate constant or $k_{on}$ rate of at least $10^5$ $M^{-1}$ $s^{-1}$, at least $5 \times 10^5$ $M^{-1}$ $s^{-1}$, at least $10^6$ $M^{-1}$ $s^{-1}$, at least $5 \times 10^6$ $M^{-1}s^{-1}$ at least $10^7$ $M^{-1}$ $s^{-1}$, at least $5 \times 10^7$ $M^{-1}$ $s^{-1}$, or at least $10^8$ $M^{-1}$ $s^{-1}$, or at least $10^9$ $M^{-1}$ $s^{-1}$ as measured, e.g., by KINEXA® or BIACORE®. In one aspect, the anti-LOX1 antibody can bind to hLOX1 and cynLOX1 with a $k_{on}$ rate of about $1 \times 10^5$ $M^{-1}$ $s^{-1}$ to about $20 \times 10^5$ $M^{-1}$ $s^{-1}$ as measured by BIACORE®.

As noted above, a LOX1-binding protein (e.g., a full length LOX1-antibody, a LOX1-binding antibody fragment, and a variant and derivative thereof) containing a VH and/or VL amino acid sequence that binds LOX1 can have at least 85%, 90%, 95%, 96%, 97%, 98% or 99% sequence identity to a sequence set forth herein (see, e.g., Table 1). In some aspects, the VH and/or VL amino acid sequence(s) that binds LOX1 comprise 15 or fewer (e.g., 1, 2, 3, 4, 5, 6, 7, 8, 9, 10, 11, 12, 13, 14 or 15) amino acid additions, substitutions (e.g., conservative substitutions) or deletions relative to a sequence set forth herein. In some aspects, the VH and/or VL amino acid sequence(s) that binds LOX1 comprise 8 or fewer (e.g., 1, 2, 3, 4, 5, 6, 7 or 8) amino acid additions, substitutions (e.g., conservative substitutions) or deletions relative to a sequence set forth herein. In additional aspects, the VH and/or VL amino acid sequence that binds LOX1 comprise 5 or fewer (e.g., 1, 2, 3, 4 or 5) amino acid additions, substitutions (e.g., conservative substitutions) or deletions relative to a sequence set forth herein. A LOX1-binding protein (e.g. an anti-LOX1 antibody or fragment thereof) containing VH and VL regions having a certain percent similarity to a VH region or VL region, or having one or more substitutions, deletions and/or insertions (e.g., conservative substitutions) can be obtained by mutagenesis (e.g., site-directed or PCR-mediated mutagenesis) of nucleic acid molecules encoding VH and/or VL regions described herein, followed by testing of the encoded altered antibody for binding to LOX1 and optionally testing for retained function using the functional assays described herein or an assay known in the art that can be routinely modified to test the retained function.

The affinity or avidity of a LOX1-binding protein such as, an anti-LOX1 antibody (e.g., a full length LOX1-antibody, a LOX1-binding antibody fragment, and a variant and derivative thereof), for LOX1 can be determined experimentally using any suitable method known in the art, e.g., flow cytometry, enzyme-linked immunosorbent assay (ELISA), or radioimmunoassay (RIA), or kinetics (e.g., KINEXA® or BIACORE® analysis). Direct binding assays as well as competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein). The measured affinity of a particular antibody-antigen interaction can vary if measured under different conditions (e.g., salt concentration, pH, temperature). Thus, measurements of affinity and other LOX1-binding parameters (e.g., $K_D$ or Kd, $K_{on}$, $K_{off}$) are made with standardized solutions of LOX1-binding proteins and LOX1, and a standardized buffer, as known in the art.

The disclosure further provides a LOX1-binding protein such as, an anti-LOX1 antibody (e.g., a full length LOX1-antibody, a LOX1-binding antibody fragment, and a variant and derivative thereof), as described herein (see, e.g., Table 1), wherein the antibody is conjugated to a heterologous agent. In certain aspects the agent is an antimicrobial agent, a therapeutic agent, a prodrug, a peptide, a protein, an enzyme, a lipid, a biological response modifier, a pharmaceutical agent, a lymphokine, a heterologous antibody or antibody fragment, a detectable label, or a polyethylene glycol (PEG). Heteroconjugate LOX1-binding proteins can be prepared as discussed in more detail in International Patent Application No. PCT/EP2015/072644, which is incorporated by reference herein in its entirety.

In certain aspects, the LOX1-binding protein is not an anti-LOX1 antibody. A variety of methods for identifying and producing non-antibody polypeptides that bind with high affinity to a protein target are known in the art. See, e.g., Skerra, Curr. Opin. Biotech. 18:295-304 (2007), Hosse et al., Protein Science 15:14-27 (2006), Gill et al., Curr. Opin. Biotechnol. 17:653-658 (2006), Nygren, FEBS J. 275:2668-76 (2008), and Skerra, FEBS J. 275:2677-83 (2008), each of which is incorporated by reference herein in its entirety. In certain aspects, phage display technology can been used to identify/produce a LOX1-binding protein. In certain aspects, the polypeptide comprises a protein scaffold of a type selected from the group consisting of ankyrin, protein A, a lipocalin, a fibronectin domain, an ankyrin consensus repeat domain, and thioredoxin.

In certain aspects the methods may include LOX1 inhibitors (e.g., LOX1-binding proteins including antibodies such as, full length anti-LOX1 antibodies, LOX1-binding antibody fragments, and variants and derivatives thereof) that bind to the same epitope as one or more LOX1-binding proteins disclosed herein (see, e.g., Table 1). The term "epitope" as used herein refers to a target protein determinant capable of binding to an antibody of the disclosure. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. Such antibodies can be identified based on their ability to cross-compete (e.g., to competitively inhibit the binding of, in a statistically significant manner) with antibodies comprising a VH sequence of SEQ ID NO:4 and a VL sequence of SEQ ID NO:33, and/or antibodies comprising a VH sequence of SEQ ID NO:41 and a VL sequence of SEQ ID NO:58, in standard antigen-binding or activity assays.

The methods incorporating LOX1 inhibitors also include LOX1-binding proteins such as, anti-LOX1 antibodies (e.g., full length LOX1-antibodies, LOX1-binding antibody fragments, and variants and derivatives thereof), that bind the same epitope as an isolated LOX1-binding protein disclosed herein (see, e.g., Table 1).

The ability of a test LOX1-binding protein to inhibit the binding of, e.g., an antibody comprising a VH sequence of SEQ ID NO:4 and a VL sequence of SEQ ID NO:33 and/or antibodies comprising a VH sequence of SEQ ID NO:41 and a VL sequence of SEQ ID NO:58, demonstrates that the test LOX1-binding protein can compete with that antibody for binding to LOX1; such a LOX1-binding protein can, according to non-limiting theory, bind to the same or a related (e.g., a structurally similar or spatially proximal) epitope on LOX1 as the LOX1-binding proteins (e.g., anti-LOX1 antibodies such as, full length anti-LOX1 antibodies, LOX1-binding antibody fragments, and variants and derivatives thereof) with which it competes. In one aspect, the LOX1-binding protein binds to the same epitope on LOX1 as an antibody comprising a VH sequence of SEQ ID NO:4 and a VL sequence of SEQ ID NO:33. In another aspect, the LOX1-binding protein binds to the same epitope on LOX1 as an antibody comprising a VH sequence of SEQ ID NO:41 and a VL sequence of SEQ ID NO:58.

In one aspect, the disclosure provides LOX1-binding proteins (e.g., antibodies such as, full length LOX1-antibodies, LOX1-binding antibody fragments, and variants and derivatives thereof), that compete for binding to LOX1 with an antibody comprising a VH sequence of SEQ ID NO:4 and a VL sequence of SEQ ID NO:33. In another aspect, the disclosure provides LOX1-binding proteins (e.g., antibodies such as, full length LOX1-antibodies, LOX1-binding antibody fragments, and variants and derivatives thereof), that compete for binding to LOX1 with an antibody comprising a VH sequence of SEQ ID NO:41 and a VL sequence of SEQ ID NO:58.

In other embodiments, the inhibitor may be an antisense molecule comprising a polynucleotide which is complementary at least a portion of LOX1 mRNA. In some embodiments, the antisense molecule is suitable for use in method that inhibits translation of mRNA in a cell. The antisense molecule may comprise DNA, RNA, or both DNA and RNA, as well as chemically modified nucleic acids. Further, in some embodiments the antisense molecule may be single stranded or double stranded. An antisense molecule may comprise about 10 to about 500 nucleotides and, in some embodiments may have any number of lengths, for example, ranging from about 11 to about 200 nucleotides, about 12 to about 100 nucleotides, about 13 to about 75 nucleotides, about 14 to about 50 nucleotides, about 15 to about 40 nucleotides, about 16 to about 30 nucleotides, or about 17 to about 25 nucleotides. One of ordinary skill in the art will appreciate that these ranges represent illustrative embodiments.

In some embodiments, the inhibitor may comprise a siRNA molecule that reduces or inhibits the expression of LOX1. The siRNA molecule can, in some embodiments, be a single stranded or double stranded siRNA molecule that comprises a sequence capable of hybridizing to LOX1 mRNA, and induce RNA interference or another antisense mechanism that reduces or inhibits expression of protein. siRNA molecules may be of any sequence that allows the siRNA molecule to induce RNA interference resulting in reduction or inhibition of the expression of LOX1 protein. The siRNA molecule may, in some embodiments have a length of between 10 and 100, between 12 and 80, between 14 and 60, between 16 and 50, between 17 and 40. Suitably the siRNA has a length ranging from 18 to 30 nucleotides and, in certain embodiments between about 18 and about 26 nucleotides.

In embodiments comprising an inhibitory nucleic acid molecule, such inhibitors can bind to a target LOX1 nucleic acid sequence under stringent binding conditions. The terms "stringent conditions," "stringent binding conditions," or "stringent hybridization conditions" refers to conditions under which a polynucleotide will hybridize to a target sequence, to a detectably greater degree than other sequences (e.g., at least 2-fold over background). One non-limiting example of stringent conditions include those in which hybridization in 50% formamide, 1 M NaCl, 1% SDS at 37° C., and a wash in 0.1×SSC at 60° C. to 65° C. is performed.

Given the polynucleotide sequence of LOX1, an inhibitory nucleic acid molecule can be designed using motifs and targeted to a region that may be predicted to be effective for inhibitory activity, using standard techniques in the art.

Alternatively or additionally, any further methods which are suited to determine the activity of LOX1 and which are available to one of skill in the art may be used. As discussed above, the inhibitors useful in the various aspects and embodiments described herein may inhibit the activity of LOX1 by at least 10%, at least 20%, at least 30%, at least 40%, at least 50%, at least 60%, at least 70%, more preferably at least 80%, at least 90%, at least 91%, at least 92%, at least 93%, at least 94%, at least 95%, at least 96%, at least 97%, at least 98% or at least 99% when compared to a control. In particular embodiments, the inhibitors are effective to inhibit the activity of LOX1 by at least 50%, at least 60% or at least 70%. In other embodiments the inhibitors may inhibit the activity of LOX1, by at least 85% to about 100%, at least 90% to about 100%, at least 95% to about 100%, or by about 100%.

In embodiments, the inhibitors may be combined in a composition that comprises one or more further active agents suitable for the treatment or prevention of a tumor disease and/or a cancer. Some non-limiting examples of such active compounds including chemotherapeutic agents generally known in the art such as, for example, gemcitabine (Gemzar®), capecitabine (Xeloda®), Doxil®, cytarabine, dexamethasone, irinotecan (Camptosar®), oxaliplatin (Eloxatin®), albumin-bound paclitaxel (Abraxane®), temozolomide, adriamycin, doxorubicin, epirubicin, 5-fluorouracil, cytosine arabinoside ("Ara-C"), cyclophosphamide, thiotepa, busulfan, cytoxin, taxoids, (e.g., paclitaxel), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, melphalan and other related nitrogen mustards and hormonal agents that act to regulate or inhibit hormone action on tumors such as tamoxifen and onapristone.

C. Pharmaceutical Compositions and Formulations

In some aspects, the disclosure provides pharmaceutical compositions. Such pharmaceutical compositions may be compositions comprising an inhibitor of LOX1, or any combination of more than one LOX1 inhibitor. Such pharmaceutical compositions may also be compositions comprising a pharmaceutically acceptable excipient. In certain aspects, the pharmaceutical compositions of the disclosure are used as a medicament.

In certain aspects, the inhibitors disclosed herein may be formulated with a pharmaceutically acceptable carrier, excipient or stabilizer, as pharmaceutical compositions. In certain aspects, such pharmaceutical compositions are suitable for administration to a human or non-human animal via any one or more route of administration using methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Pharmaceutically acceptable carriers can be selected that are suitable for the mode of administration, solubility and/or stability desired or required.

When used for in vivo administration, the formulations of the disclosure should be sterile. The formulations of the disclosure may be sterilized by various sterilization methods, including sterile filtration, radiation, etc. In one aspect, the formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005).

In embodiments of this aspect, therapeutic compositions can be formulated for particular routes of administration, such as oral, nasal, pulmonary, topical (including buccal and sublingual), rectal, vaginal and/or parenteral administration. The phrases "parenteral administration" and "administered parenterally" as used herein refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Formulations of the present disclosure which are suitable for topical or transdermal administration include powders, sprays, ointments, pastes, creams, lotions, gels, solutions, patches and inhalants. The inhibitors and other actives may be mixed under sterile conditions with a pharmaceutically acceptable carrier, and with any preservatives, buffers, or propellants which may be required (U.S. Pat. Nos. 7,378,110; 7,258,873; 7,135,180; US Publication No. 2004-0042972; and 2004-0042971).

The formulations may conveniently be presented in unit dosage form and may be prepared by any method known in the art of pharmacy. Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient (e.g., "a therapeutically effective amount"). The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The disclosure similarly contemplates that formulations suitable for diagnostic and research use may also be made. The concentration of active agent in such formulations as well as the presence or absence of excipients can be selected based on the particular application and intended use.

D. Kits

Another aspect of the disclosure relates to a kit. In one aspect, a kit comprises any of the inhibitors, reagents, compositions, or pharmaceutical compositions as described above, and instructions or a label directing appropriate use or administration. Optionally, a kit may also include one or more containers and/or a syringe or other device to facilitate delivery or use. The disclosure contemplates that all or any subset of the components for conducting research assays, diagnostic assays and/or for administering therapeutically effective amounts may be enclosed in the kit. Similarly, the kit may include instructions for making a conjugate by, for example forming a covalent bond between an inhibitor of the disclosure and a therapeutic or diagnostic moiety under suitable conditions to form a conjugate. By way of additional example, a kit for use in a therapeutic method of the disclosure may comprise a solution containing a pharmaceutical formulation of the inhibitor(s) of LOX1, or a lyophilized preparation of one or more inhibitors, and instructions for administering the composition to a patient in need thereof and/or for reconstituting the lyophilized product.

The present disclosure also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In certain aspects, the formulation is suitable for intravenous administration, such as for intravenous infusion to a human or animal.

In a specific aspect, the formulations of the disclosure are formulated in single dose vials as a sterile liquid. Exemplary containers include, but are not limited to, vials, bottles, pre-filled syringes, IV bags, blister packs (comprising one or more pills). Optionally associated with such container(s) can be a notice in the form prescribed by a governmental agency regulating the manufacture, use or sale of pharmaceuticals or biological products, which notice reflects approval by the agency of manufacture, use or sale for human diagnosis and/or administration.

As with any pharmaceutical product, the packaging material and container are designed to protect the stability of the product during storage and shipment. Further, the products of the disclosure include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, etc., and other monitoring information.

A kit for diagnostic assays may comprise a solution containing an inhibitor of LOX1 as disclosed herein, or alternatively or in addition, reagents for detecting the presence of LOX1. The various reagents may be labeled according to methods known in the art and described herein, including but not limited to labels such as small molecule fluorescent tags, proteins such as biotin, GFP or other fluorescent proteins, or epitope sequences such as his or myc. Similarly, primary antibodies used for detecting LOX1 may be included in the kit. Primary antibodies may be directed to sequences on LOX1 or to labels, tags, or epitopes with which the LOX1 may be labeled. Primary antibodies may, in turn, be labeled for detection, or, if further amplification of the signal is desired, the primary antibodies may be detected by secondary antibodies, which may also be included in the kit.

Kits for research use are also contemplated. Such kits may, for example, resemble kits intended for diagnostic or therapeutic uses but further include a label specifying that the kit and its use is restricted to research purposes only.

Labels, Conjugates and Moieties

The disclosure relates to methods, compositions, and kits that comprise reagents that may be conjugated to labels for the purposes of diagnostics and other assays wherein one or more target molecules may be bound and detected by such labeled reagent(s). Labels include, without limitation, a chromophore, a fluorophore, a fluorescent protein, a phosphorescent dye, a tandem dye, a particle, a hapten, an enzyme and a radioisotope.

In certain aspects, the reagents are conjugated to a fluorophore. The choice of the fluorophore attached to the reagent(s) will determine the absorption and fluorescence emission properties of the conjugated molecule. Physical properties of a fluorophore label that can be used include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. Other suitable properties of the fluorescent label may include cell permeability and low toxicity, for example if labeling of the target(s) is to be performed in a cell or an organism (e.g., a living animal).

In certain aspects, an enzyme is a label and is conjugated to a reagent. Enzymes may be suitable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the preferred measurable product, e.g. colorimetric, fluorescent or chemiluminescence. Such substrates are extensively used in the art and are well known by one skilled in the art and include for example, oxidoreductases such as horseradish peroxidase and a substrate such as 3,3'-diaminobenzidine (DAB); phosphatase enzymes such as an acid phosphatase, alkaline and a substrate such as 5-bromo-6-chloro-3-indolyl phosphate (BCIP); glycosidases, such as beta-galactosidase, beta-glucuronidase or beta-glucosidase and a substrate such as 5-bromo-4-chloro-3-indolyl beta-D-galactopyranoside (X-gal); additional enzymes include hydrolases such as cholinesterases and peptidases, oxidases such as glucose oxidase and cytochrome oxidases, and reductases for which suitable substrates are known.

Enzymes and their appropriate substrates that produce chemiluminescence are suitable for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In another aspect, haptens such as biotin, are also utilized as labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

In certain aspects, fluorescent proteins may be conjugated to the reagent(s) as a label. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra.

In certain aspects, the label is a radioactive isotope. Examples of suitable radioactive materials include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113}$mIn, $^{115}$mIn), technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{135}$Xe), fluorine (18F), $^{153}$SM, $^{177}$Lu, $^{159}$Gd, $^{149}$Pm, $^{140}$La $^{175}$Yb, $^{166}$Ho, $^{90}$Y, $^{47}$Sc, $^{186}$Re, $^{188}$Re, $^{142}$Pr, $^{105}$Rh and $^{97}$Ru.

In some aspects, drugs or toxins may be conjugated to the reagent(s). For example, a reagent may be conjugated to a cytotoxic drug. In this example, the reagent may bind to LOX1, or a complex between LOX1 and a ligand or receptor, and the cytotoxic drug is then delivered to the cell. In some embodiments, the reagent-conjugate may be internalized in the cell, which releases the cytotoxic drug to the cell. Any cytotoxic drug known in the art may be conjugated. Some antibody conjugates are already approved by the FDA or are currently undergoing clinical trials.

The Examples that follow are presented in order to provide additional illustration of some of the aspects and embodiments disclosed above. The Examples should not be construed in any way as limiting the breadth of the scope of the disclosure or the appended claims.

EXAMPLES

Example 1: Generation of Cancer Stem Cell Enriched Cell Populations

Three patient-derived xenograft (PDX) pancreatic tumors were used as a source of cancer stem cells (CSCs) for screening. Late and metastatic tumors were used to better represent the patient population seen in the clinic. Excised tumors were minced into 2 mm³ pieces and dissociated in DMEM/F12 medium containing 200 units/mL Collagenase IV (Worthington Biologics), with mechanical disruption every 10-15 minutes until the tissue was completely dissociated. Cells were then washed 2× in Hanks' Balanced Salt Solution (HBSS) and passed through a 40 micron cell strainer. CSCs were enriched by plating dissociated tumor cells into ultra-low attachment 6-well plates in mesenchymal stem cell medium (MSCGM, Lonza). Cells were cultured for 4 days then harvested, dissociated using Accutase and frozen in Cryostar 5 medium. Cell suspensions were combined to obtain the 80 million cells needed for panning and screening.

Enrichment of pancreatic PDX-derived cancer stem cells. In order to enrich for CSCs, pancreatic PDX tumors from three different models purchased from Jackson Laboratories (FIG. 1A) were dissociated to single cells and plated in non-adherent, serum-free culture conditions. This resulted in the formation of tumorspheres (FIG. 1B) previously shown to enrich for CSCs. The enrichment of CSCs was determined by qPCR of genes EZH2, BMI1, SOX2, and Nanog, which are known to play important roles in stem cell biology, as well as CD24 and CD44 that are surface markers that can be used to define pancreatic CSCs. FIG. 1C shows a 40-300 fold increase in gene expression of all stemness genes when comparing the total tumor cells with spheres collected at day 4 post plating. The spheres were then dissociated into single cells to use for phenotypic selections using a designed ankyrin repeat protein "DARPin" library (Molecular Partners) (see, Example 2).

qPCR of CSC Spheres Versus Total Tumor Cells.

At the time of plating, 300,000 cells of each dissociated PDX model was flash frozen for use as the "total tumor" population. Following incubation for 4 days, spheres were harvested by centrifugation at 800 rpm. Spheres were then dissociated using Accutase and washed 2× in HBSS. Three-hundred thousand CSC sphere cells were then flash frozen for comparison to the total tumor. RNA was prepared from frozen pellets using the RNeasy Plus mini kit (Qiagen) following manufacturer's instructions. RNA was quantitated using a Nanodrop. RNA was reverse transcribed using Superscript II (Life Technologies) in a reaction containing 10 ng of RNA. The resulting cDNA was amplified using the Taqman PreAmp Master Mix kit following manufacturer's instructions. Following pre amplification the reaction was diluted 1:20 and 5 μL was used in a Taqman qPCR reaction (Life Technologies) and run on a Fast Dx Real-Time PCR machine.

Example 2: Identifying Binders Having Enhanced Binding to Cancer Stem Cells

Phage display cell panning was performed to identify DARPins that bind to enriched pancreatic CSC populations. A DARPin library, licensed from Molecular Partners, underwent affinity selection on sphere cells formed from the 3 PDX models (Lloyd C et al Modelling the human immune response: performance of a 1011 human antibody repertoire against a broad panel of therapeutically relevant antigens Protein Eng Des Sel 2009).

Identification of DARPins with Enriched Binding to Pancreatic CSCs.

Figure 2:
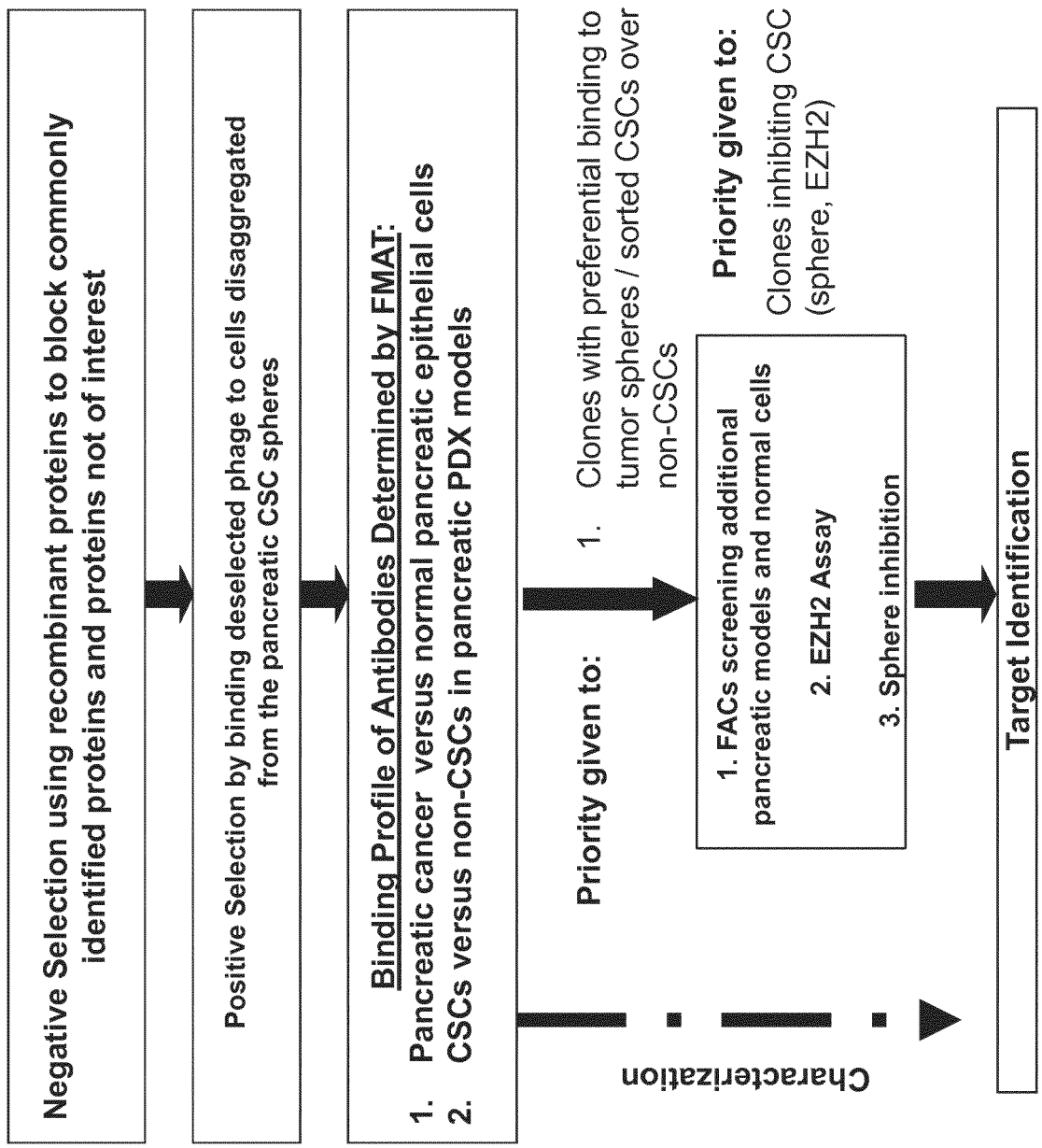
FIG. 2 shows the generalized screening cascade strategy used to identify DARPins capable of inhibiting CSCs. A negative selection was first used to remove proteins not of interest, and was followed by positive selection on the CSC tumorspheres generated from pancreatic PDX models. The specificity for DARPins binding to CSCs and not normal cells is confirmed, and those DARPins are tested in assays for their ability to inhibit CSCs, and the DARPin target(s) identified.

An overview of the general screening campaign is shown in FIG. 2. The DARpin library was first deselected against recombinant proteins for which we did not desire to isolate antibodies. Following deselection, the pancreatic PDX sphere-enriched CSCs were used for panning. Following selections, DARPins were eluted using trypsin followed by TEA. Eluted DARPins were assessed for binding to both CSCs sorted (CD24+CD44+EpCAM+ cells) from the pancreatic PDX model PA-0165 and normal pancreatic epithelial cells. STEM0268 bound to the CSCs enriched by flow cytometric sorting from the PA-0165 tumors but not to normal pancreatic epithelial cells (FIG. 3A) as determined by Fluorometric microvolume assay technology (FMAT).

Figure 3B:
Figure 4:
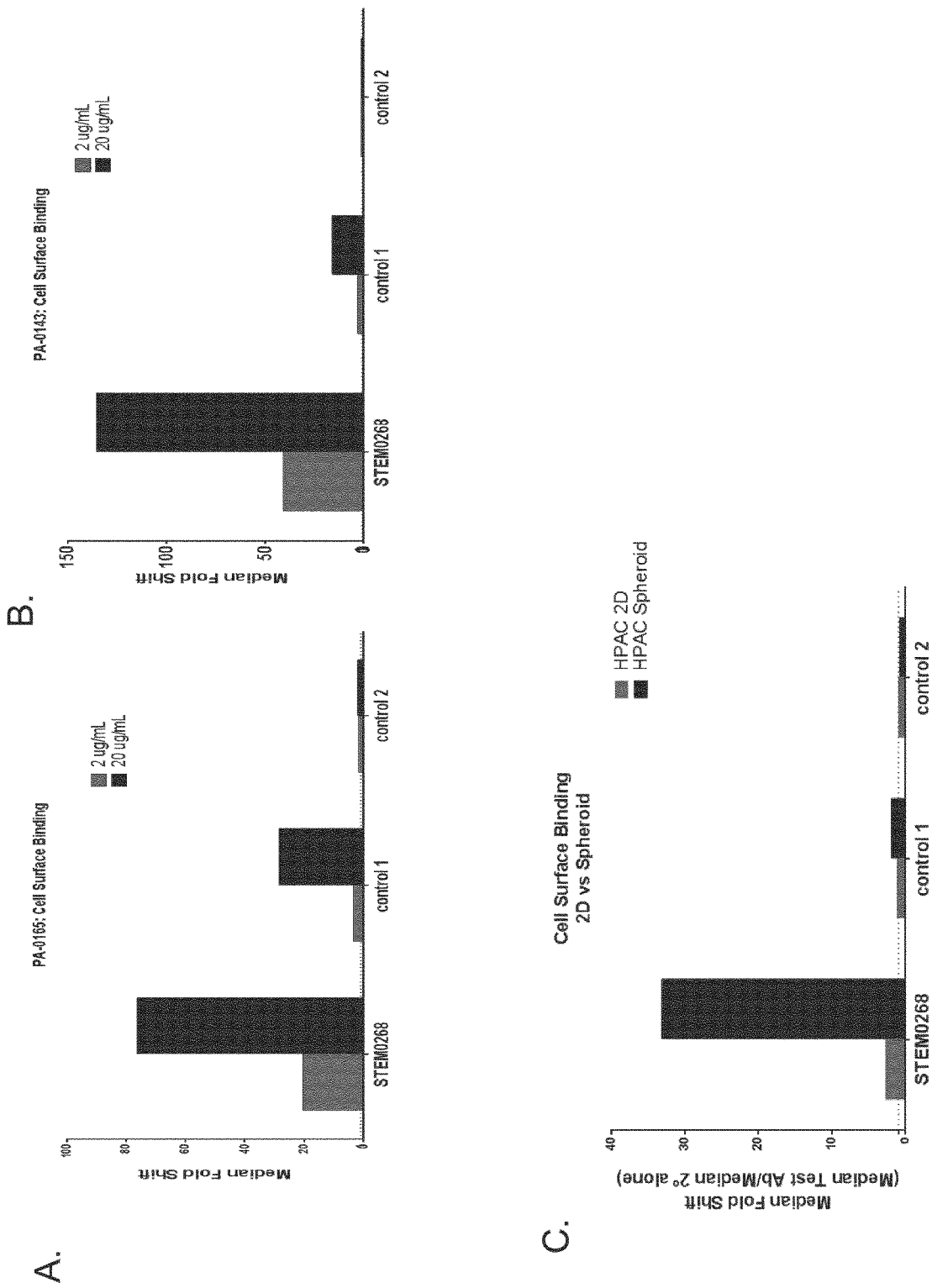
FIG. 4A-4C illustrates that STEM0268 binds to pancreatic cancer cells and is enriched on the CSCs. STEM0268 binds to the PDX models PA-0165 (A) and PA-0143 (B) as compared to two control DARPin-Fc. However, while STEM0268 exhibits some binding to the total tumor cells, it exhibits highly increased binding to the CSCs (C).

Inset in FIG. 3A shows bright field images of the cells. DARPins (10 ug/mL) were also screened for binding to other normal epithelial cell lines (bronchial, colon and renal) using fluorescent assisted cell sorting (FACS). STEM0268 showed minor binding to renal epithelial cells but no binding to bronchial and colon epithelial cells (FIG. 3B). The binding was further examined by FACS analysis, wherein STEM0268 showed binding to both the PA-0165 and PA-0143 PDX models (FIG. 4A and FIG. 4B, respectively) and showed significant increases in binding to spheres generated from HPAC cell line (FIG. 4C) as compared to cells grown under standard tissue culture conditions.

Binding of DARPins to Pancreatic Tumor Cells, Normal Epithelial Cells and CSCs.

Pancreatic cancer cell lines were purchased from ATCC. Normal pancreatic epithelial cells were purchased from Cell Systems and maintained according to manufacturer's instructions. Renal epithelial cells, hepatocytes, and colonic epithelial cells were all purchased from ScienCell Research Laboratories and maintained according to manufacturer's instructions. Cardiac myocytes and human bronchial epithelial cells were both purchased from PromoCell and cultured following manufacturer's instructions. Cell lines were first detached with 0.05% trypsin, or pancreatic PDX tumor chunks were dissociated following the same protocol described above. Cells were washed in flow cytometry buffer consisting of 1×HBSS, 2% bovine serum albumin, and 0.5 mM EDTA. Resuspended cells were counted and transferred to wells of a 96-well U-bottom plate in densities no greater than 200,000 cells per well. Cells were then incubated with DARPin clones at a 2 ug/mL for 1 hour at 4° C. Cells were washed in flow cytometry buffer and resuspended cells were stained with APC-goat-anti-human Fc fragment specific secondary antibody for 30 minutes at 4° C. in the dark. Cells were washed and resuspended in flow cytometry buffer containing DAPI for viability staining. Samples were read on an LSRII flow cytometer and analyzed using FlowJo software.

Screening for DARPin Activity Against CSCs.

DARPins showing the preferred binding patterns were screened for their ability to inhibit sphere formation using one of the pancreatic PDX models (PA-0143) used for selections. Briefly, following dissociation of the tumor cells they were plated in 96-well ultra-low attachment plates containing MSCGM with 50 ug/mL DARPins. All DARPins were tested in triplicate. After 4 days plates were read and inhibitory molecules were identified as showing inhibitory activity at least 1 standard deviation (SD) from the mean of the untreated and control DARPin-treated wells. A second assay based on expression of EZH2 in CSCs was also run. We have previously shown in pancreatic cancer that CSCs can be identified based on their high expression of EZH2 and trimethylation of histone 3 on lysine 27 (Van Vlerken L et al. 2013 EZH2 is required for breast and pancreatic cancer stem cell maintenance and can be used as a functional cancer stem cell reporter *Stem Cells Transl Med* 2(1):43-52). Using HPAC cells, the EZH2 assay was performed as previously described with the inclusion of 50 µg/mL DARPin. DARPins inhibiting at least 1 SD from the mean of the untreated and control wells were considered as positive hits.

Example 3: Inhibitor of Cancer Stem Cells

STEM0268 inhibits cancer stem cells. To determine if STEM0268 is able to inhibit CSCs, we tested its ability to inhibit tumor sphere formation of pancreatic PDX models. Briefly, cells were dissociated using 200 units/mL of collagenase IV plated, washed counted and resuspended at 30,000 cells/mL in MSCGM (Lonza) and plated in an ultra-low attachment 6-well plate. Antibodies were added to appropriate wells at 50 µg/mL. Following incubation for 4 days, spheres were harvested, dissociated and replated in a similar manner to generate secondary spheres and assess the ability of CSCs to self-renew. STEM0268 showed a 27% inhibition in the PA-0143 when compared to untreated or a control DARPin-Fc (FIG. 5A) model and 25% inhibition in the PA-0165 model (FIG. 5B). The ability of STEM0268 to reduce the number of EZH2$^{high}$ cells, which we have previously demonstrated marks pancreatic CSCs (Van Vlerken L et al. 2013) in the HPAC cell line, was also measured. As shown in FIG. 5C, STEM0268 reduced the EZH2$^{high}$ cells by 43% as compared to the DARPin-Fc control (P<0.005). Salinomycin (1 µM) served as the positive control in both of these experiments (Gupta P B et al. 2009). These experiments collectively demonstrate that STEM0268 can inhibit CSCs of pancreatic PDX models.

Example 4: Identification of LOX1 as Target for Inhibiting Cancer Stem Cells

DARPin Target Identification.

In order to identify the target of STEM0268, we screened a library of protein-overexpressing HEK293 cells as previously described (Yao et al). Briefly, a plasmid library composed of 4319 mammalian expression vectors (each encoding a unique membrane protein) were transfected individually into HEK293T cells. STEM0268 protein was diluted in cultured media, mixed with an AlexaFluor647-conjugated anti-human IgG Fc secondary antibody, and added to the transfected cells. The cells were incubated with the protein overnight at 37° C. and then binding was measured by confocal microscopy. Positive microscopic hits were then screened by FACS. FIG. 6A shows the FACS binding of STEM0268 to the cells overexpressing LOX1. Fc gamma receptor 2b (Fcgr2b) was used as a positive control for binding to the DARPin-Fc. Examples of FACs binding of STEM0268 to other non-target proteins (S1PR2 and BMPR1A) is shown. To confirm this identification of the target for STEM0268, an ELISA was performed using flag-tagged recombinant human LOX1 (rhLOX1). STEM0268 did indeed bind to rhLOX1 (FIG. 6B). Neither of the control DARPin-Fcs bound, and an anti-FLAG antibody was also capable of detecting the flag-tagged rhLOX1. The ability of STEM0268 to bind to LOX1 was further confirmed by Octet analysis (FIG. 6C).

LX5140110 Inhibits Cancer Stem Cells.

To further confirm the ability of a LOX1 inhibitor to inhibit CSC sphere formation, a LOX1-specific monoclonal antibody (mAb), LX5140110, which comprises a VL comprising SEQ ID NO: 33 and a VH comprising SEQ ID NO: 4 (see, e.g., Table 1), was compared to STEM0268 for their ability to inhibit sphere formation in the pancreatic PDX models. LX5140110 inhibited sphere formation in both PA-0165 and PA-0143 models (FIG. 7A) to a similar extent as STEM0268. In addition, LX5140110 was able to inhibit CSCs from multiple pancreatic (FIG. 7B) and colorectal cell lines (FIG. 7C).

An in vivo study with PA-0143, was run to determine the ability of LX5140110 to inhibit CSCs in vivo. PA-0143 PDX tumors were passaged by trocar implantation of tumor fragments into 6-8 week old NSG mice (NOD.Cg-Prkdc$^{scid}$ Il2rg$^{tm1Wjl}$/SzJ) and allowed to grow to ~300 mm$^3$ at which point they were randomized and treated with subcutaneous injections of either a control IgG1 mAb or LX5140110 at 30 mg/kg twice-weekly for 2 weeks (FIG. 8A). LX51401110 only slightly reduced tumor growth of the PA-0143 model compared to both the vehicle treated and a control non-specific IgG1 also dosed at 30 mg/kg (P<0.001, Tukey's comparison test), as anticipated since LOX1 appears to be expressed primarily on the CSCs which represent only a small percentage of the tumor. Twenty-four hours after the last dose of antibodies, tumors were removed from a subset of the mice and analyzed for the percentage of CSCs. LX5140110 showed a significant reduction of CSCs as compared to the vehicle control (FIG. 8B).

Combinations of LX5140110 and Chemotherapy Result in Improved Anti-Tumor cell efficacy.

Given that chemotherapies and even some targeted therapies can enrich for CSCs despite the reductions in tumor burden, combination approaches using a CSC-specific targeted therapy in combination with these agents becomes an attractive approach to treatment of cancer patients. Since LX5140110 targets CSCs specifically, we sought to address the combined effects of the current standard of care chemotherapy for pancreatic cancer, gemcitabine, and LX5140110. First the ability of gemcitabine to inhibit the Pan02.13 was tested. Pan02.13 cells were plated under standard tissue culture conditions with and without 100 ng/mL gemcitabine in a tissue culture coated flat-bottomed plate (n=10). At 100 ng/mL there was a significant reduction in cell numbers (FIG. 9A, P<0.001 student's two-tailed T-test). To determine the effects of treatments on CSCs, Pan02.13 was treated in standard tissue culture conditions for 4 days with either 50 µg/mL of LX5140110 or a control antibody and with or without 100 ng/mL of gemcitabine (GEM) then analyzed for the percentage of CSCs by flow cytometry. The percentage of CSCs (EpCAM+CD24+CD44+) was determined for each treatment condition. The cells were first gated for single, viable cells using scatter and DAPI. Fluorescence minus one (FMO) controls were utilized for gating, with the EpCAM+ population analyzed for CD44 and CD24 expression. The frequency of CSCs of viable cells is reported in FIG. 9B. Under these conditions and time point, LX5140110 showed a slight reduction of CSCs. As has been reported, gemcitabine enriched for CSCs and this enrichment was not affected by inclusion of a non-specific IgG1. However, treatment with LX5140110 not only inhibited this increase but also slightly decreased the percentage of CSCs from the baseline levels (0.62% versus 0.81% for the control IgG1 without gemcitabine).

Inhibition of LOX1 can Reduce Chemotherapy-Induced Cardiomyocyte Damage.

While the combination of chemotherapy and anti-CSC targeted therapies will likely be useful in the clinic, it is known that many chemotherapies have unintended harmful side effects in addition to anti-tumor activity. One such side effect is cardiac damage that can lead to cardiomyocyte death and heart failure. LOX1 has been shown to play a major role in doxorubicin-mediated cardiomyocyte damage (See, Spallarossa et al., Biochemical and Biophysical Research Communications (2005) 335 188-196. Yokoyama et al., (2016) PLoS ONE 11(5): e0154994. doi:10.1371/journal.pone.0154994). First, we examined the expression of LOX1 in response to doxorobucin treatment in human aortic endothelial cells (HAEC) and embryonic stem cell derived cardiomyocytes. Oxidized LDL (Ox-LDL) is a conventional ligand of LOX1 and was added as a control, since previous reports show an increase of LOX1 in response to Ox-LDL in rat cardiac muscle cells (Spallarossa et al., (2005)). Forty-thousand cells were plated in a 96-well plate and treated with media alone or media containing 5 µM doxorubicin for 24 hours. The cells were then scraped and lysed with 1×RIPA buffer containing protease inhibitors on ice for 1 h. Loading buffer was added to each sample followed by heating for 10 min at 90° C. Twelve microliters of sample was loaded per lane in a 4-12% bis-tris gradient gel. The gels were run for 40 min at 200V in MOPS buffer. The proteins were transferred onto a nitrocellulose membrane using iBlot. The membrane was blocked overnight with casein solution. LX5140110 was added at 1 µg/ml in casein blocking buffer to the membrane and incubated at room temperature for 1 h. Membrane was washed 3 times for 5 min each with TBST buffer. Anti-human-Fc antibody conjugated to HRP was added at 1:5000 dilution in casein blocking buffer and incubated at room temperature for 1 h. Membrane was washed twice with TBST for 10 min each followed by a final wash with TBS buffer for 15 min. Supersignal ELISA Pico chemiluminescent substrate was added for 1 min. The membrane was exposed to the film and developed. As shown in FIG. 10A, LOX1 protein was upregulated in both Ox-LDL and DOX-treated human aortic endothelial cells, which are the first encounters of chemotherapeutic agents in the heart. Interestingly, we also detected an increase of LOX1 expression in cardiomyocytes treated with 5 µM DOX (FIG. 10B).

Next, we sought to determine if inhibiting LOX1 could block doxorubicin-mediated cardiomyocyte damage. Cytivia™ cardiomyocytes were purchased from GE Healthcare and plated following manufacturer's instructions with the substitution of bovine fibronectin for human fibronectin. Cells were allowed to adhere for 4 days and then medium was changed. At days 5-7, medium was removed and cells were pre-incubated with the indicated concentration of LX5140110 for 4 hours prior to the addition of 5 µM doxorubicin (DOX). After addition of DOX, cells were incubated for a further 24 hours. After incubation, media was removed and cells were stained with DAPI (1:4000 dilution of 1 mg/mL), TOTO-3 (1 uL of dye solution per 1 mL of medium), and 5 µM Fluo-4. Cells were incubated for 1 hour at 37° C. and then imaged on Image on GE IN Cell Analyzer. Viability was determined by obtaining the number of cells excluding DAPI and TOTO-3 dyes while Fluo-4 was used to determine calcium concentrations. It is known that cardiomyocytes show an increase in calcium load during endotoxin induced cardiac dysfunction. (Thompson et al., Pediatric Research (2000) 47: 669-676). As shown in FIG. 11A, the calcium concentration was increased approximately 2.5-fold in cardiomyocytes incubated with 5 µM DOX as compared to untreated controls showing cardiomyocyte dysfunction. (Importantly, LX5140110 was able to inhibit the accumulation of calcium as a result of DOX treatment. Moreover, DOX resulted in decreased viability of cardiomyocytes (FIG. 11B) that was again reversed by the LOX1 inhibitor LX5140110.

Discussion

The data in the above Examples demonstrates a previously unidentified and unexpected function for LOX1 aside from its known role in coronary and circulatory health. In particular, the studies presented herein demonstrate that with regard to cancer, LOX1 has a specific role in CSC function, representing a previously unreported finding. In several of the illustrative Examples, the results show that in models of pancreatic and colorectal cancer, LOX1 is overexpressed by CSCs and has a functional role in CSC activity, as exogenous administration of LOX1 inhibitors (DARPin and mAb) to PDX models provided a direct inhibition of CSCs. Moreover, the data in the above Examples show that LOX1 inhibitors can inhibit the increase of CSCs induced by chemotherapy and make the use of these in combination an attractive clinical paradigm. In addition, we provide evidence in the above Examples that LOX1 inhibitors may also protect against cardiac damage induced by chemotherapy, a significant problem for patients treated with these drugs.

An abundance of pre-clinical and clinical evidence points to a critical function for CSCs in cancer treatment, thus treatments targeting this population of tumor cells can be of high value. The work described here points not only to a novel and important role for the LOX1 in CSC maintenance, but suggests that neutralization of LOX1 can be a useful strategy to inhibit CSC function and that inhibition of CSCs by blocking LOX1 could allow for unique and effective therapies to improve patient lives.

INCORPORATION BY REFERENCE

All publications and patents mentioned herein are hereby incorporated by reference in their entirety as if each individual publication or patent was specifically and individually indicated to be incorporated by reference.

While specific aspects of the disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

SELECTED REFERENCES

Al-Hajj et al., (2003). Prospective identification of tumorigenic breast cancer cells. Proceedings of the National Academy of Sciences of the United States of America 100, 3983-3988.
Barker et al., (2009). Crypt stem cells as the cells-of-origin of intestinal cancer. Nature 457, 608-611.
Creighton et al., (2009). Residual breast cancers after conventional therapy display mesenchymal as well as tumor-initiating features. Proceedings of the National Academy of Sciences 106, 13820-13825.
Gemei et al., (2013). CD66c is a novel marker for colorectal cancer stem cell isolation, and its silencing halts tumor growth in vivo. Cancer 119, 729-738.
Gupta P B et al., 2009 Identification of selective inhibitors of cancer stem cells by high-throughput screening Cell 138(4):645-59.
Fangning Wan et al., Oxidized low-density lipoprotein is associated with advanced-stage prostate cancer. 2015 Tumor Biology 36 (5):3573-82.
Hermann et al., (2007). Distinct populations of cancer stem cells determine tumor growth and metastatic activity in human pancreatic cancer. Cell stem cell 1, 313-323.
Hinagata et al., Cardiovasc. Res. 69:263-71 (2006).
Hirsh et al., A common gene network link cancer with lipid metabolism and diverse human diseases. 2010 Cancer Cell 17:348-61).
Hirsch et al., (2014). LGR5 positivity defines stem-like cells in colorectal cancer. Carcinogenesis 35, 849-858.
Inoue et al., Circ. Res. 97:176-84 (2005).
Khaidakov et al. Oxidized LDL receptor 1 (OLR1) as a possible link between obesity, dyslipidemia and cancer. 2011 PLOSOne 6(5):e20277.
Kume et al., 70th Scientific Sessions of the American Heart Association Ser. 96, 1997.
Lapidot et al., (1994). A cell initiating human acute myeloid leukaemia after transplantation into SCID mice. Nature 367, 645-648.
Li et al., (2007). Identification of pancreatic cancer stem cells. Cancer research 67, 1030-1037.
Li et al., Cir. Cardio. Imaging 3:464-72 (2010).
Long et al. Combination of body mass index and oxidized low density lipoprotein receptor 1 in prognosis prediction of patients with squamous non-small cell lung cancer. 2015 Oncotarget advance publications, see, online publications at www.impactjournals.com/oncotarget/.
Mehta et al., Circ. Res. 100:1634-1642 (2007).
Nakamura et al., J. Pharm. Biomed. Anal. 51:158-163 (2010).
Ohki et al., Structure 13:905-917 (2005).
Tehranchi et al. (2010). Persistent Malignant Stem Cells in del(5q) Myelodysplasia in Remission. New England Journal of Medicine 363, 1025-1037.
Ulrich-Merzenich et al., Expert Opin Ther Targets. 17(8): 905-19 (2013).
Van Vlerken L et al. 2013 EZH2 is required for breast and pancreatic cancer stem cell maintenance and can be used as a functional cancer stem cell reporter Stem Cells Transl Med 2(1):43-52.
Wang et al., (2012). Evaluation of CD44 and CD133 as cancer stem cell markers for colorectal cancer. Oncology reports 28, 1301-1308.
White et al., Cardiovascular pathology 20:369-73 (2011).
Xu et al., Arterioscler. Thromb. Vasc. Biol. 27(4) 871-877 (2007).
Zhao et al., Clin. Cardiol. 34:172-177 (2011).

We claim:

1. A method for inhibiting proliferation of a cancer stem cell (CSC) comprising contacting the CSC with a Lectin-like oxidized LDL receptor 1 (LOX1) antibody comprising a set of complementary determining regions (CDRs): heavy chain variable region (VH)-CDR1, VH-CDR2, VH-CDR3, and light chain variable region (VL)-CDR1, VL-CDR2 and VL-CDR3, wherein:
   (a) VH-CDR1 has the amino acid sequence of SEQ ID NO:1;
   (b) VH-CDR2 has the amino acid sequence of SEQ ID NO:2;
   (c) VH-CDR3 has the amino acid sequence of SEQ ID NO:3;
   (d) VL-CDR1 has the amino acid sequence of SEQ ID NO:30;
   (e) VL-CDR2 has the amino acid sequence of SEQ ID NO:31; and
   (f) VL-CDR3 has the amino acid sequence of SEQ ID NO:32;
   in an amount effective to inhibit proliferation of the CSC.

2. The method of claim 1 wherein the CSC expresses LOX1.

3. The method of claim 1 wherein the CSC is a sphere-forming CSC.

4. The method of claim 1 wherein the CSC is from a cancer selected from the group consisting of colorectal cancer, pancreatic cancer, lung cancer, head and neck cancer, gastric cancer, hepatocellular carcinoma, and breast cancer.

5. The method of claim 1, wherein the LOX1 antibody further comprises a heavy chain immunoglobulin constant domain selected from the group consisting of:
   (a) a human IgA constant domain
   (b) a human IgD constant domain;
   (c) a human IgE constant domain;
   (d) a human IgG1 constant domain;
   (e) a human IgG2 constant domain;
   (f) a human IgG3 constant domain;
   (g) a human IgG4 constant domain; and
   (h) a human IgM constant domain.

6. The method of claim 5, wherein the LOX1 antibody comprises a human IgG1 heavy chain constant domain.

7. The method of claim 6, wherein the IgG1 heavy chain constant domain contains the mutations L234F, L235E and P331S, wherein the position numbering is according to the EU index as in Kabat.

8. The method of claim 1, wherein the LOX1 antibody further comprises a light chain immunoglobulin constant domain selected from the group consisting of:
   (a) a human Ig kappa constant domain; and
   (b) a human Ig lambda constant domain.

9. The method of claim 1, wherein the LOX1 antibody comprises a heavy chain variable region (VH) having the amino acid sequence of SEQ ID NO:4 and a light chain variable region (VL) having the amino acid sequence of SEQ ID NO:33.

10. The method of claim 9, wherein the LOX1 antibody further comprises a heavy chain immunoglobulin constant domain selected from the group consisting of:
    (a) a human IgA constant domain
    (b) a human IgD constant domain;
    (c) a human IgE constant domain;
    (d) a human IgG1 constant domain;
    (e) a human IgG2 constant domain;
    (f) a human IgG3 constant domain;
    (g) a human IgG4 constant domain; and
    (h) a human IgM constant domain.

11. The method of claim 10, wherein the LOX1 antibody comprises a human IgG1 heavy chain constant domain.

12. The method of claim 11, wherein the IgG1 heavy chain constant domain contains the mutations L234F, L235E and P331S, wherein the position numbering is according to the EU index as in Kabat.

13. The method of claim 9, wherein the LOX1 antibody further comprises a light chain immunoglobulin constant domain selected from the group consisting of:
    (a) a human Ig kappa constant domain; and
    (b) a human Ig lambda constant domain.

* * * * *

```
SEQUENCE LISTING

<160> NUMBER OF SEQ ID NOS: 78

<210> SEQ ID NO 1
<211> LENGTH: 5
<212> TYPE: PRT
<213> ORGANISM: Artificial Sequence
<220> FEATURE:
<223> OTHER INFORMATION: Lox514 CDR-1 Heavy Chain sequence

<400> SEQUENCE: 1

Glu Leu Ser Met His
1               5

<210> SEQ ID NO 2
<211> LENGTH: 17
<212> TYPE: PRT
<213> ORGANISM: Artificial Sequence
```

```
<220> FEATURE:
<223> OTHER INFORMATION: LX5140110 CDR-2 Heavy Chain sequence

<400> SEQUENCE: 2

Gly Phe Asp Pro Glu Asp Phe Lys Tyr His Thr His Gln Lys Phe Gln
1               5                   10                  15

Gly

<210> SEQ ID NO 3
<211> LENGTH: 20
<212> TYPE: PRT
<213> ORGANISM: Artificial Sequence
<220> FEATURE:
<223> OTHER INFORMATION: LX5140110 CDR-3 Heavy Chain sequence

<400> SEQUENCE: 3

Val Trp Gly Thr Gln Gly Lys Gly Val Arg Gly Trp Asp Tyr Tyr Tyr
1               5                   10                  15

Gly Met Asp Val
            20

<210> SEQ ID NO 4
<211> LENGTH: 129
<212> TYPE: PRT
<213> ORGANISM: Artificial Sequence
<220> FEATURE:
<223> OTHER INFORMATION: LX5140110 Heavy Chain sequence

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Phe Lys Tyr His Thr His Gln Lys Phe
    50                  55                  60

Gln Gly Arg Val Thr Met Thr Glu Asp Thr Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Leu Val Trp Gly Thr Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 5
<211> LENGTH: 17
<212> TYPE: PRT
<213> ORGANISM: Artificial Sequence
<220> FEATURE:
<223> OTHER INFORMATION: Lox514 CDR-2 Heavy Chain sequence

<400> SEQUENCE: 5

Gly Phe Asp Pro Glu Asp Gly Glu Thr Ile Tyr Ala Gln Lys Phe Gln
1               5                   10                  15

Gly
```

-continued

```
<210> SEQ ID NO 6
<211> LENGTH: 17
<212> TYPE: PRT
<213> ORGANISM: Artificial Sequence
<220> FEATURE:
<223> OTHER INFORMATION: LX5140011 CDR-2 Heavy Chain sequence

<400> SEQUENCE: 6

Gly Phe Asp Pro Glu Asp Trp Glu Tyr Ala Tyr Asp Gln Lys Phe Gln
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: LX5140014 CDR-2 Heavy Chain sequence

<400> SEQUENCE: 7

Gly Phe Asp Pro Glu Asp Tyr Thr Ile Arg Val Gly Gln Lys Phe Gln
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: LX5140016 CDR-2 Heavy Chain sequence

<400> SEQUENCE: 8

Gly Phe Asp Pro Glu Asp Trp Gln Thr His Thr Ala Gln Lys Phe Gln
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: LX5140038 CDR-2 Heavy Chain sequence

<400> SEQUENCE: 9

Gly Phe Asp Pro Glu Asp Trp Thr Ile His Val Asp Gln Lys Phe Gln
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: LX5140094 CDR-2 Heavy Chain sequence

<400> SEQUENCE: 10

Gly Phe Asp Pro Glu Asp Trp Gln Tyr His Val Ser Gln Lys Phe Gln
1               5                   10                  15

Gly

<210> SEQ ID NO 11
<211> LENGTH: 17
<212> TYPE: PRT
<213> ORGANISM: Artificial Sequence
```

```
<220> FEATURE:
<223> OTHER INFORMATION: LX5140108 CDR-2 Heavy Chain sequence

<400> SEQUENCE: 11

Gly Phe Asp Pro Glu Asp Trp Ser Asn His Val Ser Gln Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: LX5140092 CDR-2 Heavy Chain sequence

<400> SEQUENCE: 12

Gly Phe Asp Pro Glu Asp Trp Lys Tyr His Leu Ser Gln Lys Phe Gln
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: LX5140093 CDR-2 Heavy Chain sequence

<400> SEQUENCE: 13

Gly Phe Asp Pro Glu Asp Trp Ala Tyr His Gln Ala Gln Lys Phe Gln
1               5                   10                  15

Gly

<210> SEQ ID NO 14
<211> LENGTH: 20
<212> TYPE: PRT
<213> ORGANISM: Artificial Sequence
<220> FEATURE:
<223> OTHER INFORMATION: LX5140011 CDR-3 Heavy Chain sequence

<400> SEQUENCE: 14

Pro Asn Gly Gln Gln Gly Lys Gly Val Arg Gly Trp Asp Tyr Tyr Tyr
1               5                   10                  15

Gly Met Asp Val
            20

<210> SEQ ID NO 15
<211> LENGTH: 20
<212> TYPE: PRT
<213> ORGANISM: Artificial Sequence
<220> FEATURE:
<223> OTHER INFORMATION: LX5140108 CDR-3 Heavy Chain sequence

<400> SEQUENCE: 15

Ser Thr Gly Arg Gln Gly Lys Gly Val Arg Gly Trp Asp Tyr Tyr Tyr
1               5                   10                  15

Gly Met Asp Val
            20

<210> SEQ ID NO 16
<211> LENGTH: 20
<212> TYPE: PRT
<213> ORGANISM: Artificial Sequence
<220> FEATURE:
<223> OTHER INFORMATION: LX5140092_D CDR-3 Heavy Chain sequence
```

```
<400> SEQUENCE: 16

Pro Asp Gly Thr His Gln Gly Gly Val Arg Gly Trp Asp Tyr Tyr Tyr
1               5                   10                  15

Gly Met Asp Val
            20

<210> SEQ ID NO 17
<211> LENGTH: 20
<212> TYPE: PRT
<213> ORGANISM: Artificial Sequence
<220> FEATURE:
<223> OTHER INFORMATION: LX5140092_N CDR-3 Heavy Chain sequence

<400> SEQUENCE: 17

Pro Asn Gly Thr His Gln Gly Gly Val Arg Gly Trp Asp Tyr Tyr Tyr
1               5                   10                  15

Gly Met Asp Val
            20

<210> SEQ ID NO 18
<211> LENGTH: 20
<212> TYPE: PRT
<213> ORGANISM: Artificial Sequence
<220> FEATURE:
<223> OTHER INFORMATION: LX5140093_D CDR-3 Heavy Chain sequence

<400> SEQUENCE: 18

Pro Asp Gly Gln Gln Gly Lys Gly Val Arg Gly Trp Asp Tyr Tyr Tyr
1               5                   10                  15

Gly Met Asp Val
            20

<210> SEQ ID NO 19
<211> LENGTH: 129
<212> TYPE: PRT
<213> ORGANISM: Artificial Sequence
<220> FEATURE:
<223> OTHER INFORMATION: LX5140011 Heavy Chain sequence

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Trp Glu Tyr Ala Tyr Asp Gln Lys Phe
        50                  55                  60

Gln Gly Arg Val Thr Met Thr Glu Asp Thr Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
                100                 105                 110

Tyr Tyr Gly Met Asp Val Trp Gly Gln Gly Thr Thr Val Thr Val Ser
            115                 120                 125

Ser
```

<210> SEQ ID NO 20
<211> LENGTH: 129
<212> TYPE: PRT
<213> ORGANISM: Artificial Sequence
<220> FEATURE:
<223> OTHER INFORMATION: LX5140014 Heavy Chain sequence

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Tyr Thr Ile Arg Val Gly Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser
```

<210> SEQ ID NO 21
<211> LENGTH: 129
<212> TYPE: PRT
<213> ORGANISM: Artificial Sequence
<220> FEATURE:
<223> OTHER INFORMATION: LX5140016 Heavy Chain sequence

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Trp Gln Thr His Thr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser
```

<210> SEQ ID NO 22
<211> LENGTH: 129
<212> TYPE: PRT
<213> ORGANISM: Artificial Sequence
<220> FEATURE:
<223> OTHER INFORMATION: LX5140038 Heavy Chain sequence

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Trp Thr Ile His Val Asp Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 23
<211> LENGTH: 129
<212> TYPE: PRT
<213> ORGANISM: Artificial Sequence
<220> FEATURE:
<223> OTHER INFORMATION: LX5140094 Heavy Chain sequence

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Trp Gln Tyr His Val Ser Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 24
<211> LENGTH: 129
<212> TYPE: PRT
<213> ORGANISM: Artificial Sequence
<220> FEATURE:
<223> OTHER INFORMATION: LX5140108 Heavy Chain sequence

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
         35                  40                  45

Gly Gly Phe Asp Pro Glu Asp Trp Ser Asn His Val Ser Gln Lys Phe
 50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
             85                  90                  95

Leu Thr Ser Thr Gly Arg Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 25
<211> LENGTH: 129
<212> TYPE: PRT
<213> ORGANISM: Artificial Sequence
<220> FEATURE:
<223> OTHER INFORMATION: LX5140092_D Heavy Chain sequence

<400> SEQUENCE: 25

Gln Val Gln Leu Val Gln Ser Gly Ala Glu Val Lys Lys Pro Gly Ala
1                5                  10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
         35                  40                  45

Gly Gly Phe Asp Pro Glu Asp Trp Lys Tyr His Leu Ser Gln Lys Phe
 50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
             85                  90                  95

Ala Thr Pro Asp Gly Thr His Gln Gly Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 26
<211> LENGTH: 129
<212> TYPE: PRT
<213> ORGANISM: Artificial Sequence
<220> FEATURE:
<223> OTHER INFORMATION: LX5140092_N Heavy Chain sequence

<400> SEQUENCE: 26

Gln Val Gln Leu Val Gln Ser Gly Ala Glu Val Lys Lys Pro Gly Ala
1                5                  10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
         35                  40                  45

Gly Gly Phe Asp Pro Glu Asp Trp Lys Tyr His Leu Ser Gln Lys Phe
 50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Thr His Gln Gly Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 27
<211> LENGTH: 129
<212> TYPE: PRT
<213> ORGANISM: Artificial Sequence
<220> FEATURE:
<223> OTHER INFORMATION: LX5140093_D Heavy Chain sequence

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Trp Ala Tyr His Gln Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asp Gly Gln Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 28
<211> LENGTH: 129
<212> TYPE: PRT
<213> ORGANISM: Artificial Sequence
<220> FEATURE:
<223> OTHER INFORMATION: LX5140093_N Heavy Chain sequence

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Trp Ala Tyr His Gln Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

```
Ala Thr Pro Asn Gly Gln Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 29
<211> LENGTH: 129
<212> TYPE: PRT
<213> ORGANISM: Artificial Sequence
<220> FEATURE:
<223> OTHER INFORMATION: Lox514 Heavy Chain sequence

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
            100                 105                 110

Tyr Tyr Gly Met Asp Val Trp Gly Arg Gly Thr Thr Val Thr Val Ser
        115                 120                 125

Ser

<210> SEQ ID NO 30
<211> LENGTH: 14
<212> TYPE: PRT
<213> ORGANISM: Artificial Sequence
<220> FEATURE:
<223> OTHER INFORMATION: Lox514 CDR-1 Light Chain sequence

<400> SEQUENCE: 30

Thr Gly Ser Ser Ser Asn Ile Gly Ala Gly Tyr Asp Val His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Lox514 CDR-2 Light Chain sequence

<400> SEQUENCE: 31

Gly Asn Ser Asn Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Lox514 CDR-3 Light Chain sequence
```

-continued

```
<400> SEQUENCE: 32

Gln Ser Tyr Asp Ser Ser Leu Ser Gly Trp Val
1               5                   10

<210> SEQ ID NO 33
<211> LENGTH: 111
<212> TYPE: PRT
<213> ORGANISM: Artificial Sequence
<220> FEATURE:
<223> OTHER INFORMATION: LX5140110 Light Chain sequence

<400> SEQUENCE: 33

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu
            100                 105                 110

<210> SEQ ID NO 34
<211> LENGTH: 10
<212> TYPE: PRT
<213> ORGANISM: Artificial Sequence
<220> FEATURE:
<223> OTHER INFORMATION: LX5140094 CDR-3 Light Chain sequence

<400> SEQUENCE: 34

Gln Ser Tyr Asp Ser Met Tyr Arg Phe Gly
1               5                   10

<210> SEQ ID NO 35
<211> LENGTH: 11
<212> TYPE: PRT
<213> ORGANISM: Artificial Sequence
<220> FEATURE:
<223> OTHER INFORMATION: LX5140093 CDR-3 Light Chain sequence

<400> SEQUENCE: 35

Gln Ser Tyr Asp Ser Ser His Arg Ala Trp Ala
1               5                   10

<210> SEQ ID NO 36
<211> LENGTH: 110
<212> TYPE: PRT
<213> ORGANISM: Artificial Sequence
<220> FEATURE:
<223> OTHER INFORMATION: LX5140094 Light Chain sequence

<400> SEQUENCE: 36

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Met
                 85                  90                  95

Tyr Arg Phe Gly Phe Gly Gly Thr Lys Leu Thr Val Leu
            100                 105                 110

<210> SEQ ID NO 37
<211> LENGTH: 111
<212> TYPE: PRT
<213> ORGANISM: Artificial Sequence
<220> FEATURE:
<223> OTHER INFORMATION: LX5140093 Light Chain sequence

<400> SEQUENCE: 37

Gln Ser Val Val Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

His Arg Ala Trp Ala Phe Gly Gly Gly Thr Lys Leu Thr Val Leu
            100                 105                 110

<210> SEQ ID NO 38
<211> LENGTH: 5
<212> TYPE: PRT
<213> ORGANISM: Artificial Sequence
<220> FEATURE:
<223> OTHER INFORMATION: Lox696 CDR-1 Heavy Chain sequence

<400> SEQUENCE: 38

Asp Tyr Ala Met His
 1               5

<210> SEQ ID NO 39
<211> LENGTH: 17
<212> TYPE: PRT
<213> ORGANISM: Artificial Sequence
<220> FEATURE:
<223> OTHER INFORMATION: Lox696 CDR-2 Heavy Chain sequence

<400> SEQUENCE: 39

Gly Ile Ser Trp Asn Ser Gly Ser Ile Gly Tyr Ala Asp Ser Val Lys
 1               5                  10                  15

Gly

<210> SEQ ID NO 40
<211> LENGTH: 11
<212> TYPE: PRT
<213> ORGANISM: Artificial Sequence -continued

```
<220> FEATURE:
<223> OTHER INFORMATION: LX6960073_G82bS_gl CDR-3 Heavy Chain sequence

<400> SEQUENCE: 40

Glu Gly Ser Trp Asn Tyr Asp Ala Leu Asp Ile
1               5                   10

<210> SEQ ID NO 41
<211> LENGTH: 120
<212> TYPE: PRT
<213> ORGANISM: Artificial Sequence
<220> FEATURE:
<223> OTHER INFORMATION: LX6960073_G82bS_gl Heavy Chain sequence

<400> SEQUENCE: 41

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ser Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Trp Asn Tyr Asp Ala Leu Asp Ile Trp Gly Gln
            100                 105                 110

Gly Thr Met Val Thr Val Ser Ser
        115                 120

<210> SEQ ID NO 42
<211> LENGTH: 17
<212> TYPE: PRT
<213> ORGANISM: Artificial Sequence
<220> FEATURE:
<223> OTHER INFORMATION: LX6960067_ngl1 CDR-2 Heavy Chain sequence

<400> SEQUENCE: 42

Gly Val Ser Leu Gln Glu Leu Tyr Thr Gly Tyr Ala Asp Ser Val Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: LX6960086_ngl1 CDR-2 Heavy Chain sequence

<400> SEQUENCE: 43

Gly Ile Ser Trp Asn Ser Pro Asp Arg Tyr Met Asp Asp Ser Val Lys
1               5                   10                  15

Gly

<210> SEQ ID NO 44
<211> LENGTH: 11
<212> TYPE: PRT
<213> ORGANISM: Artificial Sequence
<220> FEATURE:
<223> OTHER INFORMATION: Lox696 CDR-3 Heavy Chain sequence
```

-continued

<400> SEQUENCE: 44

Glu Gly Asn Trp Asn Tyr Asp Ala Phe Asp Ile
1               5                   10

<210> SEQ ID NO 45
<211> LENGTH: 11
<212> TYPE: PRT
<213> ORGANISM: Artificial Sequence
<220> FEATURE:
<223> OTHER INFORMATION: LX6960067_ngl1 CDR-3 Heavy Chain sequence

<400> SEQUENCE: 45

Glu Gly Ser Trp Asn Tyr Asp Ala Phe Asp Ile
1               5                   10

<210> SEQ ID NO 46
<211> LENGTH: 11
<212> TYPE: PRT
<213> ORGANISM: Artificial Sequence
<220> FEATURE:
<223> OTHER INFORMATION: LX6960073_ngl1 CDR-3 Heavy Chain sequence

<400> SEQUENCE: 46

Glu Gly Ser Trp Asn Tyr Asp Ala Leu Asp Ile
1               5                   10

<210> SEQ ID NO 47
<211> LENGTH: 11
<212> TYPE: PRT
<213> ORGANISM: Artificial Sequence
<220> FEATURE:
<223> OTHER INFORMATION: LX6960101_ngl1 CDR-3 Heavy Chain sequence

<400> SEQUENCE: 47

Glu Gly Asn Trp Asn Tyr Asp Ala Phe Asp Val
1               5                   10

<210> SEQ ID NO 48
<211> LENGTH: 120
<212> TYPE: PRT
<213> ORGANISM: Artificial Sequence
<220> FEATURE:
<223> OTHER INFORMATION: LX6960067_ngl1 Heavy Chain sequence

<400> SEQUENCE: 48

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Val Ser Leu Gln Glu Leu Tyr Thr Gly Tyr Ala Asp Ser Val
    50                  55                  60

Lys Gly Arg Phe Thr Val Ser Gly Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Trp Asn Tyr Asp Ala Phe Asp Ile Trp Gly Arg
            100                 105                 110

Gly Thr Thr Val Thr Val Ser Ser
        115                 120

<210> SEQ ID NO 49
<211> LENGTH: 120
<212> TYPE: PRT
<213> ORGANISM: Artificial Sequence
<220> FEATURE:
<223> OTHER INFORMATION: LX6960071_ngl1 Heavy Chain sequence

<400> SEQUENCE: 49

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Glu Gly Asn Trp Asn Tyr Asp Ala Phe Asp Ile Trp Gly Arg
                100                 105                 110

Gly Thr Thr Val Thr Val Ser Ser
            115                 120

<210> SEQ ID NO 50
<211> LENGTH: 120
<212> TYPE: PRT
<213> ORGANISM: Artificial Sequence
<220> FEATURE:
<223> OTHER INFORMATION: LX6960073_ngl1 Heavy Chain sequence

<400> SEQUENCE: 50

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Ser Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Gly Leu Arg Ala Glu Asp Thr Ala Val Tyr Tyr Cys
                85                  90                  95

Ala Arg Glu Gly Ser Trp Asn Tyr Asp Ala Leu Asp Ile Trp Gly Arg
                100                 105                 110

Gly Thr Thr Val Thr Val Ser Ser
            115                 120

<210> SEQ ID NO 51
<211> LENGTH: 120
<212> TYPE: PRT
<213> ORGANISM: Artificial Sequence
<220> FEATURE:
<223> OTHER INFORMATION: LX6960086_ngl1 Heavy Chain sequence

```
<400> SEQUENCE: 51

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Pro Asp Arg Tyr Met Asp Asp Ser Val
    50                  55                  60

Lys Gly Arg Phe Thr Ile Ser Arg Asp Asn Ala Gln Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Glu Gly Asn Trp Asn Tyr Asp Ala Phe Asp Ile Trp Gly Arg
            100                 105                 110

Gly Thr Thr Val Thr Val Ser Ser
        115                 120

<210> SEQ ID NO 52
<211> LENGTH: 120
<212> TYPE: PRT
<213> ORGANISM: Artificial Sequence
<220> FEATURE:
<223> OTHER INFORMATION: LX6960101_ngl1 Heavy Chain sequence

<400> SEQUENCE: 52

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Gly Leu Arg Ala Glu Asp Thr Ala Val Tyr Tyr Cys
                85                  90                  95

Ala Arg Glu Gly Asn Trp Asn Tyr Asp Ala Phe Asp Val Trp Gly Arg
            100                 105                 110

Gly Thr Thr Val Thr Val Ser Ser
        115                 120

<210> SEQ ID NO 53
<211> LENGTH: 120
<212> TYPE: PRT
<213> ORGANISM: Artificial Sequence
<220> FEATURE:
<223> OTHER INFORMATION: LX6960073_gl Heavy Chain sequence

<400> SEQUENCE: 53

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ser Asp Asp Tyr
            20                  25                  30

Ala Met His Trp Val Arg Gln Ala Pro Gly Lys Gly Leu Glu Trp Val
        35                  40                  45
```

Ser Gly Ile Ser Trp Asn Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Gly Leu Arg Ala Glu Asp Thr Ala Val Tyr Tyr Cys
                 85                  90                  95

Ala Arg Glu Gly Ser Trp Asn Tyr Asp Ala Leu Asp Ile Trp Gly Gln
            100                 105                 110

Gly Thr Met Val Thr Val Ser Ser
            115                 120

<210> SEQ ID NO 54
<211> LENGTH: 120
<212> TYPE: PRT
<213> ORGANISM: Artificial Sequence
<220> FEATURE:
<223> OTHER INFORMATION: Lox696 Heavy Chain sequence

<400> SEQUENCE: 54

Gln Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Asn Trp Asn Tyr Asp Ala Phe Asp Ile Trp Gly Arg
            100                 105                 110

Gly Thr Thr Val Thr Val Ser Ser
            115                 120

<210> SEQ ID NO 55
<211> LENGTH: 14
<212> TYPE: PRT
<213> ORGANISM: Artificial Sequence
<220> FEATURE:
<223> OTHER INFORMATION: LX6960073_G82bS_gl CDR-1 Light Chain sequence

<400> SEQUENCE: 55

Thr Gly Thr Ser Ser Asp Val Gly Gly Tyr Asn Tyr Val Ser
 1               5                  10

<210> SEQ ID NO 56
<211> LENGTH: 7
<212> TYPE: PRT
<213> ORGANISM: Artificial Sequence
<220> FEATURE:
<223> OTHER INFORMATION: LX6960073_G82bS_gl CDR-2 Light Chain sequence

<400> SEQUENCE: 56

Asp Val Ser Lys Arg Pro Ser
 1               5

```
<210> SEQ ID NO 57
<211> LENGTH: 11
<212> TYPE: PRT
<213> ORGANISM: Artificial Sequence
<220> FEATURE:
<223> OTHER INFORMATION: LX6960073_G82bS_gl CDR-3 Light Chain sequence

<400> SEQUENCE: 57

Met Gly Gly Met Gly Arg Ser Thr Asn Trp Val
1               5                   10

<210> SEQ ID NO 58
<211> LENGTH: 111
<212> TYPE: PRT
<213> ORGANISM: Artificial Sequence
<220> FEATURE:
<223> OTHER INFORMATION: LX6960073_G82bS_gl Light Chain sequence

<400> SEQUENCE: 58

Gln Ser Ala Leu Thr Gln Pro Ala Ser Val Ser Gly Ser Pro Gly Gln
1               5                   10                  15

Pro Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Met Gly Gly Met Gly Arg
                85                  90                  95

Ser Thr Asn Trp Val Phe Gly Gly Gly Thr Lys Leu Thr Val Leu
                100                 105                 110

<210> SEQ ID NO 59
<211> LENGTH: 14
<212> TYPE: PRT
<213> ORGANISM: Artificial Sequence
<220> FEATURE:
<223> OTHER INFORMATION: LX6960116_ngl1 CDR-1 Light Chain sequence

<400> SEQUENCE: 59

Thr Gly Thr Ser Asn Asp Val Gly Gly Tyr Asn Tyr Val Ser
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Lox696 CDR-2 Light Chain sequence

<400> SEQUENCE: 60

Asp Val Ser Asn Arg Pro Ser
1               5

<210> SEQ ID NO 61
<211> LENGTH: 11
<212> TYPE: PRT
<213> ORGANISM: Artificial Sequence
<220> FEATURE:
<223> OTHER INFORMATION: Lox696 CDR-3 Light Chain sequence
```

```
<400> SEQUENCE: 61

Ser Ser Tyr Thr Ser Ser Ser Thr Asn Trp Val
1               5                   10

<210> SEQ ID NO 62
<211> LENGTH: 11
<212> TYPE: PRT
<213> ORGANISM: Artificial Sequence
<220> FEATURE:
<223> OTHER INFORMATION: LX6960067_ngl1 CDR-3 Light Chain sequence

<400> SEQUENCE: 62

Leu Gly Arg Thr Trp Ser Ser Thr Asn Trp Val
1               5                   10

<210> SEQ ID NO 63
<211> LENGTH: 11
<212> TYPE: PRT
<213> ORGANISM: Artificial Sequence
<220> FEATURE:
<223> OTHER INFORMATION: LX6960071_ngl1 CDR-3 Light Chain sequence

<400> SEQUENCE: 63

Met Gly Ser Met Gly Arg Ser Thr Asn Trp Val
1               5                   10

<210> SEQ ID NO 64
<211> LENGTH: 11
<212> TYPE: PRT
<213> ORGANISM: Artificial Sequence
<220> FEATURE:
<223> OTHER INFORMATION: LX6960094_ngl1 CDR-3 Light Chain sequence

<400> SEQUENCE: 64

Ala Gln Arg Thr Val Ser Ser Thr Asn Trp Val
1               5                   10

<210> SEQ ID NO 65
<211> LENGTH: 111
<212> TYPE: PRT
<213> ORGANISM: Artificial Sequence
<220> FEATURE:
<223> OTHER INFORMATION: LX6960067_ngl1 Light Chain sequence

<400> SEQUENCE: 65

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Leu Gly Arg Thr Trp Ser
                85                  90                  95

Ser Thr Asn Trp Val Phe Gly Gly Gly Thr Lys Leu Thr Val Leu
            100                 105                 110
```

<210> SEQ ID NO 66
<211> LENGTH: 111
<212> TYPE: PRT
<213> ORGANISM: Artificial Sequence
<220> FEATURE:
<223> OTHER INFORMATION: LX6960071_ngl1 Light Chain sequence

<400> SEQUENCE: 66

```
Gln Ser Ala Leu Thr Gln Pro Ala Ser Val Ser Gly Ser Pro Gly Gln
1               5                   10                  15

Pro Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Met Gly Ser Met Gly Arg
                85                  90                  95

Ser Thr Asn Trp Val Phe Gly Gly Gly Thr Lys Leu Thr Val Leu
            100                 105                 110
```

<210> SEQ ID NO 67
<211> LENGTH: 111
<212> TYPE: PRT
<213> ORGANISM: Artificial Sequence
<220> FEATURE:
<223> OTHER INFORMATION: LX6960073_ngl1 Light Chain sequence

<400> SEQUENCE: 67

```
Gln Ser Ala Leu Thr Gln Pro Ala Ser Val Ser Gly Ser Pro Gly Gln
1               5                   10                  15

Pro Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Met Gly Gly Met Gly Arg
                85                  90                  95

Ser Thr Asn Trp Val Phe Gly Gly Gly Thr Lys Leu Thr Val Leu
            100                 105                 110
```

<210> SEQ ID NO 68
<211> LENGTH: 111
<212> TYPE: PRT
<213> ORGANISM: Artificial Sequence
<220> FEATURE:
<223> OTHER INFORMATION: LX6960094_ngl1 Light Chain sequence

<400> SEQUENCE: 68

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Gln Arg Thr Val Ser
                85                  90                  95

Ser Thr Asn Trp Val Phe Gly Gly Gly Thr Lys Leu Thr Val Leu
            100                 105                 110

<210> SEQ ID NO 69
<211> LENGTH: 111
<212> TYPE: PRT
<213> ORGANISM: Artificial Sequence
<220> FEATURE:
<223> OTHER INFORMATION: LX6960116_ngl1 Light Chain sequence

<400> SEQUENCE: 69

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Met Gly Ser Met Gly Arg
                85                  90                  95

Ser Thr Asn Trp Val Phe Gly Gly Gly Thr Lys Leu Thr Val Leu
            100                 105                 110

<210> SEQ ID NO 70
<211> LENGTH: 111
<212> TYPE: PRT
<213> ORGANISM: Artificial Sequence
<220> FEATURE:
<223> OTHER INFORMATION: Lox696 Light Chain sequence

<400> SEQUENCE: 70

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Asn Trp Val Phe Gly Gly Gly Thr Lys Leu Thr Val Leu
            100                 105                 110

<210> SEQ ID NO 71
<211> LENGTH: 17
<212> TYPE: PRT
<213> ORGANISM: Artificial Sequence

```
<220> FEATURE:
<223> OTHER INFORMATION: Lox514 VH CDR2
<220> FEATURE:
<221> NAME/KEY: misc_feature
<222> LOCATION: (7)..(7)
<223> OTHER INFORMATION: Xaa is Gly, Trp, Tyr, or Phe
<220> FEATURE:
<221> NAME/KEY: misc_feature
<222> LOCATION: (8)..(8)
<223> OTHER INFORMATION: Xaa is Glu, Thr, Gln, Ser, Lys, or Ala
<220> FEATURE:
<221> NAME/KEY: misc_feature
<222> LOCATION: (9)..(9)
<223> OTHER INFORMATION: Xaa is Thr, Tyr, Ile, or Asn
<220> FEATURE:
<221> NAME/KEY: misc_feature
<222> LOCATION: (10)..(10)
<223> OTHER INFORMATION: Xaa is Ile, Ala, Arg, or His
<220> FEATURE:
<221> NAME/KEY: misc_feature
<222> LOCATION: (11)..(11)
<223> OTHER INFORMATION: Xaa is Tyr, Val, Thr, Leu, or Gln
<220> FEATURE:
<221> NAME/KEY: misc_feature
<222> LOCATION: (12)..(12)
<223> OTHER INFORMATION: Xaa is Ala, Asp, Gly, Ser, or His

<400> SEQUENCE: 71

Gly Phe Asp Pro Glu Asp Xaa Xaa Xaa Xaa Xaa Xaa Gln Lys Phe Gln
1               5                   10                  15

Gly

<210> SEQ ID NO 72
<211> LENGTH: 20
<212> TYPE: PRT
<213> ORGANISM: Artificial Sequence
<220> FEATURE:
<223> OTHER INFORMATION: Lox514 VH CDR3
<220> FEATURE:
<221> NAME/KEY: misc_feature
<222> LOCATION: (1)..(1)
<223> OTHER INFORMATION: Xaa is Pro, Ser, or Val
<220> FEATURE:
<221> NAME/KEY: misc_feature
<222> LOCATION: (2)..(2)
<223> OTHER INFORMATION: Xaa is Asn, Thr, Trp, or Asp
<220> FEATURE:
<221> NAME/KEY: misc_feature
<222> LOCATION: (4)..(4)
<223> OTHER INFORMATION: Xaa is Gln, Arg, or Thr
<220> FEATURE:
<221> NAME/KEY: misc_feature
<222> LOCATION: (5)..(5)
<223> OTHER INFORMATION: Xaa is Gln or His
<220> FEATURE:
<221> NAME/KEY: misc_feature
<222> LOCATION: (6)..(6)
<223> OTHER INFORMATION: Xaa is Gly or Gln
<220> FEATURE:
<221> NAME/KEY: misc_feature
<222> LOCATION: (7)..(7)
<223> OTHER INFORMATION: Xaa is Lys or Gly

<400> SEQUENCE: 72

Xaa Xaa Gly Xaa Xaa Xaa Xaa Gly Val Arg Gly Trp Asp Tyr Tyr Tyr
1               5                   10                  15

Gly Met Asp Val
            20

<210> SEQ ID NO 73
<211> LENGTH: 11
<212> TYPE: PRT
<213> ORGANISM: Artificial Sequence
```

```
<220> FEATURE:
<223> OTHER INFORMATION: Lox514 VL CDR3
<220> FEATURE:
<221> NAME/KEY: misc_feature
<222> LOCATION: (6)..(6)
<223> OTHER INFORMATION: Xaa is Ser or Met
<220> FEATURE:
<221> NAME/KEY: misc_feature
<222> LOCATION: (7)..(7)
<223> OTHER INFORMATION: Xaa is Leu, Tyr, or His
<220> FEATURE:
<221> NAME/KEY: misc_feature
<222> LOCATION: (8)..(8)
<223> OTHER INFORMATION: Xaa is Ser or Arg
<220> FEATURE:
<221> NAME/KEY: misc_feature
<222> LOCATION: (9)..(9)
<223> OTHER INFORMATION: Xaa is Gly, Ala, or no amino acid
<220> FEATURE:
<221> NAME/KEY: misc_feature
<222> LOCATION: (10)..(10)
<223> OTHER INFORMATION: Xaa is Trp or Phe
<220> FEATURE:
<221> NAME/KEY: misc_feature
<222> LOCATION: (11)..(11)
<223> OTHER INFORMATION: Xaa is Val, Gly, or Ala

<400> SEQUENCE: 73

Gln Ser Tyr Asp Ser Xaa Xaa Xaa Xaa Xaa Xaa
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Lox696 VH CDR2
<220> FEATURE:
<221> NAME/KEY: misc_feature
<222> LOCATION: (2)..(2)
<223> OTHER INFORMATION: Xaa is Ile or Val
<220> FEATURE:
<221> NAME/KEY: misc_feature
<222> LOCATION: (4)..(4)
<223> OTHER INFORMATION: Xaa is Trp or Leu
<220> FEATURE:
<221> NAME/KEY: misc_feature
<222> LOCATION: (5)..(5)
<223> OTHER INFORMATION: Xaa is Asn or Gln
<220> FEATURE:
<221> NAME/KEY: misc_feature
<222> LOCATION: (6)..(6)
<223> OTHER INFORMATION: Xaa is Ser or Glu
<220> FEATURE:
<221> NAME/KEY: misc_feature
<222> LOCATION: (7)..(7)
<223> OTHER INFORMATION: Xaa is Gly, Leu, or Pro
<220> FEATURE:
<221> NAME/KEY: misc_feature
<222> LOCATION: (8)..(8)
<223> OTHER INFORMATION: Xaa is Ser, Tyr, or Asp
<220> FEATURE:
<221> NAME/KEY: misc_feature
<222> LOCATION: (9)..(9)
<223> OTHER INFORMATION: Xaa is Ile, Thr, or Arg
<220> FEATURE:
<221> NAME/KEY: misc_feature
<222> LOCATION: (10)..(10)
<223> OTHER INFORMATION: Xaa is Gly or Tyr
<220> FEATURE:
<221> NAME/KEY: misc_feature
<222> LOCATION: (11)..(11)
<223> OTHER INFORMATION: Xaa is Tyr or Met
<220> FEATURE:
<221> NAME/KEY: misc_feature
<222> LOCATION: (12)..(12)
<223> OTHER INFORMATION: Xaa is Ala or Asp
```

```
<400> SEQUENCE: 74

Gly Xaa Ser Xaa Xaa Xaa Xaa Xaa Xaa Xaa Xaa Asp Ser Val Lys
1               5                   10                  15

Gly

<210> SEQ ID NO 75
<211> LENGTH: 11
<212> TYPE: PRT
<213> ORGANISM: Artificial Sequence
<220> FEATURE:
<223> OTHER INFORMATION: Lox696 VH CDR3
<220> FEATURE:
<221> NAME/KEY: misc_feature
<222> LOCATION: (3)..(3)
<223> OTHER INFORMATION: Xaa is Asn or Ser
<220> FEATURE:
<221> NAME/KEY: misc_feature
<222> LOCATION: (9)..(9)
<223> OTHER INFORMATION: Xaa is Phe or Leu
<220> FEATURE:
<221> NAME/KEY: misc_feature
<222> LOCATION: (11)..(11)
<223> OTHER INFORMATION: Xaa is Ile or Val

<400> SEQUENCE: 75

Glu Gly Xaa Trp Asn Tyr Asp Ala Xaa Asp Xaa
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Lox696 VL CDR1
<220> FEATURE:
<221> NAME/KEY: misc_feature
<222> LOCATION: (5)..(5)
<223> OTHER INFORMATION: Xaa is Ser or Asn

<400> SEQUENCE: 76

Thr Gly Thr Ser Xaa Asp Val Gly Gly Tyr Asn Tyr Val Ser
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Lox696 VL CDR2
<220> FEATURE:
<221> NAME/KEY: misc_feature
<222> LOCATION: (4)..(4)
<223> OTHER INFORMATION: Xaa is Asn or Lys

<400> SEQUENCE: 77

Asp Val Ser Xaa Arg Pro Ser
1               5

<210> SEQ ID NO 78
<211> LENGTH: 11
<212> TYPE: PRT
<213> ORGANISM: Artificial Sequence
<220> FEATURE:
<223> OTHER INFORMATION: Lox696 VL CDR3
<220> FEATURE:
<221> NAME/KEY: misc_feature
<222> LOCATION: (1)..(1)
<223> OTHER INFORMATION: Xaa is Ser, Leu, Met, or Ala
```

```
<220> FEATURE:
<221> NAME/KEY: misc_feature
<222> LOCATION: (2)..(2)
<223> OTHER INFORMATION: Xaa is Ser, Gly, or Gln
<220> FEATURE:
<221> NAME/KEY: misc_feature
<222> LOCATION: (3)..(3)
<223> OTHER INFORMATION: Xaa is Tyr, Arg, Ser, or Gly
<220> FEATURE:
<221> NAME/KEY: misc_feature
<222> LOCATION: (4)..(4)
<223> OTHER INFORMATION: Xaa is Thr or Met
<220> FEATURE:
<221> NAME/KEY: misc_feature
<222> LOCATION: (5)..(5)
<223> OTHER INFORMATION: Xaa is Ser, Trp, Gly, or Val
<220> FEATURE:
<221> NAME/KEY: misc_feature
<222> LOCATION: (6)..(6)
<223> OTHER INFORMATION: Xaa is Ser or Arg

<400> SEQUENCE: 78

Xaa Xaa Xaa Xaa Xaa Xaa Ser Thr Asn Trp Val
1               5                   10
```